(12) United States Patent
Saito

(10) Patent No.: US 7,393,945 B2
(45) Date of Patent: Jul. 1, 2008

(54) ESTROGEN RECEPTOR GENES AND UTILIZATION THEREOF

(75) Inventor: Koichi Saito, Takarazuka (JP)

(73) Assignee: Sumitomo Chemical Company Limited, Osaka (JP)

(*) Notice: Subject to any disclaimer, the term of this patent is extended or adjusted under 35 U.S.C. 154(b) by 100 days.

(21) Appl. No.: 10/501,227

(22) PCT Filed: Jul. 23, 2002

(86) PCT No.: PCT/JP02/07404

§ 371 (c)(1),
(2), (4) Date: Mar. 7, 2005

(65) Prior Publication Data

US 2006/0141560 A1    Jun. 29, 2006

(30) Foreign Application Priority Data

Jan. 11, 2002    (JP) ............................. 2002-004395

(51) Int. Cl.
C07H 21/04 (2006.01)
C07H 21/02 (2006.01)
C12N 15/00 (2006.01)
C12N 5/00 (2006.01)
C12N 5/06 (2006.01)
C12P 21/06 (2006.01)
G01N 33/566 (2006.01)
G01N 33/567 (2006.01)

(52) U.S. Cl. ............... 536/23.5; 536/23.1; 536/24.1; 435/320.1; 435/325; 435/69.1; 435/361; 436/501; 436/503

(58) Field of Classification Search ............... None
See application file for complete search history.

(56) References Cited

U.S. PATENT DOCUMENTS

2002/0129386 A1    9/2002    Yamashita

FOREIGN PATENT DOCUMENTS

| JP | 2000-201688 A | 7/2000 |
| JP | 2001-197890 A | 7/2001 |
| JP | 2001-352992 A | 12/2001 |

OTHER PUBLICATIONS

Ruff et al. 2000. Breast Cancer Res 2:353-359.*
M.B. Hawkins et al., "Identification of a third district estrogen receptor and reclassification of estrogen receptors in teleosts," Proc. Natl. Acad. Sci. USA, vol. 97, No. 20, pp. 10751-10756 (2000).
K. Touhata et al., "Sequence and Expression of a cDNA Encoding the Red Seabream Estrogen Receptor," Fisheries Sci., vol. 64, No. 1, pp. 131-135 (1998).
X. Chang et al., "Molecular Cloning of Estrogen Receptors alpha and beta in the Ovary of a Teleost Fish, the Tilapia (*Oreochromis niloticus*)," Zoological Sci., vol. 16, pp. 653-658 (1999).
N.S. Tan et al., "Transcription regulatory signals in the 5' and 3' regions of *Oreochromis aureus* ER gene," Mol. & Cell Endocrinol., vol. 123, pp. 149-161 (1996).
T. Todo et al., "Molecular cloning and characterization of Japanese eel estrogen receptor cDNA," Mol. & Cell Endocrinol., vol. 119, pp. 37-45 (1996).
C.H. Ma et al., "cDNA cloning and expression of a novel estrogen receptor beta-subtype in goldfish (*Carassius auratus*)," Biochim. Biophys. Acta, vol. 1490, pp. 145-152 (2000).
F. Pakdel et al., "Full-length sequence and in vitro expression of rainbow trout estrogen receptor cDNA," Mol. & Cell Endocrinol., vol. 71, pp. 195-204 (1990).
International Search Report, dated Nov. 2, 2005, from the International Searching Authority of the PCT in counterpart International Application No. PCT/JP02/07404 (3 pages).

* cited by examiner

*Primary Examiner*—Manjunath Rao
*Assistant Examiner*—Shulamith H Shafer
(74) *Attorney, Agent, or Firm*—Panitch Schwarze Belisario + Nadel LLP

(57) ABSTRACT

An estrogen receptor gene and utilization of the estrogen gene are described. The estrogen receptor gene has a nucleotide sequence coding for any of the following amino acid sequences: (a) the amino acid sequence of SEQ ID NO: 1, (b) the amino acid sequence of SEQ ID NO: 4, (c) an amino acid sequence exhibiting 95% or more amino acid identity to the amino acid sequence of SEQ ID NO: 1, and (d) an amino acid sequence exhibiting 95% or more amino acid identity to the amino acid sequence of SEQ ID NO: 4.

20 Claims, 13 Drawing Sheets concentration of DES concentration of genistein concentration of o,p'-DDT concentration of 4-OH-HTM concentration of estradiol concentration of bisphenol A concentration of DES concentration of genistein concentration of genistein concentration of coumesterol

SEQUENCE LISTING

<160> NUMBER OF SEQ ID NOS: 48

<210> SEQ ID NO 1
<211> LENGTH: 506
<212> TYPE: PRT
<213> ORGANISM: Blue Gill

<400> SEQUENCE: 1

Met Ser Leu Lys Asp Trp Leu Leu Gly Lys Glu Arg Thr Val Val Thr
 1               5                  10                  15

-continued

```
Met Glu Glu Leu Arg Ser Ser Val Pro Ser Ser Gln Gln Pro Val Pro
            20                  25                  30

Arg Glu Asp Gln Cys Ala Thr Ser Asp Glu Ser Tyr Ser Val Gly Glu
            35                  40                  45

Ser Gly Ala Gly Ala Arg Gly Phe Glu Met Ala Lys Glu Met Arg Phe
            50                  55                  60

Cys Ala Val Cys Ser Asp Tyr Ala Ser Gly Tyr His Tyr Gly Val Trp
65                  70                  75                  80

Ser Cys Glu Gly Cys Lys Ala Phe Phe Lys Arg Ser Ile Gln Gly His
                85                  90                  95

Asn Asp Tyr Met Cys Pro Ala Thr Asn Gln Cys Thr Ile Asp Arg Asn
            100                 105                 110

Arg Arg Lys Ser Cys Gln Ala Cys Arg Leu Arg Lys Cys Tyr Glu Val
            115                 120                 125

Gly Met Met Lys Gly Gly Val Arg Lys Asp Arg Gly Arg Val Leu Arg
        130                 135                 140

Arg Asp Lys Arg Arg Ala Gly Thr Asn Asp Arg Glu Lys Ala Ser Lys
145                 150                 155                 160

Asp Leu Glu Tyr Lys Thr Val Pro Pro Gln Asp Arg Arg Lys His Ser
                165                 170                 175

Ser Ser Ser Ser Ala Gly Gly Gly Gly Lys Ser Ser Val Thr Gly
            180                 185                 190

Met Ser Pro Asp Gln Val Leu Leu Leu Leu Gln Gly Ala Glu Pro Pro
            195                 200                 205

Met Leu Cys Ser Arg Gln Lys Leu Ser Arg Pro Tyr Thr Glu Val Thr
            210                 215                 220

Ile Met Thr Leu Leu Thr Ser Met Ala Asp Lys Glu Leu Val His Met
225                 230                 235                 240

Ile Thr Trp Ala Lys Lys Leu Pro Gly Phe Leu Gln Leu Ser Leu His
                245                 250                 255

Asp Gln Val Gln Leu Leu Glu Ser Ser Trp Leu Glu Val Leu Met Ile
            260                 265                 270

Gly Leu Ile Trp Arg Ser Ile His Cys Pro Gly Lys Leu Ile Phe Ala
        275                 280                 285

Gln Asp Leu Ile Leu Asp Arg Asn Glu Gly Asp Cys Val Glu Gly Phe
        290                 295                 300

Val Glu Ile Phe Asp Met Leu Leu Ala Thr Ala Ser Arg Phe Arg Met
305                 310                 315                 320

Leu Lys Leu Lys Pro Glu Glu Phe Val Cys Leu Lys Ala Ile Ile Leu
                325                 330                 335

Leu Asn Ser Gly Ala Phe Ser Phe Cys Thr Gly Thr Met Glu Pro Leu
            340                 345                 350

His Asn Ser Met Ala Val Gln Asn Met Leu Asp Thr Ile Thr Asp Ala
            355                 360                 365

Leu Ile His His Ile Ser Gln Ser Gly Cys Ser Ala Gln Gln Ser
        370                 375                 380

Arg Arg Gln Ala Gln Leu Leu Leu Leu Ser His Ile Arg His Met
385                 390                 395                 400

Ser Asn Lys Gly Met Glu His Leu Tyr Ser Met Lys Cys Lys Asn Lys
                405                 410                 415

Val Pro Leu Tyr Asp Leu Leu Leu Glu Met Leu Asp Ala His Arg Ile
            420                 425                 430

His Arg Pro Asp Arg Pro Ala Gln Phe Trp Ser Gln Ala Asp Gly Glu
```

```
                        435                 440                 445
Pro Pro Phe Ile Asn Asn Asn Ser Ser Ser Gly Ser Asn Gly
    450                 455                 460

Gly Val Ser Ser Val Gly Ser Ser Gly Pro Arg Val Asn His
465                 470                 475                 480

Glu Ser Pro Ser Arg Gly Pro Thr Gly Pro Gly Val Leu Gln Tyr Gly
                485                 490                 495

Gly Ser Arg Ser Asp Cys Thr His Ile Leu
                500                 505

<210> SEQ ID NO 2
<211> LENGTH: 3499
<212> TYPE: DNA
<213> ORGANISM: Blue Gill
<220> FEATURE:
<221> NAME/KEY: CDS
<222> LOCATION: (424)...(1944)

<400> SEQUENCE: 2
caggcagagc ccagcgcaga gcagacagcc ttgtggaaca gtactcagac ccaggatcag      60
ctcagccttc acagagctgg agaccctctc cccacaacgt ccctcgcctc cgctgcgtgc     120
ccctctcagt gacatgtacc ctgaagagag caggggtcc ggaggggtag ccactgtgga      180
ctttctggaa gggacctacg attatgccgc ccccacccct gccccgactc ctctttacag     240
ccagtctggc tactactctg tacctctgga cgcccaaggg ccaccctcag atggcagcct     300
tcagtccctg gcagcgggc ctaccagtcc tcttgtgttt gtgccagtcca gccccagact    360 cagccccttt atgcacccgc ccagccacca ctatctggaa accacctcaa cacccgtcta     420 cag atg agt ctg aaa gac tgg tta tta gga aaa gaa agg acg gtg gtg       468
    Met Ser Leu Lys Asp Trp Leu Leu Gly Lys Glu Arg Thr Val Val
      1               5                  10                  15 acc atg gag gag ctg agg tct agt gtc cca tcc agc cag cag cca gtt       516
Thr Met Glu Glu Leu Arg Ser Ser Val Pro Ser Ser Gln Gln Pro Val
                 20                  25                  30 ccc aga gag gac cag tgt gcc acc agt gat gag tcc tat agt gtg ggg       564
Pro Arg Glu Asp Gln Cys Ala Thr Ser Asp Glu Ser Tyr Ser Val Gly
             35                  40                  45 gag tca ggg gct gga gcc agg ggg ttt gag atg gcc aag gag atg cgt       612
Glu Ser Gly Ala Gly Ala Arg Gly Phe Glu Met Ala Lys Glu Met Arg
         50                  55                  60 ttc tgt gct gtg tgc agt gac tat gcc tct ggg tac cac tac ggg gtg       660
Phe Cys Ala Val Cys Ser Asp Tyr Ala Ser Gly Tyr His Tyr Gly Val
     65                  70                  75 tgg tcc tgt gaa ggc tgt aag gcc ttc ttt aag agg agc atc cag ggt       708
Trp Ser Cys Glu Gly Cys Lys Ala Phe Phe Lys Arg Ser Ile Gln Gly
 80                  85                  90                  95 cac aat gac tat atg tgc cca gca acc aat cag tgt act att gac agg       756
His Asn Asp Tyr Met Cys Pro Ala Thr Asn Gln Cys Thr Ile Asp Arg
                100                 105                 110 aat cgg aga aag agc tgc cag gct tgc cgt ctt agg aag tgt tat gaa       804
Asn Arg Arg Lys Ser Cys Gln Ala Cys Arg Leu Arg Lys Cys Tyr Glu
             115                 120                 125 gtg ggc atg atg aaa gga ggt gtt cgc aag gac cgt ggc cgt gtt ttg       852
Val Gly Met Met Lys Gly Gly Val Arg Lys Asp Arg Gly Arg Val Leu
         130                 135                 140 cgc cgt gat aaa cga cgt gct gga acc aat gac cga gag aag gcc tct       900
Arg Arg Asp Lys Arg Arg Ala Gly Thr Asn Asp Arg Glu Lys Ala Ser
     145                 150                 155
```

```
aag gac ctg gag tac aaa aca gtg ccc cct cag gac agg agg aaa cac        948
Lys Asp Leu Glu Tyr Lys Thr Val Pro Pro Gln Asp Arg Arg Lys His
160                 165                 170                 175 agc agc agc agc agt gcc ggt ggt gga gga gga aaa tca tca gtg acc        996
Ser Ser Ser Ser Ser Ala Gly Gly Gly Gly Gly Lys Ser Ser Val Thr
                180                 185                 190 ggg atg tct cct gac cag gtg ctc ctc ctg ctc cag ggt gcc gag ccc       1044
Gly Met Ser Pro Asp Gln Val Leu Leu Leu Leu Gln Gly Ala Glu Pro
            195                 200                 205 cca atg ctg tgc tcc cgt cag aag ctg agc cga ccg tac acc gag gtc       1092
Pro Met Leu Cys Ser Arg Gln Lys Leu Ser Arg Pro Tyr Thr Glu Val
        210                 215                 220 acc ata atg aca cta ctc acc agc atg gcc gat aag gag ctg gtc cac       1140
Thr Ile Met Thr Leu Leu Thr Ser Met Ala Asp Lys Glu Leu Val His
    225                 230                 235 atg atc acc tgg gcc aag aag ctt cca ggt ttc ctg cag ctg tct ctc       1188
Met Ile Thr Trp Ala Lys Lys Leu Pro Gly Phe Leu Gln Leu Ser Leu
240                 245                 250                 255 cat gac cag gtg cag ctg ctg gag agc tcg tgg ctg gag gtg ctg atg       1236
His Asp Gln Val Gln Leu Leu Glu Ser Ser Trp Leu Glu Val Leu Met
                260                 265                 270 att ggg ctc ata tgg agg tcc atc cac tgc ccc ggc aaa ctc atc ttc       1284
Ile Gly Leu Ile Trp Arg Ser Ile His Cys Pro Gly Lys Leu Ile Phe
            275                 280                 285 gca cag gac ctc ata ctg gac agg aat gaa ggt gac tgt gtg gaa ggc       1332
Ala Gln Asp Leu Ile Leu Asp Arg Asn Glu Gly Asp Cys Val Glu Gly
        290                 295                 300 ttt gtt gag atc ttc gac atg ctg ctg gcc act gcc tcc cgc ttc cgc       1380
Phe Val Glu Ile Phe Asp Met Leu Leu Ala Thr Ala Ser Arg Phe Arg
    305                 310                 315 atg ctc aaa ctc aaa cct gag gag ttt gtc tgc ctc aaa gct atc atc       1428
Met Leu Lys Leu Lys Pro Glu Glu Phe Val Cys Leu Lys Ala Ile Ile
320                 325                 330                 335 ctg ctc aac tct ggt gcc ttc tct ttc tgc acc ggc aca atg gag ccc       1476
Leu Leu Asn Ser Gly Ala Phe Ser Phe Cys Thr Gly Thr Met Glu Pro
                340                 345                 350 ctc cac aac agc atg gca gtg cag aac atg ctg gac acc atc aca gac       1524
Leu His Asn Ser Met Ala Val Gln Asn Met Leu Asp Thr Ile Thr Asp
            355                 360                 365 gct ctc ata cat cat atc agc caa tca gga tgc tcg gct cag cag cag       1572
Ala Leu Ile His His Ile Ser Gln Ser Gly Cys Ser Ala Gln Gln Gln
        370                 375                 380 tcg agg cgg cag gcc cag ctg ctc ctc ctg tcc cac atc agg cac            1620
Ser Arg Arg Gln Ala Gln Leu Leu Leu Leu Ser His Ile Arg His
385                 390                 395 atg agc aac aaa ggc atg gag cat ctc tac agc atg aag tgc aag aac       1668
Met Ser Asn Lys Gly Met Glu His Leu Tyr Ser Met Lys Cys Lys Asn
400                 405                 410                 415 aaa gtg cct ctt tac gac ctt ctg ctg gag atg ttg gac gct cac cgt       1716
Lys Val Pro Leu Tyr Asp Leu Leu Leu Glu Met Leu Asp Ala His Arg
                420                 425                 430 ata cac cgc cca gac aga cca gct cag ttc tgg tcc cag gct gac gga       1764
Ile His Arg Pro Asp Arg Pro Ala Gln Phe Trp Ser Gln Ala Asp Gly
            435                 440                 445 gag cct ccc ttc att aac aac aac aac agc agc aac agt ggc agc aat       1812
Glu Pro Pro Phe Ile Asn Asn Asn Asn Ser Ser Asn Ser Gly Ser Asn
        450                 455                 460 ggc ggc gtc tcc tct tca gtc ggt tcc agt tca gga ccc cga gtc aac       1860
Gly Gly Val Ser Ser Ser Val Gly Ser Ser Ser Gly Pro Arg Val Asn
    465                 470                 475
```

```
cac gag agc ccg agc aga gga ccc aca ggt cca gga gtc ctg cag tac    1908
His Glu Ser Pro Ser Arg Gly Pro Thr Gly Pro Gly Val Leu Gln Tyr
480                 485                 490                 495 gga ggg tcc cgc tct gac tgc acc cac atc cta tga ggccgagcac aacaaa  1960
Gly Gly Ser Arg Ser Asp Cys Thr His Ile Leu
                500                 505 catctgaagg tcaaaagtaa ttttacaga tgatgtgtgt tgtacagaat gaaagctaaa   2020
ggttgtattt taattaattt catgagataa ttatttataa attaagtgat tttatagttg   2080
taactgtttt agggagtttt ttttcctttg cactaatcta gttcactaca acacgagctt   2140
caatgcaggc aatctactat gctgcctttc ataatatctg tgattctgag tgagtacagc   2200 ttaattttc caggtgttag gtcatattgt ggcactcagc tatggtgatt tgaaatgaca    2260
agcagctaat ttgcctttgt atttgcctca accaaagtgc acttcttctt gggtttattg   2320
ggcattgttt ttacttttac atattgggat taggatgatc agacactaaa ctatgataaa   2380
aaacaggttc aaatgaatgt gtgatttatt ttgtgtttaa attccaacat cattaaagag   2440
cctgaacgtc aggtattgtg tcttaagcgt gcacgcaaac tttaaacttc tggaaaacaa   2500
atatttctat gatgaaatta taaaattaac agtgattgag gatgtatgtt gaattcagag   2560
tagatacaat ttgcacaatc aaatcctaga gcactgatca cattatgaaa gaagcaaagc   2620
tttcacaact ttattgttgg gtaacttcac cacatccagc ttttttgtgaa tggtaggttt   2680 gttctgtagg cttacatgca caagagtttt ttttctgaat ttgagatatt ttatgtgtgt    2740
ctgcaagaga aagactgaga aatctgagga aatttgctat aagtggccct aagctttcta   2800
tcttgatgca gttcagaatt tcaaaatgtt actattcatc cactaattca gtgattacat   2860
gttgagtttg gcttgattta cacaactcca aaagcctagt tatcattaaa tatgtgcata   2920
tgcaattgtt tttatttgt ttaaatggaa caaatttaat ctaaatctaa tatggacctg    2980
accaggtgtt ttcttattta gctgctatac actgctaagc accattgtta atagtttggt   3040
ttatatagct aaatagcttt ttccatgacc atcaaaggcc tccaaaagaa agctaatgtt   3100 cttcctaat tctgtgataa acagactcca aaatcacact ggatggtcac tgaacaagtc   3160
ctgcttcatg tttgtttaca tgtcaaccag caacgtcagc acacctgtgc tgttttgtat   3220
cctcccatga acagttgttc agtcacaggt ttgtcacaca ggtagaacaa tctgttaata   3280
tactgaaaaa aaggccagag gttgacgtgt agagaatgtt gccagaatac aaatgataaa   3340
caaagatctg tgccacttaa acaagaatgg aaagcctcta cagggtca ggaaactgga    3400 tttggacact tgaagtgcaa gtcaaacctg acctgtcatc tgtttactgt gcataaaaat   3460
aaaaacatta attgggaaaa aaaaaaaaaa aaaaaaaa                          3499

<210> SEQ ID NO 3
<211> LENGTH: 996
<212> TYPE: DNA
<213> ORGANISM: Blue Gill

<400> SEQUENCE: 3
aggagcatcc aaggtcacaa tgactacatg tgcccagcaa ccaatcagtg tactattgac    60
aggaatcgga gaaagagctg ccaggcttgc cgtcttagga agtgttatga agtgggcatg   120
atgaaaggag gtgttcgcaa ggaccgtggc cgtgttttgc gccgtgataa acgacgtgct   180
ggaaccaatg accgagagaa ggcctctaag gacctggagt acaaaacagt gcccctcag    240 gacaggagga aacacagcag cagcagcagt gccggtggtg gaggaggaaa atcatcagtg   300
```

-continued

```
accgggatgt ctcctgacca ggtgctcctc ctgctccagg gtgccgagcc cccaatgctg    360
tgctcccgtc agaagctgag ccgaccgtac accgaggtca ccataatgac actactcacc    420
agcatggccg ataaggagct ggtccacatg atcacctggg ccaagaagct tccaggtttc    480
ctgcagctgt ctctccatga ccaggtgcag ctgctggaga gctcgtggct ggaggtgctg    540
atgattgggc tcatatggag gtccatccac tgccccggca aactcatctt cgcacaggac    600
ctcatactgg acaggaatga aggtgactgt gtggaaggct tgttgagat cttcgacatg     660 ctgctggcca ctgcctcccg cttccgcatg ctcaaactca acctgagga gtttgtctgc     720 ctcaaagcta tcatcctgct caactctggt gccttctctt tctgcaccgg cacaatggag    780
cccctccaca acagcatggc agtgcagaac atgctggaca ccatcacaga cgctctcata    840
catcatatca gccaatcagg atgctcggct cagcagcagt cgaggcggca ggcccagctg    900
ctgctcctgc tctcccacat caggcacatg agcaacaaag gcatggagca tctctgcagc    960
atgaagtgca agaacaaagt gcctctgtac gacctg    996
```

<210> SEQ ID NO 4
<211> LENGTH: 582
<212> TYPE: PRT
<213> ORGANISM: Blue Gill

<400> SEQUENCE: 4

```
Met Tyr Pro Glu Glu Ser Arg Gly Ser Gly Gly Val Ala Thr Val Asp
 1               5                  10                  15

Phe Leu Glu Gly Thr Tyr Asp Tyr Ala Ala Pro Thr Pro Ala Pro Thr
                20                  25                  30

Pro Leu Tyr Ser Gln Ser Gly Tyr Tyr Ser Val Pro Leu Asp Ala Gln
            35                  40                  45

Gly Pro Pro Ser Asp Gly Ser Leu Gln Ser Leu Gly Ser Gly Pro Thr
        50                  55                  60

Ser Pro Leu Val Phe Val Pro Ser Ser Pro Arg Leu Ser Pro Phe Met
 65                  70                  75                  80

His Pro Pro Ser His His Tyr Leu Glu Thr Thr Ser Thr Pro Val Tyr
                85                  90                  95

Arg Ser Ser Val Pro Ser Ser Gln Gln Pro Val Pro Arg Glu Asp Gln
            100                 105                 110

Cys Ala Thr Ser Asp Glu Ser Tyr Ser Val Gly Glu Ser Gly Ala Gly
        115                 120                 125

Ala Arg Gly Phe Glu Met Ala Lys Glu Met Arg Phe Cys Ala Val Cys
    130                 135                 140

Ser Asp Tyr Ala Ser Gly Tyr His Tyr Gly Val Trp Ser Cys Glu Gly
145                 150                 155                 160

Cys Lys Ala Phe Phe Lys Arg Ser Ile Gln Gly His Asn Asp Tyr Met
                165                 170                 175

Cys Pro Ala Thr Asn Gln Cys Thr Ile Asp Arg Asn Arg Arg Lys Ser
            180                 185                 190

Cys Gln Ala Cys Arg Leu Arg Lys Cys Tyr Glu Val Gly Met Met Lys
        195                 200                 205

Gly Gly Val Arg Lys Asp Arg Gly Arg Val Leu Arg Arg Asp Lys Arg
    210                 215                 220

Arg Ala Gly Thr Asn Asp Arg Glu Lys Ala Ser Lys Asp Leu Glu Tyr
225                 230                 235                 240

Lys Thr Val Pro Pro Gln Asp Arg Arg Lys His Ser Ser Ser Ser Ser
                245                 250                 255
```

```
Ala Gly Gly Gly Gly Lys Ser Ser Val Thr Gly Met Ser Pro Asp
        260                 265                 270

Gln Val Leu Leu Leu Gln Gly Ala Glu Pro Pro Met Leu Cys Ser
    275                 280                 285

Arg Gln Lys Leu Ser Arg Pro Tyr Thr Glu Val Thr Ile Met Thr Leu
    290                 295                 300

Leu Thr Ser Met Ala Asp Lys Glu Leu Val His Met Ile Thr Trp Ala
305                 310                 315                 320

Lys Lys Leu Pro Gly Phe Leu Gln Leu Ser Leu His Asp Gln Val Gln
                325                 330                 335

Leu Leu Glu Ser Ser Trp Leu Glu Val Leu Met Ile Gly Leu Ile Trp
                340                 345                 350

Arg Ser Ile His Cys Pro Gly Lys Leu Ile Phe Ala Gln Asp Leu Ile
            355                 360                 365

Leu Asp Arg Asn Glu Gly Asp Cys Val Glu Gly Phe Val Glu Ile Phe
    370                 375                 380

Asp Met Leu Leu Ala Thr Ala Ser Arg Phe Arg Met Leu Lys Leu Lys
385                 390                 395                 400

Pro Glu Glu Phe Val Cys Leu Lys Ala Ile Ile Leu Leu Asn Ser Gly
                405                 410                 415

Ala Phe Ser Phe Cys Thr Gly Thr Met Glu Pro Leu His Asn Ser Met
                420                 425                 430

Ala Val Gln Asn Met Leu Asp Thr Ile Thr Asp Ala Leu Ile His His
                435                 440                 445

Ile Ser Gln Ser Gly Cys Ser Ala Gln Gln Ser Arg Arg Gln Ala
450                 455                 460

Gln Leu Leu Leu Leu Leu Ser His Ile Arg His Met Ser Asn Lys Gly
465                 470                 475                 480

Met Glu His Leu Tyr Ser Met Lys Cys Lys Asn Lys Val Pro Leu Tyr
                485                 490                 495

Asp Leu Leu Leu Glu Met Leu Asp Ala His Arg Ile His Arg Pro Asp
                500                 505                 510

Arg Pro Ala Gln Phe Trp Ser Gln Ala Asp Gly Glu Pro Pro Phe Ile
    515                 520                 525

Asn Asn Asn Asn Ser Ser Asn Ser Gly Ser Asn Gly Gly Val Ser Ser
                530                 535                 540

Ser Val Gly Ser Ser Ser Gly Pro Arg Val Asn His Glu Ser Pro Ser
545                 550                 555                 560

Arg Gly Pro Thr Gly Pro Gly Val Leu Gln Tyr Gly Gly Ser Arg Ser
                565                 570                 575

Asp Cys Thr His Ile Leu
                580

<210> SEQ ID NO 5
<211> LENGTH: 1824
<212> TYPE: DNA
<213> ORGANISM: Blue Gill
<220> FEATURE:
<221> NAME/KEY: CDS
<222> LOCATION: (74)...(1822)

<400> SEQUENCE: 5
ctcagccttc acagagctgg agaccctctc cccacaacgt ccctcgcctc cgctgcgtgc      60
ccctctcagt gac atg tac cct gaa gag agc agg ggg tcc gga ggg gta       109
            Met Tyr Pro Glu Glu Ser Arg Gly Ser Gly Gly Val
```

-continued

```
            1               5                   10
gcc act gtg gac ttt ctg gaa ggg acc tac gat tat gcc gcc ccc acc      157
Ala Thr Val Asp Phe Leu Glu Gly Thr Tyr Asp Tyr Ala Ala Pro Thr
             15                  20                  25 cct gcc ccg act cct ctt tac agc cag tct ggc tac tac tct gta cct      205
Pro Ala Pro Thr Pro Leu Tyr Ser Gln Ser Gly Tyr Tyr Ser Val Pro
 30                  35                  40 ctg gac gcc caa ggg cca ccc tca gat ggc agc ctt cag tcc ctg ggc      253
Leu Asp Ala Gln Gly Pro Pro Ser Asp Gly Ser Leu Gln Ser Leu Gly
 45                  50                  55                  60 agc ggg cct acc agt cct ctt gtg ttt gtg ccg tcc agc ccc aga ctc      301
Ser Gly Pro Thr Ser Pro Leu Val Phe Val Pro Ser Ser Pro Arg Leu
             65                  70                  75 agc ccc ttt atg cac ccg ccc agc cac cac tat ctg gaa acc acc tca      349
Ser Pro Phe Met His Pro Pro Ser His His Tyr Leu Glu Thr Thr Ser
             80                  85                  90 aca ccc gtc tac agg tct agt gtc cca tcc agc cag cag cca gtt ccc      397
Thr Pro Val Tyr Arg Ser Ser Val Pro Ser Ser Gln Gln Pro Val Pro
             95                  100                 105 aga gag gac cag tgt gcc acc agt gat gag tcc tat agt gtg ggg gag      445
Arg Glu Asp Gln Cys Ala Thr Ser Asp Glu Ser Tyr Ser Val Gly Glu
 110                 115                 120 tca ggg gct gga gcc agg ggg ttt gag atg gcc aag gag atg cgt ttc      493
Ser Gly Ala Gly Ala Arg Gly Phe Glu Met Ala Lys Glu Met Arg Phe
125                 130                 135                 140 tgt gct gtg tgc agt gac tat gcc tct ggg tac cac tac ggg gtg tgg      541
Cys Ala Val Cys Ser Asp Tyr Ala Ser Gly Tyr His Tyr Gly Val Trp
             145                 150                 155 tcc tgt gaa ggc tgt aag gcc ttc ttt aag agg agc atc cag ggt cac      589
Ser Cys Glu Gly Cys Lys Ala Phe Phe Lys Arg Ser Ile Gln Gly His
             160                 165                 170 aat gac tat atg tgc cca gca acc aat cag tgt act att gac agg aat      637
Asn Asp Tyr Met Cys Pro Ala Thr Asn Gln Cys Thr Ile Asp Arg Asn
             175                 180                 185 cgg aga aag agc tgc cag gct tgc cgt ctt agg aag tgt tat gaa gtg      685
Arg Arg Lys Ser Cys Gln Ala Cys Arg Leu Arg Lys Cys Tyr Glu Val
 190                 195                 200 ggc atg atg aaa gga ggt gtt cgc aag gac cgt ggc cgt gtt ttg cgc      733
Gly Met Met Lys Gly Gly Val Arg Lys Asp Arg Gly Arg Val Leu Arg
205                 210                 215                 220 cgt gat aaa cga cgt gct gga acc aat gac cga gag aag gcc tct aag      781
Arg Asp Lys Arg Arg Ala Gly Thr Asn Asp Arg Glu Lys Ala Ser Lys
             225                 230                 235 gac ctg gag tac aaa aca gtg ccc cct cag gac agg agg aaa cac agc      829
Asp Leu Glu Tyr Lys Thr Val Pro Pro Gln Asp Arg Arg Lys His Ser
             240                 245                 250 agc agc agc agt gcc ggt ggt gga gga gga aaa tca tca gtg acc ggg      877
Ser Ser Ser Ser Ala Gly Gly Gly Gly Gly Lys Ser Ser Val Thr Gly
             255                 260                 265 atg tct cct gac cag gtg ctc ctc ctg ctc cag ggt gcc gag ccc cca      925
Met Ser Pro Asp Gln Val Leu Leu Leu Leu Gln Gly Ala Glu Pro Pro
 270                 275                 280 atg ctg tgc tcc cgt cag aag ctg agc cga ccg tac acc gag gtc acc      973
Met Leu Cys Ser Arg Gln Lys Leu Ser Arg Pro Tyr Thr Glu Val Thr
285                 290                 295                 300 ata atg aca cta ctc acc agc atg gcc gat aag gag ctg gtc cac atg      1021
Ile Met Thr Leu Leu Thr Ser Met Ala Asp Lys Glu Leu Val His Met
             305                 310                 315 atc acc tgg gcc aag aag ctt cca ggt ttc ctg cag ctg tct ctc cat      1069
```

```
               Ile Thr Trp Ala Lys Lys Leu Pro Gly Phe Leu Gln Leu Ser Leu His
                       320                 325                 330 gac cag gtg cag ctg ctg gag agc tcg tgg ctg gag gtg ctg atg att                 1117
Asp Gln Val Gln Leu Leu Glu Ser Ser Trp Leu Glu Val Leu Met Ile
            335                 340                 345 ggg ctc ata tgg agg tcc atc cac tgc ccc ggc aaa ctc atc ttc gca                 1165
Gly Leu Ile Trp Arg Ser Ile His Cys Pro Gly Lys Leu Ile Phe Ala
350                 355                 360 cag gac ctc ata ctg gac agg aat gaa ggt gac tgt gtg gaa ggc ttt                 1213
Gln Asp Leu Ile Leu Asp Arg Asn Glu Gly Asp Cys Val Glu Gly Phe
365                 370                 375                 380 gtt gag atc ttc gac atg ctg ctg gcc act gcc tcc cgc ttc cgc atg                 1261
Val Glu Ile Phe Asp Met Leu Leu Ala Thr Ala Ser Arg Phe Arg Met
                385                 390                 395 ctc aaa ctc aaa cct gag gag ttt gtc tgc ctc aaa gct atc atc ctg                 1309
Leu Lys Leu Lys Pro Glu Glu Phe Val Cys Leu Lys Ala Ile Ile Leu
            400                 405                 410 ctc aac tct ggt gcc ttc tct ttc tgc acc ggc aca atg gag ccc ctc                 1357
Leu Asn Ser Gly Ala Phe Ser Phe Cys Thr Gly Thr Met Glu Pro Leu
        415                 420                 425 cac aac agc atg gca gtg cag aac atg ctg gac acc atc aca gac gct                 1405
His Asn Ser Met Ala Val Gln Asn Met Leu Asp Thr Ile Thr Asp Ala
    430                 435                 440 ctc ata cat cat atc agc caa tca gga tgc tcg gct cag cag cag tcg                 1453
Leu Ile His His Ile Ser Gln Ser Gly Cys Ser Ala Gln Gln Gln Ser
445                 450                 455                 460 agg cgg cag gcc cag ctg ctg ctc ctg ctc tcc cac atc agg cac atg                 1501
Arg Arg Gln Ala Gln Leu Leu Leu Leu Leu Ser His Ile Arg His Met
                465                 470                 475 agc aac aaa ggc atg gag cat ctc tac agc atg aag tgc aag aac aaa                 1549
Ser Asn Lys Gly Met Glu His Leu Tyr Ser Met Lys Cys Lys Asn Lys
            480                 485                 490 gtg cct ctt tac gac ctt ctg ctg gag atg ttg gac gct cac cgt ata                 1597
Val Pro Leu Tyr Asp Leu Leu Leu Glu Met Leu Asp Ala His Arg Ile
        495                 500                 505 cac cgc cca gac aga cca gct cag ttc tgg tcc cag gct gac gga gag                 1645
His Arg Pro Asp Arg Pro Ala Gln Phe Trp Ser Gln Ala Asp Gly Glu
    510                 515                 520 cct ccc ttc att aac aac aac aac agc agc aac agt ggc agc aat ggc                 1693
Pro Pro Phe Ile Asn Asn Asn Asn Ser Ser Asn Ser Gly Ser Asn Gly
525                 530                 535                 540 ggc gtc tcc tct tca gtc ggt tcc agt tca gga ccc cga gtc aac cac                 1741
Gly Val Ser Ser Ser Val Gly Ser Ser Ser Gly Pro Arg Val Asn His
                545                 550                 555 gag agc ccg agc aga gga ccc aca ggt cca gga gtc ctg cag tac gga                 1789
Glu Ser Pro Ser Arg Gly Pro Thr Gly Pro Gly Val Leu Gln Tyr Gly
            560                 565                 570 ggg tcc cgc tct gac tgc acc cac atc cta tga gg                                  1824
Gly Ser Arg Ser Asp Cys Thr His Ile Leu
        575                 580

<210> SEQ ID NO 6
<211> LENGTH: 30
<212> TYPE: DNA
<213> ORGANISM: Artificial Sequence
<220> FEATURE:
<223> OTHER INFORMATION: Designed oligonucleotide primer for PCR

<400> SEQUENCE: 6
cccagcgcag agcagacagc cttgtggaac                                                 30
```

<210> SEQ ID NO 7
<211> LENGTH: 31
<212> TYPE: DNA
<213> ORGANISM: Artificial Sequence
<220> FEATURE:
<223> OTHER INFORMATION: Designed oligonucleotide primer for PCR

<400> SEQUENCE: 7
cttttgacct tcagatgttt gttgtgctcgg                              31

<210> SEQ ID NO 8
<211> LENGTH: 27
<212> TYPE: DNA
<213> ORGANISM: Artificial Sequence
<220> FEATURE:
<223> OTHER INFORMATION: Designed oligonucleotide primer for PCR

<400> SEQUENCE: 8
aggagcatcc aaggtcacaa tgactac                                  27

<210> SEQ ID NO 9
<211> LENGTH: 28
<212> TYPE: DNA
<213> ORGANISM: Artificial Sequence
<220> FEATURE:
<223> OTHER INFORMATION: Designed oligonucleotide primer for PCR

<400> SEQUENCE: 9
caggtcgtac agaggcactt tgttcttg                                 28

<210> SEQ ID NO 10
<211> LENGTH: 24
<212> TYPE: DNA
<213> ORGANISM: Artificial Sequence
<220> FEATURE:
<223> OTHER INFORMATION: Designed oligonucleotide primer for PCR

<400> SEQUENCE: 10
tctggctact actctgtacc tctg                                     24

<210> SEQ ID NO 11
<211> LENGTH: 24
<212> TYPE: DNA
<213> ORGANISM: Artificial Sequence
<220> FEATURE:
<223> OTHER INFORMATION: Designed oligonucleotide primer for PCR

<400> SEQUENCE: 11
ccccacacta taggactcat catc                                     24

<210> SEQ ID NO 12
<211> LENGTH: 62
<212> TYPE: DNA
<213> ORGANISM: Blue Gill

<400> SEQUENCE: 12
atgagtctga aagactggtt attaggaaaa gaaaggacgg tggtgaccat ggaggagctg    60
ag                                                                  62

<210> SEQ ID NO 13
<211> LENGTH: 24
<212> TYPE: DNA
<213> ORGANISM: Artificial Sequence
<220> FEATURE:
<223> OTHER INFORMATION: Designed oligonucleotide primer for PCR

```
<400> SEQUENCE: 13
gagcagacag ccttgtggaa cagt                                          24

<210> SEQ ID NO 14
<211> LENGTH: 39
<212> TYPE: DNA
<213> ORGANISM: Artificial Sequence
<220> FEATURE:
<223> OTHER INFORMATION: Designed oligonucleotide primer for PCR

<400> SEQUENCE: 14
gcctctagac caccatgagt ctgaaagact ggttattag                          39

<210> SEQ ID NO 15
<211> LENGTH: 39
<212> TYPE: DNA
<213> ORGANISM: Artificial Sequence
<220> FEATURE:
<223> OTHER INFORMATION: Designed oligonucleotide primer for PCR

<400> SEQUENCE: 15
gcctctagag ttgtgctcgg cctcatagga tgtgggtgc                          39

<210> SEQ ID NO 16
<211> LENGTH: 38
<212> TYPE: DNA
<213> ORGANISM: Artificial Sequence
<220> FEATURE:
<223> OTHER INFORMATION: Designed oligonucleotide primer for PCR

<400> SEQUENCE: 16
ggcaagcttc caccatgtac cctgaagaga gcaggggg                           38

<210> SEQ ID NO 17
<211> LENGTH: 52
<212> TYPE: DNA
<213> ORGANISM: Artificial Sequence
<220> FEATURE:
<223> OTHER INFORMATION: Designed oligonucleotide for synthesis of
      promoter DNA

<400> SEQUENCE: 17
gatctcgact ataaagaggg caggctgtcc tctaagcgtc accacgactt ca           52

<210> SEQ ID NO 18
<211> LENGTH: 52
<212> TYPE: DNA
<213> ORGANISM: Artificial Sequence
<220> FEATURE:
<223> OTHER INFORMATION: Designed oligonucleotide for synthesis of
      promoter DNA

<400> SEQUENCE: 18
agcttgaagt cgtggtgacg cttagaggac agcctgccct ctttatagtc ga           52

<210> SEQ ID NO 19
<211> LENGTH: 34
<212> TYPE: DNA
<213> ORGANISM: Artificial Sequence
<220> FEATURE:
<223> OTHER INFORMATION: Designed oligonucleotide primer for PCR

<400> SEQUENCE: 19
ggccgaattc ggcatgatga aggaggtgt tcgc                                34
```

<210> SEQ ID NO 20
<211> LENGTH: 34
<212> TYPE: DNA
<213> ORGANISM: Artificial Sequence
<220> FEATURE:
<223> OTHER INFORMATION: Designed oligonucleotide primer for PCR

<400> SEQUENCE: 20
ggccgtcgac gtgctcggcc tcataggatg tggg                                34

<210> SEQ ID NO 21
<211> LENGTH: 33
<212> TYPE: DNA
<213> ORGANISM: Artificial Sequence
<220> FEATURE:
<223> OTHER INFORMATION: Designed oligonucleotide primer for PCR

<400> SEQUENCE: 21
gccgaattcg agagagctga cgggcagagc aga                                 33

<210> SEQ ID NO 22
<211> LENGTH: 33
<212> TYPE: DNA
<213> ORGANISM: Artificial Sequence
<220> FEATURE:
<223> OTHER INFORMATION: Designed oligonucleotide primer for PCR

<400> SEQUENCE: 22
gccagatctg ctcatagttg ctggcatacc act                                 33

<210> SEQ ID NO 23
<211> LENGTH: 554
<212> TYPE: PRT
<213> ORGANISM: Blue gill

<400> SEQUENCE: 23

Met Ala Cys Ser Pro Glu Lys Asp Gln Pro Leu Leu Gln Leu Gln Lys
 1               5                  10                  15

Val Asp Ser Ser Arg Val Gly Ser Arg Val Val Ser Pro Ile Leu Asn
            20                  25                  30

Ser Pro Leu Glu Arg Ser Gln Pro Ile Cys Ile Pro Ser Pro Tyr Thr
        35                  40                  45

Asp Leu Ser His Asp Phe Thr Thr Ile Pro Phe Tyr Ser Pro Thr Phe
    50                  55                  60

Phe Ser Tyr Ala Ser Pro Gly Ile Ser Asp Cys Pro Ser Val His Gln
65                  70                  75                  80

Ser Leu Ser Pro Ser Leu Phe Trp Pro Ser His Gly His Val Gly Ser
                85                  90                  95

Pro Ile Pro Leu His His Ser Gln Pro Arg Pro Gln His Arg Gln Pro
            100                 105                 110

Ile Gln Ser Pro Trp Val Glu Leu Ser Pro Leu Glu Ser Thr Leu Thr
        115                 120                 125

Thr Ser Lys Ser Val Arg Arg Arg Ser Gln Glu Ser Glu Asp Gly Val
    130                 135                 140

Val Ser Gly Gly Lys Ala Asp Ile His Tyr Cys Ala Val Cys His
145                 150                 155                 160

Asp Tyr Ala Ser Gly Tyr His Tyr Gly Val Trp Ser Cys Glu Gly Cys
                165                 170                 175

Lys Ala Phe Phe Lys Arg Ser Ile Gln Arg His Asn Asp Tyr Ile Cys
            180                 185                 190

```
Pro Ala Thr Asn Gln Cys Thr Ile Asp Lys Asn Arg Arg Lys Ser Cys
        195                 200                 205

Gln Ala Cys Arg Leu Arg Lys Cys Asn Glu Val Gly Met Thr Lys Cys
    210                 215                 220

Gly Val Arg Lys Glu Arg Gly Asn Cys Arg Asn Pro Gln Met Arg Arg
225                 230                 235                 240

Val Thr Arg Leu Ser Thr Gln Gly Arg Thr Asn Arg Thr Ala Val Leu
                245                 250                 255

Thr Gly Pro Ala Val Gly Ser Leu Ile Ser Leu Asn Ser Pro Ala Leu
            260                 265                 270

Thr Pro Glu Gln Leu Ile Glu Arg Ile Ile Asp Ala Glu Pro Pro Glu
        275                 280                 285

Ile Tyr Leu Met Lys Asp Met Arg Arg Pro Leu Thr Glu Ala Asn Val
    290                 295                 300

Met Met Ser Leu Thr Asn Leu Ala Asp Lys Glu Leu Val His Met Ile
305                 310                 315                 320

Ser Trp Ala Lys Lys Ile Pro Gly Phe Val Glu Leu Ser Leu Leu Asp
                325                 330                 335

Gln Val His Leu Leu Glu Cys Cys Trp Leu Glu Val Leu Met Val Gly
            340                 345                 350

Leu Met Trp Arg Ser Val Asp His Pro Gly Lys Leu Ile Phe Ser Arg
        355                 360                 365

Asp Leu Ser Leu Ser Arg Glu Glu Gly Ser Cys Val Gln Gly Phe Ala
    370                 375                 380

Glu Ile Phe Asp Met Leu Ile Ala Ala Thr Ser Arg Val Arg Glu Leu
385                 390                 395                 400

Lys Leu Gln Arg Glu Glu Tyr Val Cys Leu Lys Ala Met Ile Leu Leu
                405                 410                 415

Asn Ser Asn Met Cys Leu Gly Ser Ser Glu Gly Ser Glu Glu Leu Gln
            420                 425                 430

Ser Arg Ser Lys Leu Leu Cys Leu Leu Asp Ala Val Thr Asp Ala Leu
        435                 440                 445

Val Trp Ala Ile Ala Lys Thr Gly Leu Thr Phe Arg Gln Gln Tyr Thr
    450                 455                 460

Arg Leu Ala His Leu Leu Met Leu Leu Ser His Ile Arg His Val Ser
465                 470                 475                 480

Asn Lys Gly Met Asp His Leu His Cys Met Lys Met Lys Asn Met Val
                485                 490                 495

Pro Leu Tyr Asp Leu Leu Leu Glu Met Leu Asp Ala His Ile Met His
            500                 505                 510

Ser Ser Arg Leu Ser His Gln Pro Ile Gln Gln Asp Ala Gln Asp Gln
        515                 520                 525

Arg Glu Ala Pro Ala Arg Pro His Ser Cys Gly Ser Gly Pro Leu Asn
    530                 535                 540

Thr Trp Thr Pro Gly Gly Gly Glu Arg Gln
545                 550

<210> SEQ ID NO 24
<211> LENGTH: 2186
<212> TYPE: DNA
<213> ORGANISM: Blue gill
<220> FEATURE:
<221> NAME/KEY: CDS
<222> LOCATION: (106)...(1770)
```

<400> SEQUENCE: 24

```
cttacactga cactcggaga aaaagatgac taatgacatc ctaggcccat attctttgtc       60
gacgatgtgg tagatctagt gatactgaga cagtcagtag ttgca atg gcc tgc tct      117
                                                 Met Ala Cys Ser
                                                   1 cca gag aag gat cag ccc ctc ctc cag ctc cag aag gtg gac tcc agt        165
Pro Glu Lys Asp Gln Pro Leu Leu Gln Leu Gln Lys Val Asp Ser Ser
  5              10                  15                  20 cga gtt ggc agt cgt gtc gtc tcc ccg atc ctc aac tcc ccg ttg gaa        213
Arg Val Gly Ser Arg Val Val Ser Pro Ile Leu Asn Ser Pro Leu Glu
             25                  30                  35 aga agc cag ccc atc tgc atc ccc tcc cct tac acc gac ctc agc cac        261
Arg Ser Gln Pro Ile Cys Ile Pro Ser Pro Tyr Thr Asp Leu Ser His
         40                  45                  50 gac ttc acc acc ata cct ttc tac agt cca act ttc ttt agt tat gcc        309
Asp Phe Thr Thr Ile Pro Phe Tyr Ser Pro Thr Phe Phe Ser Tyr Ala
     55                  60                  65 agt cca ggc att tca gac tgc ccc tcc gtc cat cag tca cta agc ccc        357
Ser Pro Gly Ile Ser Asp Cys Pro Ser Val His Gln Ser Leu Ser Pro
 70                  75                  80 tcc tta ttc tgg ccc agc cat ggc cat gtt ggg tcc ccc ata ccc ctg        405
Ser Leu Phe Trp Pro Ser His Gly His Val Gly Ser Pro Ile Pro Leu
 85                  90                  95                 100 cac cac tcc cag cct cga cct cag cac aga cag cca atc cag agt cca        453
His His Ser Gln Pro Arg Pro Gln His Arg Gln Pro Ile Gln Ser Pro
                105                 110                 115 tgg gtg gag ttg tca cca ctg gag agc acc tta aca acc agt aag agt        501
Trp Val Glu Leu Ser Pro Leu Glu Ser Thr Leu Thr Thr Ser Lys Ser
            120                 125                 130 gta agg agg cgt tct cag gag agc gag gat ggc gtg gtg tcg tcc ggc        549
Val Arg Arg Arg Ser Gln Glu Ser Glu Asp Gly Val Val Ser Ser Gly
        135                 140                 145 ggg aag gcg gac atc cac tac tgc gct gtg tgt cac gac tac gcc tca        597
Gly Lys Ala Asp Ile His Tyr Cys Ala Val Cys His Asp Tyr Ala Ser
    150                 155                 160 gga tac cac tac ggc gtc tgg tca tgt gag ggg tgt aag gcc ttc ttc        645
Gly Tyr His Tyr Gly Val Trp Ser Cys Glu Gly Cys Lys Ala Phe Phe
165                 170                 175                 180 aag agg agc atc caa aga cac aat gac tac atc tgc cca gca acc aat        693
Lys Arg Ser Ile Gln Arg His Asn Asp Tyr Ile Cys Pro Ala Thr Asn
                185                 190                 195 caa tgc act ata gac aag aac cgc gtt aag agc tgc cag gcg tgc cgc        741
Gln Cys Thr Ile Asp Lys Asn Arg Val Lys Ser Cys Gln Ala Cys Arg
            200                 205                 210 ctt cgc aaa tgc aat gaa gtt ggc atg acc aag tgt ggt gtg aga aag        789
Leu Arg Lys Cys Asn Glu Val Gly Met Thr Lys Cys Gly Val Arg Lys
        215                 220                 225 gag cgt ggg aac tgc aga aac ccc cag atg agg cga gtg acc cga ctc        837
Glu Arg Gly Asn Cys Arg Asn Pro Gln Met Arg Arg Val Thr Arg Leu
    230                 235                 240 tcc aca cag ggc aga act aac aga aca gct gtg tta act gga cca gcc        885
Ser Thr Gln Gly Arg Thr Asn Arg Thr Ala Val Leu Thr Gly Pro Ala
245                 250                 255                 260 gtg ggt tca cta atc tcg ctc aac tct cct gca ctg acc cca gag cag        933
Val Gly Ser Leu Ile Ser Leu Asn Ser Pro Ala Leu Thr Pro Glu Gln
                265                 270                 275 ctg att gaa cga ata att gat gct gag cca cca gag atc tac ctc atg        981
Leu Ile Glu Arg Ile Ile Asp Ala Glu Pro Pro Glu Ile Tyr Leu Met
            280                 285                 290
```

```
aaa gac atg agg agg cct ctg act gaa gca aac gtc atg atg tcg ctc    1029
Lys Asp Met Arg Arg Pro Leu Thr Glu Ala Asn Val Met Met Ser Leu
        295                 300                 305 aca aac ctt gct gat aag gag ctg gtt cac atg atc agc tgg gcc aag    1077
Thr Asn Leu Ala Asp Lys Glu Leu Val His Met Ile Ser Trp Ala Lys
    310                 315                 320 aag att cca ggg ttt gta gag ctc agt ctc ttg gac cag gtg cac ctg    1125
Lys Ile Pro Gly Phe Val Glu Leu Ser Leu Leu Asp Gln Val His Leu
325                 330                 335                 340 ttg gag tgc tgc tgg ctg gag gtg ctg atg gtt gga ctg atg tgg agg    1173
Leu Glu Cys Cys Trp Leu Glu Val Leu Met Val Gly Leu Met Trp Arg
                345                 350                 355 tca gtg gac cat cct ggg aaa ctt atc ttc tcc cgg gac ctc agc ctg    1221
Ser Val Asp His Pro Gly Lys Leu Ile Phe Ser Arg Asp Leu Ser Leu
            360                 365                 370 agc aga gaa gag ggg agc tgt gtc cag ggc ttc gca gag atc ttt gat    1269
Ser Arg Glu Glu Gly Ser Cys Val Gln Gly Phe Ala Glu Ile Phe Asp
        375                 380                 385 atg ctg ata gct gcc acg tcc agg gtg aga gag ctc aag ctc cag agg    1317
Met Leu Ile Ala Ala Thr Ser Arg Val Arg Glu Leu Lys Leu Gln Arg
    390                 395                 400 gag gag tac gtc tgc ctc aag gcc atg atc ctc ctt aac tcc aac atg    1365
Glu Glu Tyr Val Cys Leu Lys Ala Met Ile Leu Leu Asn Ser Asn Met
405                 410                 415                 420 tgc ctc ggc tcc tca gag ggc agc gag gag ctg cag agt cgc tcc aag    1413
Cys Leu Gly Ser Ser Glu Gly Ser Glu Glu Leu Gln Ser Arg Ser Lys
                425                 430                 435 ctg ctg tgt ctt ctg gac gct gta acg gac gct ctg gtg tgg gcc atc    1461
Leu Leu Cys Leu Leu Asp Ala Val Thr Asp Ala Leu Val Trp Ala Ile
            440                 445                 450 gcc aaa act ggc ctc act ttc cgc caa cag tac acc cgc ctc gcc cac    1509
Ala Lys Thr Gly Leu Thr Phe Arg Gln Gln Tyr Thr Arg Leu Ala His
        455                 460                 465 ctg ctt atg ctg ctc tca cac atc cgc cat gtc agt aac aaa ggc atg    1557
Leu Leu Met Leu Leu Ser His Ile Arg His Val Ser Asn Lys Gly Met
    470                 475                 480 gac cac ctc cac tgc atg aaa atg aag aac atg gtg cct ttg tat gac    1605
Asp His Leu His Cys Met Lys Met Lys Asn Met Val Pro Leu Tyr Asp
485                 490                 495                 500 ctg ctg ctg gag atg ttg gat gcc cac atc atg cac agc tcc cgt ctg    1653
Leu Leu Leu Glu Met Leu Asp Ala His Ile MET His Ser Ser Arg Leu
                505                 510                 515 tct cac cag ccc ata cag caa gac gca cag gac cag agg gag gct cct    1701
Ser His Gln Pro Ile Gln Gln Asp Ala Gln Asp Gln Arg Glu Ala Pro
            520                 525                 530 gct cgg cca cac agc tgt gga agc ggc cct tta aac acc tgg aca cca    1749
Ala Arg Pro His Ser Cys Gly Ser Gly Pro Leu Asn Thr Trp Thr Pro
        535                 540                 545 ggt gga ggt gaa cgg cag tag tctgatggaa tgaattttca ccgctttgca caaa    1804
Gly Gly Gly Glu Arg Gln
    550 actacttcac aaaactgatg agatgtttca cttgaacatt cttcagcacg ctaaattctg    1864 tgaaactcga gctttgacac actgtgcact acttatattg aacttttttg aatatctaaa    1924 gtttttcatt tgttattcat tgccttacca ccacatattg aaaagccagc aaacagatta    1984 agcagttgct gttataattg ggccagtagc acaattagtt gctcatatgt tcaggtaata    2044 tgttactgcc gtgaatctcc tgggtcgagc agctaatttc ctatcaaata acattgataa    2104
```

```
ataacattgt gtggtaagga gagacagtat ggtttcacct gtcacagtaa cacctgaggc   2164
agatcctgag atggtgttac ct                                           2186

<210> SEQ ID NO 25
<211> LENGTH: 963
<212> TYPE: DNA
<213> ORGANISM: Blue gill

<400> SEQUENCE: 25
aggagcatcc aaggtcacaa tgactacatc tgcccagcaa ccaatcaatg cactatagac     60
aagaaccgcc gtaagagctg ccaggcgtgc cgccttcgca aatgcaatga agttggcatg    120
accaagtgtg gtgtgagaaa ggagcgtggg aactgcagaa accccagat gaggcgagtg    180 acccgactct ccacacaggg cagaactaac agaacagctg tgttaactgg accagccgtg    240
ggttcactaa tctcgctcaa ctctcctgca ctgaccccag agcagctgat tgaacgaata    300
attgatgctg agccaccaga gatctacctc atgaaagaca tgaggaggcc tctgactgaa    360
gcaaacgtca tgatgtcgct cacaaacctt gctgataagg agctggttca catgatcagc    420
tgggccaaga agattccagg gtttgtagag ctcagtctct tggaccaggt gcacctgttg    480
gagtgctgct ggctggaggt gctgatggtt ggactgatgt ggaggtcagt ggaccatcct    540
gggaaactta tcttctcccg ggacctcagc ctgagcagag aagaggggag ctgtgtccag    600
ggcttcgcag agatctttga tatgctgata gctgccacgt ccagggtgag agagctcaag    660
ctccagaggg aggagtacgt ctgcctcaag gccatgatcc tccttaactc aacatgtgc    720 ctcggctcct cagagggcag cgaggagctg cagagtcgct ccaagctgct gtgtcttctg    780
gacgctgtaa cggacgctct ggtgtgggcc atcgccaaaa ctggcctcac tttccgccaa    840
cagtacaccc gcctcgccca cctgcttatg ctgctctcac acatccgcca tgtcagtaac    900
aaaggcatgg accacctcca ctgcatgaaa atgaacaaga acaaagtgcc tctgtacgac    960
ctg                                                                  963

<210> SEQ ID NO 26
<211> LENGTH: 25
<212> TYPE: DNA
<213> ORGANISM: Artificial Sequence
<220> FEATURE:
<223> OTHER INFORMATION: Designed oligonucleotide primer for PCR

<400> SEQUENCE: 26
gatactgaga cagtcagtag ttgca                                           25

<210> SEQ ID NO 27
<211> LENGTH: 26
<212> TYPE: DNA
<213> ORGANISM: Artificial Sequence
<220> FEATURE:
<223> OTHER INFORMATION: Designed oligonucleotide primer for PCR

<400> SEQUENCE: 27
tgcaaagcgg tgaaaattca ttccat                                          26

<210> SEQ ID NO 28
<211> LENGTH: 27
<212> TYPE: DNA
<213> ORGANISM: Artificial Sequence
<220> FEATURE:
<223> OTHER INFORMATION: Designed oligonucleotide primer for PCR

<400> SEQUENCE: 28
```
aggagcatcc aaggtcacaa tgactac                                              27

<210> SEQ ID NO 29
<211> LENGTH: 28
<212> TYPE: DNA
<213> ORGANISM: Artificial Sequence
<220> FEATURE:
<223> OTHER INFORMATION: Designed oligonucleotide primer for PCR

<400> SEQUENCE: 29
caggtcgtac agaggcactt tgttcttg                                             28

<210> SEQ ID NO 30
<211> LENGTH: 28
<212> TYPE: DNA
<213> ORGANISM: Artificial Sequence
<220> FEATURE:
<223> OTHER INFORMATION: Designed oligonucleotide primer for PCR

<400> SEQUENCE: 30
ctaggcccat attctttgtc gacgatgt                                             28

<210> SEQ ID NO 31
<211> LENGTH: 27
<212> TYPE: DNA
<213> ORGANISM: Artificial Sequence
<220> FEATURE:
<223> OTHER INFORMATION: Designed oligonucleotide primer for PCR

<400> SEQUENCE: 31
ataagtagtg cacagtgtgt caaagct                                              27

<210> SEQ ID NO 32
<211> LENGTH: 52
<212> TYPE: DNA
<213> ORGANISM: Artificial Sequence
<220> FEATURE:
<223> OTHER INFORMATION: Designed oligonucleotide to synthesize
      promoter DNA

<400> SEQUENCE: 32
gatctcgact ataaagaggg caggctgtcc tctaagcgtc accacgactt ca                  52

<210> SEQ ID NO 33
<211> LENGTH: 52
<212> TYPE: DNA
<213> ORGANISM: Artificial Sequence
<220> FEATURE:
<223> OTHER INFORMATION: Designed oligonucleotide to synthesize
      promoter DNA

<400> SEQUENCE: 33
agcttgaagt cgtggtgacg cttagaggac agcctgccct ctttatagtc ga                  52

<210> SEQ ID NO 34
<211> LENGTH: 27
<212> TYPE: DNA
<213> ORGANISM: Artificial Sequence
<220> FEATURE:
<223> OTHER INFORMATION: Designed oligonucleotide pr
      imer for PCR

<400> SEQUENCE: 34
gccgaattcg gcatgaccaa gtgtggt                                              27

<210> SEQ ID NO 35

```
<211> LENGTH: 30
<212> TYPE: DNA
<213> ORGANISM: Artificial Sequence
<220> FEATURE:
<223> OTHER INFORMATION: Designed oligonucleotide primer for PCR

<400> SEQUENCE: 35
ccggtcgacc tactgccgtt cacctccacc                                          30

<210> SEQ ID NO 36
<211> LENGTH: 33
<212> TYPE: DNA
<213> ORGANISM: Artificial Sequence
<220> FEATURE:
<223> OTHER INFORMATION: Designed oligonucleotide primer for PCR

<400> SEQUENCE: 36
gccgaattcg agagagctga cgggcagagc aga                                      33

<210> SEQ ID NO 37
<211> LENGTH: 33
<212> TYPE: DNA
<213> ORGANISM: Artificial Sequence
<220> FEATURE:
<223> OTHER INFORMATION: Designed oligonucleotide primer for PCR

<400> SEQUENCE: 37
gccagatctg ctcatagttg ctggcatacc act                                      33

<210> SEQ ID NO 38
<211> LENGTH: 25
<212> TYPE: DNA
<213> ORGANISM: Artificial Sequence
<220> FEATURE:
<223> OTHER INFORMATION: Designed oligonucleotide primer for PCR

<400> SEQUENCE: 38
agagtcgggt cactcgcctc atctg                                               25

<210> SEQ ID NO 39
<211> LENGTH: 25
<212> TYPE: DNA
<213> ORGANISM: Artificial Sequence
<220> FEATURE:
<223> OTHER INFORMATION: Designed oligonucleotide primer for PCR

<400> SEQUENCE: 39
gtctatagtg cattgattgg ttgct                                               25

<210> SEQ ID NO 40
<211> LENGTH: 20
<212> TYPE: DNA
<213> ORGANISM: Artificial Sequence
<220> FEATURE:
<223> OTHER INFORMATION: Designed oligonucleotide primer for PCR

<400> SEQUENCE: 40
tgacacacag cgcagtagtg                                                     20

<210> SEQ ID NO 41
<211> LENGTH: 494
<212> TYPE: DNA
<213> ORGANISM: Blue gill

<400> SEQUENCE: 41
gtcgacgatg tggtagatct agtgatactg agacagtcag tagttgcaat ggcctgctct         60
```

```
ccagagaagg atcagcccct cctccagctc cagaaggtgg actccagtcg agttggcagt        120
cgtgtcgtct ccccgatcct caactcccog ttggaagaag ccagcccatc tgcatccoct        180 cccttacac cgacctcagc cacgacttca ccaccatacc tttctacagt ccaactttct         240
ttagttatgc cagtccaggc atttcagact gcccctccgt ccatcagtca ctaagcccct        300
ccttattctg gcccagccat ggccatgttg gtcccccat accctgcac cactcccagc          360 ctcgacctca gcacagacag ccaatccaga gtccatgggt ggagttgtca ccactggaga       420
gcaccttaac aaccagtaag agtgtaagga ggcgttctca ggagagcgag gatggcgtgg       480
tgtcgtccgg cggg                                                          494

<210> SEQ ID NO 42
<211> LENGTH: 22
<212> TYPE: DNA
<213> ORGANISM: Artificial Sequence
<220> FEATURE:
<223> OTHER INFORMATION: Designed oligonucleotide primer for PCR

<400> SEQUENCE: 42
gtctgaaatg cctggactgg ca                                                 22

<210> SEQ ID NO 43
<211> LENGTH: 21
<212> TYPE: DNA
<213> ORGANISM: Artificial Sequence
<220> FEATURE:
<223> OTHER INFORMATION: Designed oligonucleotide primer for PCR

<400> SEQUENCE: 43
actggagtcc accttctgga g                                                  21

<210> SEQ ID NO 44
<211> LENGTH: 139
<212> TYPE: DNA
<213> ORGANISM: Blue gill

<400> SEQUENCE: 44
cttacactga cactcggaga aaaagatgac taatgacatc ctaggcccat attctttgtc        60
gacgatgtgg tagatctagt gatactgaga cagtcagtag ttgcaatggc ctgctctcca       120
gagaaggatc agcccctcc                                                    139

<210> SEQ ID NO 45
<211> LENGTH: 20
<212> TYPE: DNA
<213> ORGANISM: Artificial Sequence
<220> FEATURE:
<223> OTHER INFORMATION: Designed oligonucleotide primer for PCR

<400> SEQUENCE: 45
cttacactga cactcggaga                                                    20

<210> SEQ ID NO 46
<211> LENGTH: 21
<212> TYPE: DNA
<213> ORGANISM: Artificial Sequence
<220> FEATURE:
<223> OTHER INFORMATION: Designed oligonucleotide primer for PCR

<400> SEQUENCE: 46
ctactgccgt tcacctccac c                                                  21
```

```
<210> SEQ ID NO 47
<211> LENGTH: 39
<212> TYPE: DNA
<213> ORGANISM: Artificial Sequence
<220> FEATURE:
<223> OTHER INFORMATION: Designed oligonucleotide primer for PCR

<400> SEQUENCE: 47
cggaagcttc caccatggcc tgctctccag agaaggatc                              39

<210> SEQ ID NO 48
<211> LENGTH: 33
<212> TYPE: DNA
<213> ORGANISM: Artificial Sequence
<220> FEATURE:
<223> OTHER INFORMATION: Designed oligonucleotide primer for PCR

<400> SEQUENCE: 48
cggtctagac tactgccgtt cacctccacc tgg                                    33
```

1

ESTROGEN RECEPTOR GENES AND UTILIZATION THEREOF

TECHNICAL FIELD

The present invention relates to estrogen receptor genes and the utilization thereof.

BACKGROUND ART

In recent years, some environmental chemical substances have been reported to have estrogen-like activity, and for example, feminization of wild fin has been reported on some types of chemical substances (T. Colborn, D. Dumanoski and J. P. Myers, Our Stolen Future, 1996, Dutton, New York). The activity of such chemical substances leads to a disturbance of hormone balance in various organisms including human and can cause disorders or diseases. Thus, the measurement of the estrogen-like activity of chemical substances has been attempted as part of a safety test for chemical substances.

Estrogen binds to the estrogen receptor in an estrogen target cell so that the receptor is activated to bind to chromosomal estrogen response element sequences. A transcription coupling factor, which recognizes the complex of the estrogen and the estrogen receptor, binds to the estrogen response element sequences to promote the expression of the genes downstream of the sequences. For the method of determining estrogen-like activity of chemical substances, therefore, there has been a need to develop an assay system for evaluating the ability of the chemical substances to regulate the estrogen receptor activity, and there has been a demand for an estrogen receptor gene which is applicable in such an assay system.

DISCLOSURE OF INVENTION

Under the circumstances, the inventor has made active investigations and succeeded in isolating an estrogen receptor gene from a bluegill, a aquatic animal model, to complete the present invention.

Thus, the present invention provides;

1) An estrogen receptor gene comprising a nucleotide sequence coding for any of the following amino acid sequences (a) to (f) (hereinafter, referred to as the inventive gene):
   (a) the amino acid sequence of SEQ ID NO: 1,
   (b) the amino acid sequence of SEQ ID NO: 4,
   (c) the amino acid sequence of SEQ ID NO: 23,
   (d) an amino acid sequence exhibiting 95% or more amino acid identity to the amino acid sequence of SEQ ID NO: 1,
   (e) an amino acid sequence exhibiting 95% or more amino acid identity to the amino acid sequence of SEQ ID NO: 4, and
   (f) an amino acid sequence exhibiting 85% or more amino acid identity to the amino acid sequence of SEQ ID NO: 23;

2) An estrogen receptor gene comprising any of the following nucleotide sequences (g) to (1):
   (g) the nucleotide sequence represented by nucleotide numbers 424 to 1941 of SEQ ID NO: 2,
   (h) the nucleotide sequence represented by nucleotide numbers 74 to 1819 of SEQ ID NO: 5, and
   (1) the nucleotide sequence represented by nucleotide numbers 106 to 1767 of SEQ ID NO: 24:

3) A vector comprising the inventive gene (hereinafter, referred to as the inventive vector);

4) A method for producing a vector, comprising a step of incorporating the inventive gene into a vector replicable in a host cell;

5) A transformant, wherein the inventive gene is introduced into a host cell(hereinafter, referred to as the inventive transformant);

6) A method for producing a transformant, comprising a step of introducing the inventive gene or the inventive vector into a host cell;

7) A method for manufacturing an estrogen receptor, comprising a step of culturing the inventive transformant and a step of producing estrogen receptor;

8) A DNA, comprising a partial nucleotide sequence of the inventive gene;

9) The DNA according to claim 17, wherein said partial nucleotide sequence is a nucleotide sequence coding for a ligand binding domain of the estrogen receptor;

10) An estrogen receptor, comprising any of the following amino acid sequences (a) to (f):
   (a) the amino acid sequence of SEQ ID NO: 1,
   (b) the amino acid sequence of SEQ ID NO: 4,
   (c) the amino acid sequence of SEQ ID NO: 23,
   (d) an amino acid sequence exhibiting 95% or more amino acid identity to the amino acid sequence of SEQ ID NO: 1,
   (e) an amino acid sequence exhibiting 95% or more amino acid identity to the amino acid sequence of SEQ ID NO: 4, and
   (f) an amino acid sequence exhibiting 85% or more amino acid identity to the amino acid sequence of SEQ ID NO: 23;

11) A method for evaluating the ability of a test substance to regulate estrogen receptor activity, comprising a step of:

bringing the test substance into contact with a transformant, wherein a reporter gene linked downstream of a transcriptional control region including an estrogen response element sequence and the inventive gene are introduced into said transformant, and measureing an expression amount of said reporter gene in said transformant;

12) A receptor binding assay, comprising a step of: bringing a test substance into contact with the estrogen receptor according to the above 10 and incubating;

13) Use of the inventive gene for measuring the ability of a test substance to regulate estrogen receptor activity in a two-hybrid system, wherein ligand-dependent formation of a complex comprising:

an estrogen receptor and a transcription coupling factor capable of ligand-dependently binding to the estrogen receptor or receptor binding domain of said transcription coupling factor; results in activation of transcription of a reporter gene;

14) Use of DNA comprising a partial nucleotide sequence of the inventive gene for measuring the ability of a test substance to regulate estrogen receptor activity in a two-hybrid system, wherein ligand-dependent formation of a complex comprising:

an estrogen receptor and a transcription coupling factor capable of ligand-dependently binding to the estrogen receptor or receptor binding domain of said transcription coupling factor; results in activation of transcription of a reporter gene.

BRIEF DESCRIPTION OF DRAWINGS

FIG. 13 is a diagram showing a result of measuring the ability of several test compounds to activate the estrogen receptor activity by the two-hybrid system using the inventive gene, bger α (N=4). Along the abscissa axis, the β-galactosidase activity value is shown, where the β-galactosidase activity value of a section in which 1 nM of E2 was added is normalized as 1.

FIG. 14 is a diagram showing a result of measuring the ability of estradiol to activate the estrogen receptor activity by the reporter assay using the inventive gene, bger β. Along the abscissa axis, the concentration of estradiol are annotated for each experimental section. The left end column indicated by O corresponds to an experimental section in which DMSO was added at a final concentration of 0.1% in place of the DMSO solution of estradiol (estradiol-free section). Along the ordinate axis, the luciferase activity value is shown, where the luciferase activity value of the estradiol-free section is normalized as 1.

BEST MODE FOR CARRYING OUT THE INVENTION

Figure 1:
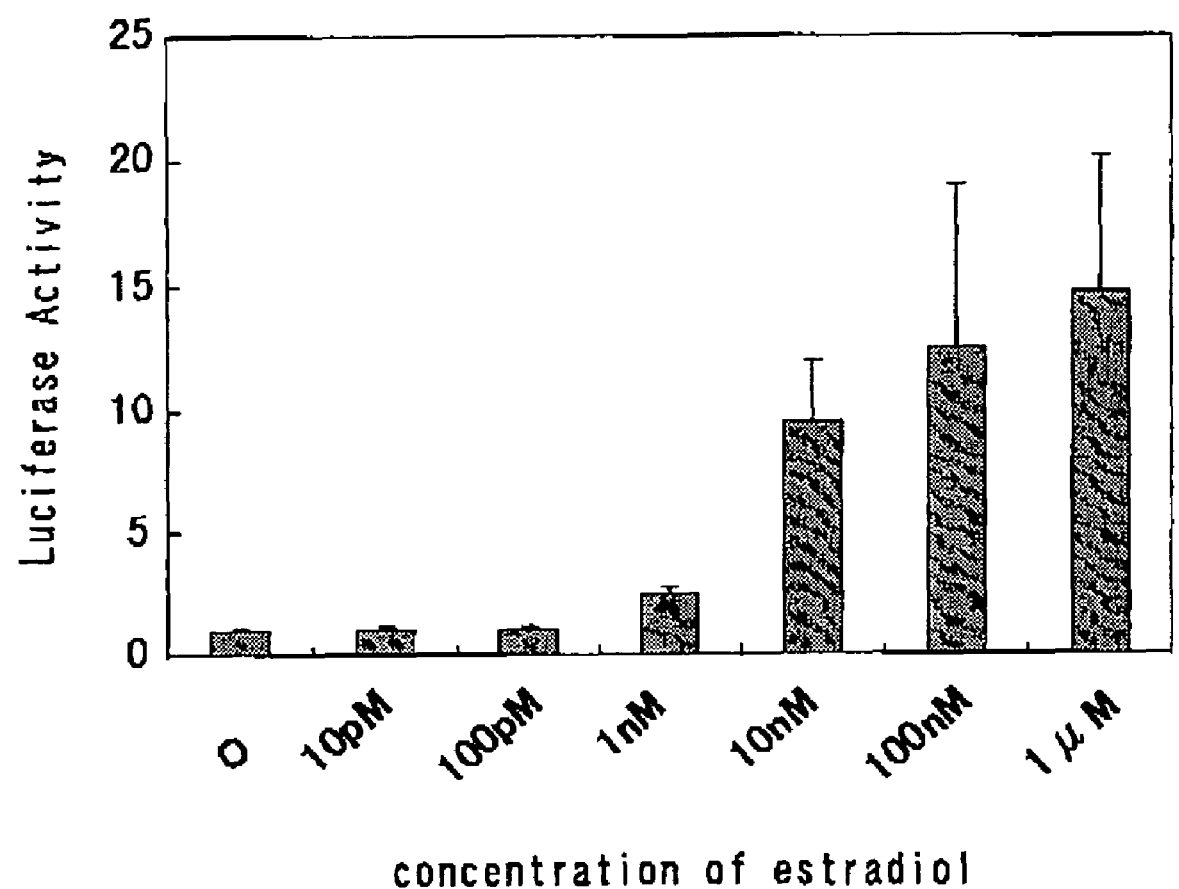
FIG. 1 is a diagram showing a result of measuring the ability of E2 to activate the estrogen receptor activity by the reporter assay using the inventive gene, bger α (N=6). Along the abscissa axis, the concentration of E2 are annotated for each experimental section. The left end column indicated by O corresponds to an experimental section in which DMSO was added at a final concentration of 0.1% in place of the DMSO solution of E2 (E2-free section). Along the ordinate axis, the luciferase activity value is shown, where the luciferase activity value of the E2-free section is normalized as 1.
Figure 2:
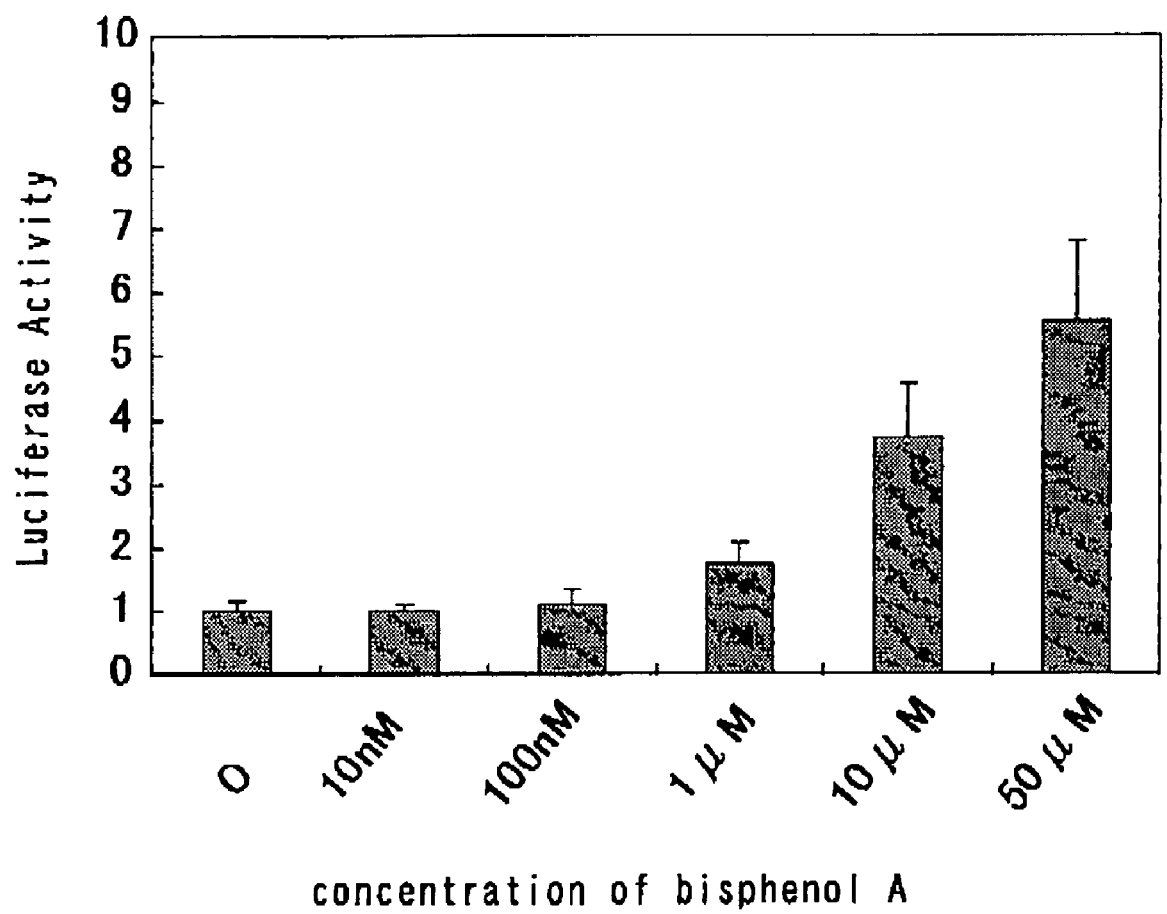
FIG. 2 is a diagram showing a result of measuring the ability of bisphenol A to activate the estrogen receptor activity by the reporter assay using the inventive gene, bger α (N=6). Along the abscissa axis, the concentration of bisphenol A are annotated for each experimental section. The left end column indicated by O corresponds to an experimental section in which DMSO was added at a final concentration of 0.1% in place of the DMSO solution of bisphenol A (bisphenol A-free section). Along the ordinate axis, the luciferase activity value is shown, where the luciferase activity value of the bisphenol A-free section is normalized as 1.
Figure 3:
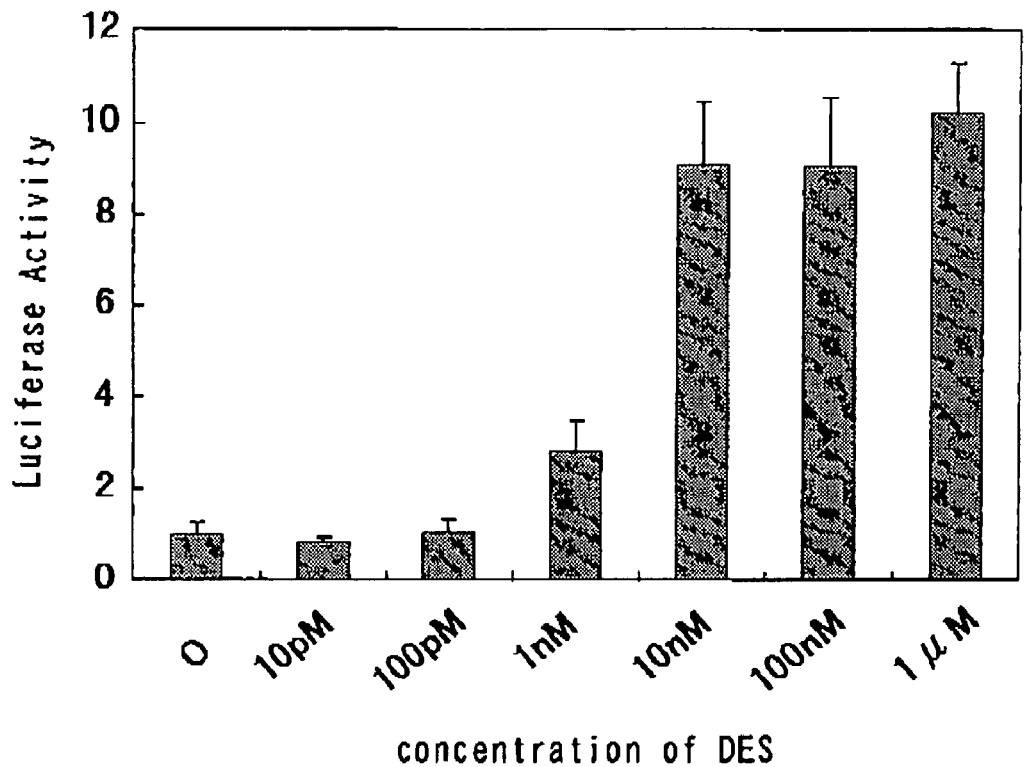
FIG. 3 is a diagram showing a result of measuring the ability of diethylstllbestrol (DES) to activate the estrogen receptor activity by the reporter assay using the inventive gene, bger α (N=6). Along the abscissa axis, the concentration of DES are annotated for each experimental section. The left end column indicated by O corresponds to an experimental section in which DMSO was added at a final concentration of 0.1% in place of the DMSO solution of DES (DES-free section). Along the ordinate axis, the luciferase activity value is shown, where the luciferase activity value of the DES-free section is normalized as 1.
Figure 4:
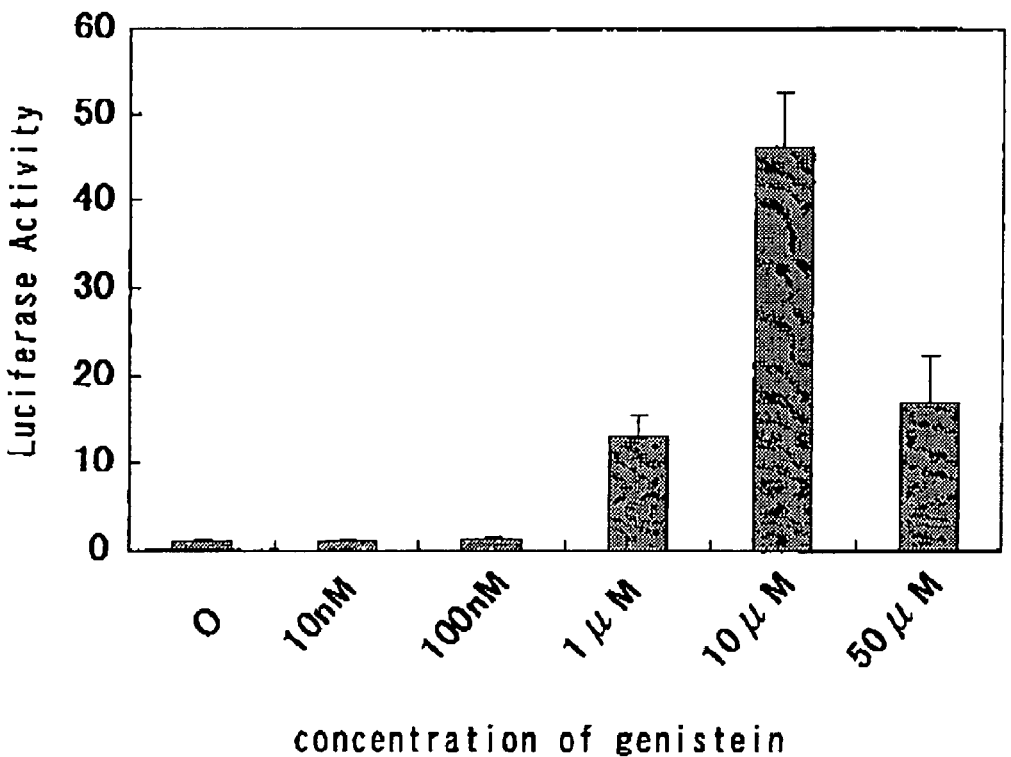
FIG. 4 is a diagram showing a result of measuring the ability of genistein to activate the estrogen receptor activity by the reporter assay using the inventive gene, bger α (N=6). Along the abscissa axis, the concentration of genistein are annotated for each experimental section. The left end column indicated by O corresponds to an experimental section in which DMSO was added at a final concentration of 0.1% in place of the DMSO solution of genistein (genistein-free section). Along the ordinate axis, the luciferase activity-value is shown, where the luciferase activity value of the genistein-free section is normalized as 1.
Figure 5:
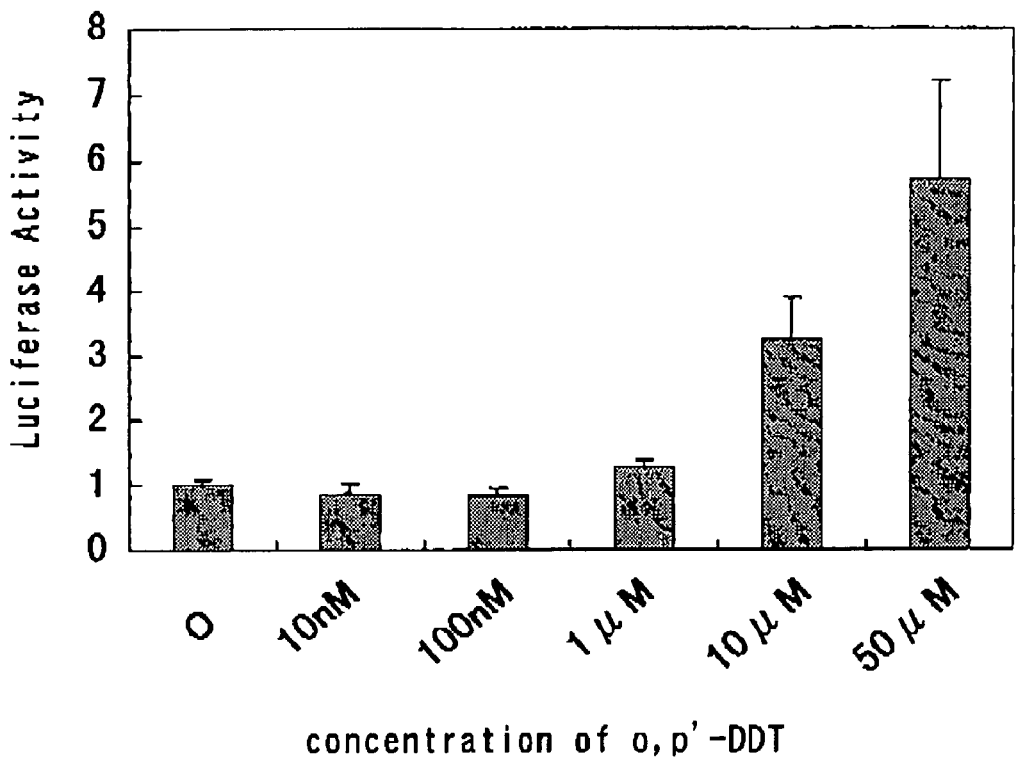
FIG. 5 is a diagram showing a result of measuring the ability of o,p'-DDT to activate the estrogen receptor activity by the reporter assay using the inventive gene, bger α (N=6). Along the abscissa axis, the concentration of o,p'-DDT are annotated for each experimental section. The left end column indicated by O corresponds to an experimental section in which DMSO was added at a final concentration of 0.1% in place of the DMSO solution of o,p'-DDT (o,p'-DDT-free section). Along the ordinate axis, the luciferase activity value is shown, where the luciferase activity value of the o,p'-DDT-free section is normalized as 1.
Figure 6:
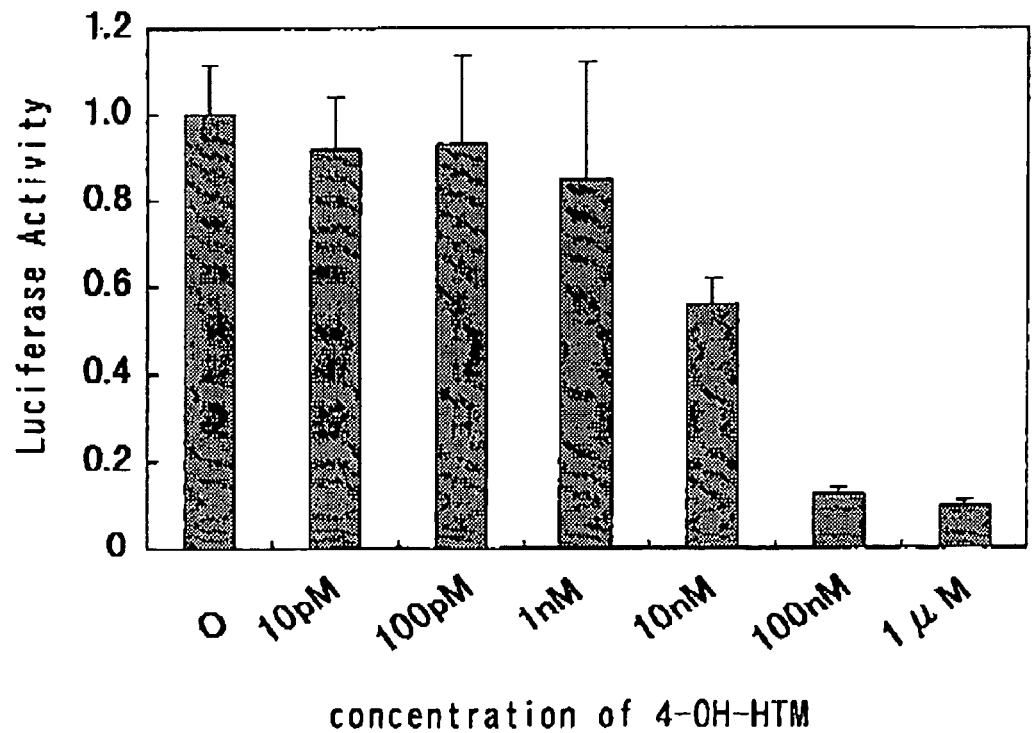
FIG. 6 is a diagram showing a result of measuring the ability of 4-hydroxytamoxifen (4-OH-HTM) to activate the estrogen receptor activity by the reporter assay using the inventive gene, bger α (N=6). Along the abscissa axis, the concentration of 4-OH-HTM allowed to coexist with 10 nM of E2 are annotated for each experimental section. The left end column indicated by O corresponds to an experimental section in which DMSO was added at a final concentration of 0.1% in place of the DMSO solution of 4-OH-HTM (4-OH-HTM-free section). Along the ordinate axis, the luciferase activity value is shown, where the luciferase activity value of the 4-OH-HTM-free section is normalized as 1.
Figure 7:
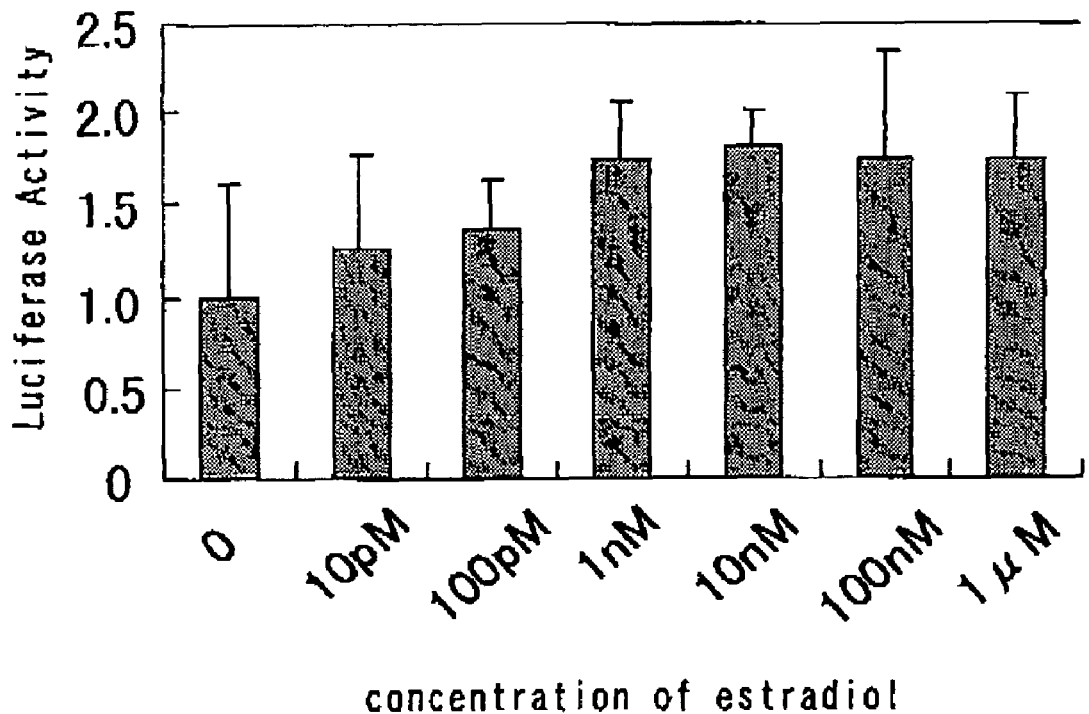
FIG. 7 is a diagram showing a result of measuring the ability of E2 to activate the estrogen receptor activity by the reporter assay using the inventive gene, bger α2 (N=6). Along the abscissa axis, the concentration of E2 are annotated for each experimental section. The left end column indicated by O corresponds to an experimental section in which DMSO was added at a final concentration of 0.1% in place of the DMSO solution of E2 (E2-free section). Along the ordinate axis, the luciferase activity value is shown, where the luciferase activity value of the E2-free section is normalized as 1.
Figure 8:
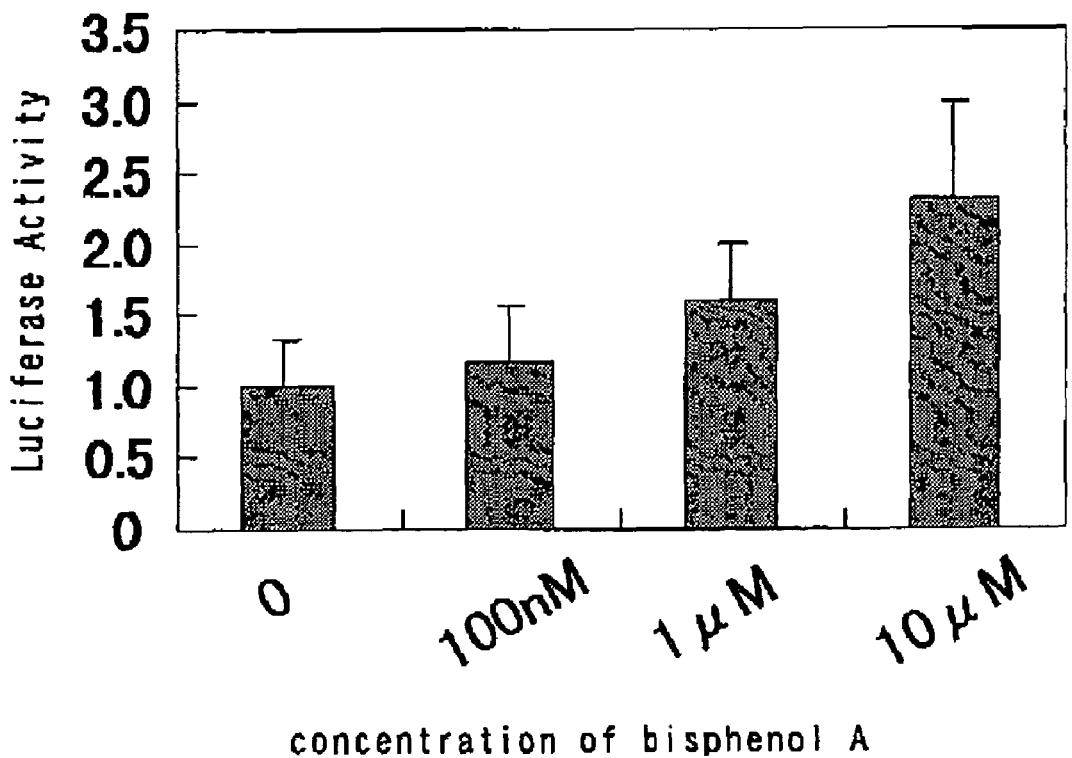
FIG. 8 is a diagram showing a result of measuring the ability of bisphenol A to activate the estrogen receptor activity by the reporter assay using the inventive gene, bger α2 (N=6). Along the abscissa axis, the concentration of bisphenol A are annotated for each experimental section. The left end column indicated by O corresponds to an experimental section in which DMSO was added at a final concentration of 0.1% in place of the DMSO solution of bisphenol A (bisphenol A-free section). Along the ordinate axis, the luciferase activity value is shown, where the luciferase activity value of the bisphenol A-free section is normalized as 1.
Figure 9:
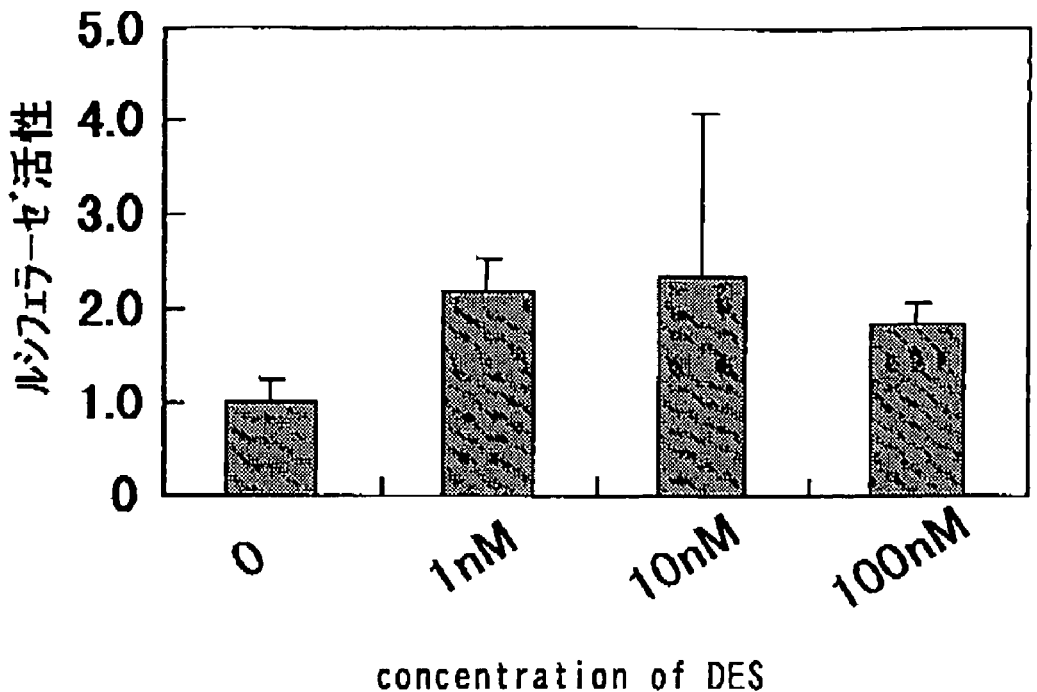
FIG. 9 is a diagram showing a result of measuring the ability of diethylstilbestrol (DES) to activate the estrogen receptor activity by the reporter assay using the inventive gene, bger α2 (N=6). Along the abscissa axis, the concentration of DES are annotated for each experimental section. The left end column indicated by O corresponds to an experimental section in which DMSO was added at a final concentration of 0.1% in place of the DMSO solution of DES (DES-free section). Along the ordinate axis, the luciferase activity value is shown, where the luciferase activity value of the DES-free section is normalized as 1.
Figure 10:
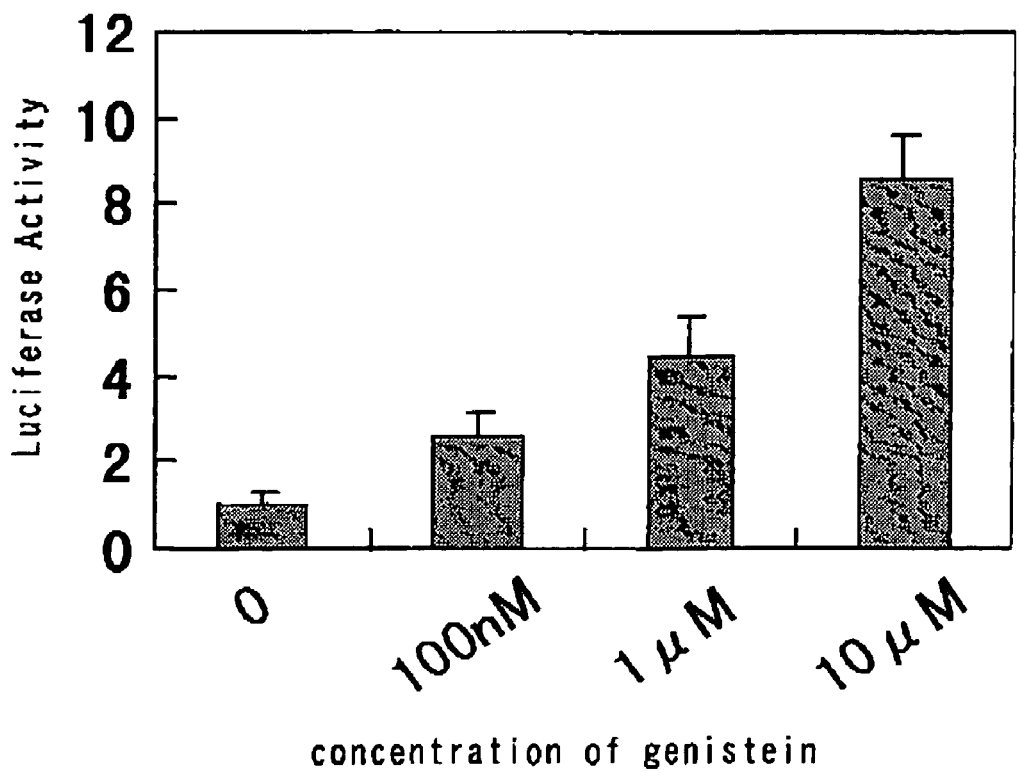
FIG. 10 is a diagram showing a result of measuring the ability of genistein to activate the estrogen receptor activity by the reporter assay using the inventive gene, bger α2 (N=6). Along the abscissa axis, the concentration of genistein are annotated for each experimental section. The left end column indicated by O corresponds to an experimental section in which DMSO was added at a final concentration of 0.1% in place of the DMSO solution of genistein (genistein-free section). Along the ordinate axis, the luciferase activity value is shown, where the luciferase activity value of the genistein-free section is normalized as 1.
Figure 11:
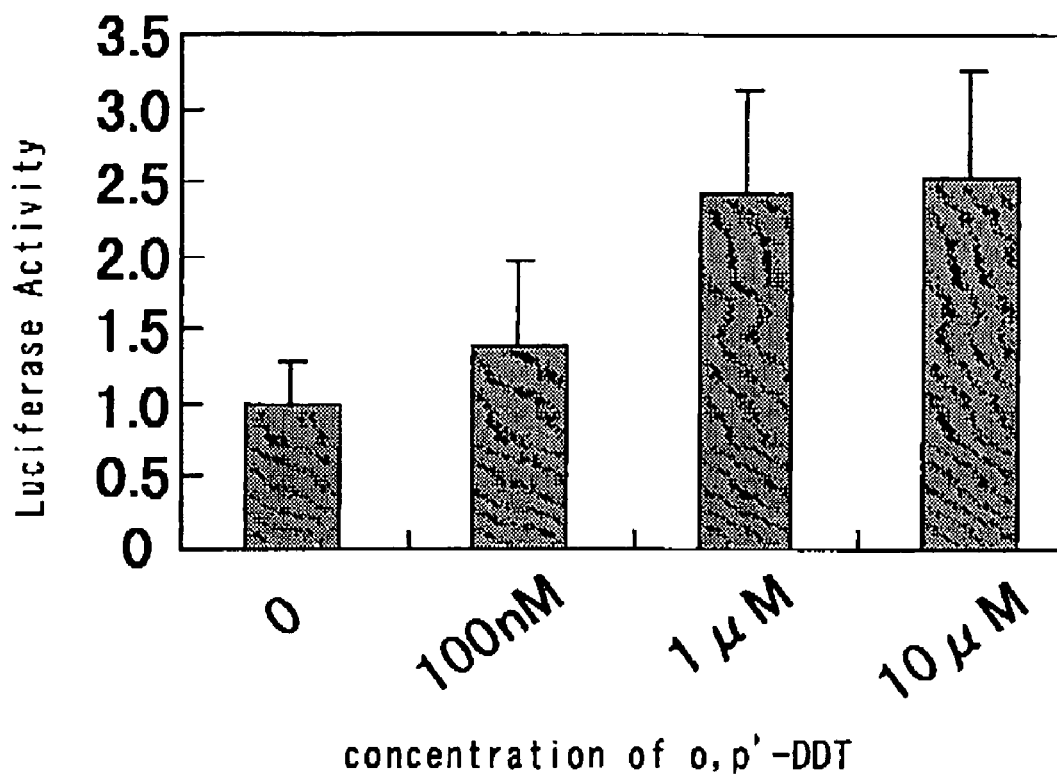
FIG. 11 is a diagram showing a result of measuring the ability of o,p'-DDT to activate the estrogen receptor activity by the reporter assay using the inventive gene, bger α2 (N=6). Along the abscissa axis, the concentration of o,p'-DDT are annotated for each experimental section. The left end column indicated by O corresponds to an experimental section in which DMSO was added at a final concentration of 0.1% in place of the DMSO solution of o,p'-DDT (o,p'-DDT-free section). Along the ordinate axis, the luciferase activity value is shown, where the luciferase activity value of the o,p'-DDT-free section is normalized as 1.

The present invention is described in detail below.

The inventive gene is a gene coding an estrogen receptor. Specifically, examples of the inventive gene include (a) a gene coding an estrogen receptor comprising the amino acid sequence of SEQ ID NO: 1, (b) a gene coding an estrogen receptor comprising the amino acid sequence of SEQ ID NO: 4, (c) a gene coding an estrogen receptor comprising the amino acid sequence of SEQ ID NO: 23, (d) a gene coding an estrogen receptor comprising an amino acid sequence exhibiting 95% or more amino acid identity to the amino acid sequence of SEQ ID NO: 1, (e) a gene coding an estrogen receptor comprising an amino acid sequence exhibiting 95% or more amino acid identity to the amino acid sequence of SEQ ID NO: 4, (f) a gene coding an estrogen receptor comprising an amino acid sequence exhibiting 85% or more amino acid identity to the amino acid sequence of SEQ ID NO: 23, (g) an estrogen receptor gene comprising the nucleotide sequence represented by nucleotide numbers 424 to 1941 of SEQ ID NO: 2, (h) an estrogen receptor gene comprising the nucleotide sequence represented by nucleotide numbers 74 to 1819 of SEQ ID NO: 5, (i) an estrogen receptor gene comprising the nucleotide sequence represented by nucleotide numbers 106 to 1767 of SEQ ID NO: 24, and the like.

With respect to the present invention, "an estrogen receptor comprising an amino acid sequence exhibiting 95% or more amino acid identity to the amino acid sequence of SEQ ID NO: 1" includes, for example, an estrogen receptor comprising an amino acid sequence exhibiting 95% or more amino acid identity to the amino acid sequence of SEQ ID NO: 1 in a region composed of approximate 400 amino acid residues or more and having the receptor function substantially comparable to that of the estrogen receptor comprising the amino acid sequence of SEQ ID NO: 1. In the amino acid sequence of the protein, the differences which may be observed from the amino acid sequences of SEQ ID NO: 1 are such as deletion, substitution, and addition of certain amino acids. Such differences include, for example, a polymorphic variation which occurs naturally resulting from the difference by such as the species, individual, organ, tissue or the like of the animals. The gene coding this type of estrogen receptor may be a natural gene or, for example, a gene produced by introducing mutations into a natural gene using the site-directed mutagenesis or any other mutagenesis. The sequence identity to the amino acid sequence of SEQ ID NO: 1 is, for example, preferably 95% or more.

With respect to the present invention, "an estrogen receptor comprising an amino acid sequence exhibiting 95% or more amino acid identity to the amino acid sequence of SEQ ID NO: 4" includes, for example, an estrogen receptor comprising an amino acid sequence exhibiting 95% or more amino acid identity to the amino acid sequence of SEQ ID NO: 4 in a region composed of approximate 400 amino acid residues or more and having the receptor function substantially comparable to that of the estrogen receptor comprising the amino acid sequence of SEQ ID NO: 4. In the amino acid sequence of the protein, the differences which may be observed from the amino acid sequences of SEQ ID NO: 4 are such as deletion, substitution, and addition of certain amino acids. Such differences include, for example, a polymorphic variation which occurs naturally resulting from the difference by such as the species, individual, organ, tissue or the like of the animals. The gene coding this type of estrogen receptor may be a natural gene or, for example, a gene produced by introducing mutations into a natural gene using the site-directed mutagenesis or any other mutagenesis. The sequence identity to the amino acid sequence of SEQ ID NO: 4 is, for example, preferably 95% or more.

With respect to the present invention, "an estrogen receptor comprising an amino acid sequence exhibiting 95% or more amino acid identity to the amino acid sequence of SEQ ID NO: 23" includes, for example, an estrogen receptor comprising an amino acid sequence exhibiting 95% or more amino acid identity to the amino acid sequence of SEQ ID NO: 23 in a region composed of approximate 400 amino acid residues or more and having the receptor function substantially comparable to that of the estrogen receptor comprising the amino acid sequence of SEQ ID NO: 23. In the amino acid sequence of the protein, the differences which may be observed from the amino acid sequences of SEQ ID NO: 23 are such as deletion, substitution, and addition of certain amino acids. Such differences include, for example, a polymorphic variation which occurs naturally resulting from the difference by such as the species, individual, organ, tissue or the like of the animals. The gene coding this type of estrogen receptor may be a natural gene or, for example, a gene produced by introducing mutations into a natural gene using the site-directed mutagenesis or any other mutagenesis. The sequence identity to the amino acid sequence of SEQ ID NO: 23 is, for example, preferably 95% or more.

In the present invention, "sequence identity" refers to the homology and identity between two amino acid sequences. Such "sequence identity" may be determined by comparing the two sequences, each aligned in an optimal state, over the whole region of the test sequences. As such, additions or deletions (for example, gaps) can be utilized in the optimal alignment of the test nucleic acid sequences or amino acid sequences. Such sequence identity can be calculated through the step of producing the alignment conducted by a homology analysis using a program such as FASTA (Pearson & Lipman, Proc. Natl. Acad. Sci. USA, 4, 2444-2448 (1988)), BLAST (Altschul et al., Journal of Molecular Biology, 215, 403-410 (1990)), CLUSTAL W (Thompson, Higgins & Gibson, Nucleic Acid Research, 22, 4673-4680 (1994a)) and the like. Such programs, for example, can be typically utilized on the webpage (http://www.ddbj.nig.ac.jp) of the DNA Data Bank of Japan (the international databank operated within the Center for Information Biology and DNA Data Bank of Japan). Further, the sequence identity may be determined by utilizing a commercially available sequence analysis software, such as Vector NT1, GENETYX-WIN Ver.5 (Software Development Company, Ltd.) or the like.

The estrogen receptor function can be evaluated using, for example, the reporter assay, two-hybrid system, or the receptor binding assay, all of which are described later. The genes described in the above (a), (b), (d), (e), (g), and (h), in general, code a protein having the estrogen receptor α function. The genes described in the above (c), (f), and (i), in general, code a protein having the estrogen receptor β function.

For example, the inventive gene may be obtained from the tissue of a fin such as a bluegill (scientific name: *Lepomis cantrarahidae*) according to such a genetic engineering process as disclosed in the text (J. Sambrook, E. F. Frisch, and T. Maniatis, Molecular Cloning 2nd edition, Cold Spring Harbor Laboratory, 1989).

For example, first, total RNA is prepared from the tissue of a bluegill. Specifically, the tissue of a bluegill such as a liver tissue is homogenized in a solution containing a protein denaturant such as guanidine hydrochloride and guanidine thiocyanate, and then phenol, chloroform or the like is added to the homogenate to denature the proteins. The denatured proteins are removed by centrifugation or the like as a precipitated fraction, and then the recovered supernatant fraction is extracted using a guanidine hydrochloride/phenol process, a SDS-phenol process, a guanidine thiocyanate/CsCl process, or the like to give total RNA. These processes may be performed using a commercially available kit, for example, including ISOGEN (Nippon Gene) or Trizol reagent (Life Technologies).

The resultant total RNA is used as a template and an oligo dT primer is annealed to a poly A sequence of the RNA, whereby synthesizing a single-stranded cDNA using a reverse transcriptase. Then, the synthesized single-stranded cDNA is used as a template together with a primer which is an RNA obtained by inserting a nick and a gap into the RNA chain using an *E. coli* RnaseH, whereby synthesizing a double-stranded cDNA using an *E. coli* DNA polymerase I. Subsequently, the both ends of the synthesized double-stranded cDNA is made blunt using a T4 DNA polymerase. The resultant double-stranded cDNA is purified and recovered by means of a standard procedure such as a phenol-chloroform extraction and ethanol precipitation. A commercially available kit based on the methods described above may for example be a cDNA synthesis system plus (Amarsham Pharmacia Biotech) or a TimeSaver cDNA synthesis kit (Amarsham Pharmacia Biotech). Then the resulting double-stranded cDNA is ligated to a vector such as a plasmid pUC118 or phage λgt10 using a ligase to prepare a cDNA library. From a cDNA library obtained as described above, the inventive gene can be obtained for example by hybridization methods or PCR methods.

To obtain the genes described in the above (a), (b), (d), (e), (g), and (h) from a cDNA library, hybridization method where a DNA comprising a partial nucleotide sequence of the nucleotide sequence of one of SEQ ID NO: 2 or SEQ ID NO: 5 may be used as a probe, or PCR method where oligonucleotides comprising a partial nucleotide sequence of the nucleotide sequence of one of SEQ ID NO: 2 or SEQ ID NO: 5 may be used as a primer, can be employed.

Probes used for the hybridization method may include, for example, DNA comprising the nucleotide sequence represented by the nucleotides 424 to 483, 871 to 924, or 1863 to 1881 of SEQ ID NO:2, and DNA comprising the nucleotide sequence represented by the nucleotides 182 to 217 of SEQ ID NO:5. The hybridization may be performed under the following conditions: for example, in the presence of 6×SSC (0.9 M NaCl and 0.09 M sodium citrate), 5×Denhardt's solution (0.1% (w/v) Ficoll 400, 0.1% (w/v) polyvinylpyrrolidone, and 0.1% (w/v) BSA), 0.5% (w/v) SDS, and 100 μg/ml of denatured salmon sperm DNA or in a DIG EASY Hyb solution (Boehringer Mannheim) containing 100 μg/ml of denatured salmon sperm DNA, holding at 65° C., then in the presence of 1×SSC (0.15 M NaCl and 0.015 M sodium citrate) and 0.5% (w/v) SDS, holding at room temperature for 15 minutes twice, and in the presence of 0.1×SSC (0.015 M NaCl and 0.0015 M sodium citrate) and 0.5% (w/v) SDS, holding at 68° C. for 30 minutes.

Primers used for the PCR method may be obtained by selecting nucleotide sequences, with a length of about 20 bp to about 40 bp and with G+C content of about 40% to about 60%, from the 5' non-translation region and 3' non-translation of SEQ ID NO:2 or SEQ ID NO:5, followed by synthesizing an oligonucleotide comprising a nucleotide sequence selected from 5' non-translation region and an oligonucleotide comprising the nucleotide sequence complementary to the nucleotide sequence selected from 3' non-translation region. Specifically, examples of combination of primers include an oligonucleotide comprising the nucleotide sequence of SEQ ID NO:6 as a forward primer, and an oligonucleotide comprising the nucleotide sequence of SEQ ID NO:7 as a reverse primer. For example, PCR may be performed under the following conditions: 50 μl of a reaction solution containing 5 μl of 10×LA Taq buffer (Takara), 8 μl of 2.5 mM dNTP mixture (wherein the mixture contains dATP, dGTP, dCTF, and dTTP at each content of 2.5 mM, and each of them is at a final concentration of 0.4 mM), 5 μl of 25 mM MgCl$_2$, 0.5 to 2.5 μl of 10 μM each primer (at each final concentration of 0.1 to 0.5 μM), 0.1 to 1 μg of cDNA template, and 2.5 units of LATaq polymerase (Takara); and 30 cycles of temperature maintenance is performed, each cycle being 94° C. for 1 minute, then 55° C. for 2 minutes, and 72° C. for 2.5 minutes.

To obtain the genes described in the above (c), (f) and (i) from a cDNA library, hybridization method where a DNA comprising a partial nucleotide sequence of the nucleotide sequence of SEQ ID NO: 24 may be used as a probe, or PCR method where oligonucleotides comprising a partial nucleotide sequence of the nucleotide sequence of SEQ ID NO: 24 may be used as a primer, can be employed.

Probes used for the hybridization method may include, for example, DNA comprising the nucleotide sequence represented by the nucleotides 166 to 261, or 1654 to 1800 of SEQ ID NO:24. The hybridization may be performed under the following conditions: for example, in the presence of 6×SSC (0.9 M NaCl and 0.09 M sodium citrate), 5×Denhardt's solution (0.1% (w/v) Ficoll 400, 0.1% (w/v) polyvinylpyrrolidone, and 0.1% (w/v) BSA), 0.5% (w/v) SDS, and 100 μg/ml of denatured salmon sperm DNA or in a DIG EASY Hyb solution (Boehringer Mannheim) containing 100 μg/ml of denatured salmon sperm DNA, holding at 65° C., then in the presence of 1×SSC (0.15 M NaCl and 0.015 M sodium citrate) and 0.5% (w/v) SDS, holding at room temperature for 15 minutes twice, and in the presence of 0.1×SSC (0.015 M NaCl and 0.0015 M sodium citrate) and 0.5% (w/v) SOS, holding at 68° C. for 30 minutes.

Primers, with a length of about 20 bp to about 40 bp, used for the PCR method may be obtained by synthesizing an oligonucleotide comprising a nucleotide sequence selected from 5' non-translation region of the nucleotide sequence of SEQ ID NO:24 and an oligonucleotide comprising the nucleotide sequence complementary to the nucleotide sequence selected from 3' non-translation region of the nucleotide sequence of SEQ ID NO:24. Specifically, examples of the forward primer include an oligonucleotide comprising the nucleotide sequence of SEQ ID NO:26 and examples of the reverse primer include an oligonucleotide comprising the nucleotide sequence of SEQ ID NO:27. Another examples of the forward primer include an oligonucleotide comprising the nucleotide sequence represented by the nucleotides 41 to 68 of SEQ ID NO:24, more specifically an oligonucleotide comprising the nucleotide sequence of SEQ ID NO:30. Another examples of the reverse primer include an oligonucleotide comprising a nucleotide sequence complementary to the nucleotide sequence represented by the nucleotides 1874 to 1900 of SEQ ID NO:24, more specifically an oligonucleotide comprising the nucleotide sequence of SEQ ID NO:31. For example, PCR may be performed under the following conditions: 50 μl of a reaction solution containing 5 μl of 10×EX Taq buffer (Takara), 4 μl of 2.5 mM dNTP mixture (wherein the mixture contains dATP, dGTP, dCTP, and dTTP at each content of 2.5 mM, and each of them is at a final concentration of 0.2 mM), 0.25 to 1.25 μl of 20 μM each primer (at each final concentration of 0.1 to 0.5 μM), 0.1 to 0.5 μg of cDNA template, and 1.25 units of EX Taq polymerase (Takara); and 30 cycles of temperature maintenance is performed, each cycle being 94° C. for 1 minute, then 55° C. for 2 minutes, and 72° C. for 2.5 minutes.

The resulting inventive gene may be cloned into a vector according to such a genetic engineering process as disclosed in the text (J. Sambrook, E. F. Frisch, and T. Maniatis, Molecular Cloning 2nd edition, Cold Spring Harbor Laboratory, 1989). Specifically, for example, the cloning may be performed using a commercially available plasmid vector such as TA cloning kit (Invitrogen) or pBluescriptII (Stratagene).

Alternatively, based on the nucleotide sequence of SEQ ID NO:2, 5 or 24, the inventive gene may be chemically synthesized by a conventional method such as a phosphate triester method (Hunkapiller, M. et al., Nature, 310, 105, 1984).

The nucleotide sequence of the resulting inventive gene may be confirmed by the Maxam-Gilbert method (for example, as disclosed in Maxam, A. M. & W. Gilbert, Proc.

Natl. Acad. Sci. USA, 74, 560, 1977) or the Sanger method (for example, as disclosed in Sanger, F & A. R. Coulson, J. Mol. Biol., 94, 441, 1975 or Sanger, F, & Nicklen and A. R. Coulson., Proc. Natl. Acad. Sci. USA, 74, 5463, 1917).

The inventive gene may be inserted into a vector operable in a host cell to which the gene is incorporated (hereinafter referred to as the basic vector) according to a conventional genetic engineering process to form the inventive vector. For example, the basic vector contains genetic information replicable in the host cell, is autonomously replicable, can be isolated or purified from the host cell, and has a detectable marker.

Examples of the basic vector applicable in constructing the inventive vector include: plasmid pUC119 (Takara) and phagemid pBluescriptII (Stratagene) each for an $E. coli$ (a microorganism) host cell; plasmids pGBT9, pGAD424, and pACT2 (Clontech) each for a budding yeast host cell: a plasmid such as pRC/RSV and pRc/CMV (Invitrogen), a virus-derived autonomous replication origin-containing vector such as bovine papilloma virus plasmid pBPV (Amersham Pharmacia Biotech) and EB virus plasmid pCEP4 (Invitrogen), and a virus such as vaccinia virus each for a mammal host cell; and an insect virus such as baculovirus for an insect host cell. When the autonomous replication origin-containing vector such as the plasmid pACT2 for the yeast, the bovine papilloma virus plasmid pBPV, and the EB virus plasmid pCEP4 is used to construct the inventive vector, the vector introduced into the host cell is held in the form of an episome in the cell.

In order to incorporate the inventive gene into baculovirus or vaccinia virus, a transfer vector may be used, which contains a nucleotide sequence homologous to the virus genome to be used. Examples of such a transfer vector include plasmids such as pVL1392 and pVL1393 (Smith. G. E., Summers M. D. et al., Mol. Cell. Biol., 3, 2156-2165, 1983) commercially available from Pharmingen, and pSFB5 (Funahashi, S. et al., J. Virol., 65, 5584-5588, 1991). When the inventive gene is introduced into the transfer vector and the vector and the virus genome are simultaneously introduced into a host cell, homologous recombination occurs between the vector and the virus genome so as to form a virus having the inventive gene incorporated in the genome. The virus genome may be a baculovirus, adenovirus, or vacciniavirus genome.

More specifically, in the process of incorporating the inventive gene Into baculovirus, first, the inventive gene is inserted into a multicloning site of the transfer vector such as pVL1393 and pVL1392, and then the transfer vector DNA and Baculovirus genome DNA (Baculogold (Pharmingen)) are introduced into an insect cell line Sf21 (available from ATCC) by calcium phosphate method. The resulting cells are cultured, and then the culture is subjected to centrifugation and other processes so that viral particles are recovered, whose genome contains the inventive gene. The recovered viral particles are deproteinized with phenol or the like to give the inventive gene-containing virus genome. The resulting virus genome may be introduced into a host cell having the ability to form viral particles, such as insect cell line Sf21, by calcium phosphate method or the like. The resulting cells may be cultured so that the inventive gene-containing viral particles can be multiplied.

Alternatively, the inventive gene may be directly incorporated into a relatively small genome such as a mouse leukemia virus genome without using the transfer vector. For example, the inventive gene is incorporated into a cloning site of virus vector-DC(X) (Eli Gilboa et al., BioTechniques, 4, 504-512, 1986). The resulting inventive gene-containing virus vector may be introduced into a packaging cell such as Ampli-GPE (J. Virol., 66, 3755, 1992) to form viral particles which bear the inventive gene-containing virus genome.

A promoter operable in the host cell may be operably linked upstream of the inventive gene and incorporated into the basic vector to construct the inventive vector, which is capable of expressing the inventive gene in the host cell. The term "operably linked" means that the promoter is linked to the inventive gene in such a manner that the inventive gene can be expressed under the control of the promoter in the inventive gene-containing host cell. Examples of the promoter operable in the host cell include DNAs that exhibit a promoter activity in the host cell. Such examples include: a lactose operon promoter (lacP), a tryptophan operon promoter (trpP), an arginine operon promoter (argP), a galactose operon promoter (galP), tac promoter, T7 promoter, T3 promoter, and a λ-phage promoter (λ-pL and λ-pR) each for an $E. coli$ host cell; a Rous sarcoma virus (RSV) promoter, a cytomegalovirus (CMV) promoter, a early or late simian virus (SV40) promoter, and a mouse papilloma virus (MMTV) promoter each for an animal or fission yeast host cell; and ADH1 promoter for a budding yeast host cell.

The basic vector may preliminarily contain the promoter operable in the host cell. When such a basic vector is used, the inventive gene may be inserted downstream of the promoter contained in the vector so as to be operably linked to the promoter. For example, the above plasmids pRc/RSV, pRc/CMV and the like have a cloning site downstream from the promoter operable in an animal cell. The inventive gene may be inserted into the cloning site to form a vector, which may be introduced into the animal cell to express the inventive gene. These plasmids preliminarily contain an SV40 autonomous replication origin (ori). Therefore, any of these plasmids may be introduced into a cultured cell transformed with an ori-deleted SV40 genome, such as a COS cell, so that large numbers of the plasmid can be copied in the cell, and thereby, the inventive gene incorporated in the plasmid can be expressed in a large amount. The above plasmid pACT2 for the yeast has the ADH1 promoter. Therefore, the inventive gene may be inserted downstream of the ADH1 promoter in the plasmid or a derivative thereof to form the inventive vector capable of expressing a large amount of the inventive gene in the budding yeast such as CG1945 (Clontech).

The constructed inventive vector may be introduced into the host cell to form the inventive transformant. Any conventional introducing process may be used depending on the host cell. For the introduction into an $E. coli$ (a microorganism) host cell, any conventional method may be used, for example, including calcium chloride method and electroporation method as disclosed in the text (J. Sambrook, E. F. Frisch, and T. Maniatis, Molecular Cloning 2nd edition, Cold Spring Harbor Laboratory Press, 1989). The introduction of the vector into a mammal host cell, a fin host cell or an insect host cell may be performed according to any general gene transfection method such as calcium phosphate method, DEAE dextran method, electroporation method, and lipofection method. For the introduction into an yeast host cell, for example, Yeast transformation kit (Clontech) may be used based on lithium method.

The introduction of the viral genome into the host cell via the viral vector can be made not only by any of the above general gene transfection methods but also by infecting the host cell with viral particles which carry the inventive gene-containing viral genome.

In order to select the inventive transformant, for example, a marker gene may be introduced into the host cell together with the inventive vector, and then the host cell may be cultured by any method depending on the characteristic of the marker gene. For example, the marker gene may be a drug resistance gene against a selection drug that has killing activity on the host cell, and the inventive vector-containing host cell may be cultured in a medium that contains the selection drug. Examples of the combination of the drug resistance gene and the selection drug include the combinations of a neomycin resistance gene and neomycin, a hygromycin resistance gene and hygromycin, and a blasticidin S resistance gene and blasticidin S. Alternatively, the marker gene may complement auxotrophy of the host cell, and the inventive gene-containing cell may be cultured in a minimal medium free of the nutrient concerning the auxotrophy. When the inventive vector capable of expressing the inventive gene is introduced into a host cell, the inventive transformant by be selected by using a detection method based on the estrogen binding activity.

For example, the inventive transformant in which the inventive gene is located in the chromosome of the host cell is obtained as follows. The inventive vector and the marker gene-containing vector are each digested with a restriction enzyme or the like into a linear form and then introduced into the host cell by any method as described above. The cell is cultured generally for several weeks and then selected based on the expression amount of the introduced marker gene to give a desired transformant. For example, the inventive vector which contains the drug resistance gene as the marker gene is introduced into the host cell by any method as described above. The cell is subcultured in a selection drug-containing medium for at least several weeks, and then the drug-resistant clone surviving in the form of a colony is subjected to culture for clone purification, resulting in the inventive transformant in which the inventive gene is incorporated in the chromosome of the host cell. The transformant can be stored in a frozen state and then allowed to activate as needed. Therefore, not every experiment needs the transformant preparation, and tests can be performed using the transformant with the characteristics and the handling conditions checked in advance.

The resulting inventive transformant may be cultured to produce the estrogen receptor.

For example, the inventive transformant is a microorganism, and in such a case, the transformant may be cultured using any medium that appropriately contains any carbon source, any nitrogen source, any organic or inorganic salt, and the like each for general microorganism culture. The cultivation may be carried out according to any conventional method for general microorganisms, such as solid culture method and liquid culture method (such as rotary shaking culture, reciprocal shaking culture, jar fermenter culture, and tank culture). The culture temperature and the pH of the medium can be each selected from a certain range in which the microorganism can grow. For example, the culture is generally performed at a temperature of about 15° C. to about 40° C. at a pH of about 6.0 to about 8.0. The culture time period depends on various culture conditions but is generally from about one day to about five days. When the expression vector contains an inducible promoter such as a temperature-inducible promoter and an IPTG-inducible promoter, the induction time is preferably within one day and generally several hours.

On the other hand, the transformant may be an animal cell such as a mammal cell, a fin cell and an insect cell, and the transformant may be cultured using any medium for general cell culture. If the transformant is prepared using the selection drug, the culture is preferably performed in the presence of the selection drug. For example, the mammal cell may be cultured using a DMEM medium (Nissui) containing FBS at a final content of 10% at 37° C. under 5% $CO_2$ while the medium may be replaced with fresh one every several days. After the cells are grown in a confluent state, for example, an about 0.25% (w/v) trypsin-containing PBS solution is added so that the cells are separated and dispersed. The cells are then diluted several times and inoculated into a new plate and further cultured. Similarly, the insect cell may be cultured using any insect cell culture medium such as a 10% (v/v) FBS and 2 (w/v) Yeastlate-containig Grace's medium at a culture temperature of 25° C. to 35° C. If the cell tends to peel off the plate as in the case of Sf21 cell, the cells may be dispersed by pipetting and subcultured without using the trypsin solution. When the transformant contains the virus vector such as baculovirus, the culture is preferably terminated before the cell is killed and the cytoplasmic effect is observed, for example, up to 72 hours after the viral infection.

The inventive estrogen receptor produced by the inventive transformant may be recovered from the culture by any appropriate combination of conventional isolation or purification processes. For example, after the culture is completed, the transformant cells are collected by centrifugation or the like, and the collected cells are suspended in a general buffer such as a buffer comprising 20 mM HEPES pH7, 1 mM EDTA, 1 mM DTT, and 0.5 mM PMSF and then homogenized in a Polytron, an ultrasonic apparatus, a Dounce homogenizer, or the like. The resulting homogenate may be ultracentrifuged at several tens thousand×g for several tens minutes to about one hour, and then the supernatant fraction may be taken to give an estrogen receptor-containing fraction. In addition, the supernatant fraction may be subjected to any type of chromatography such as ion exchange, hydrophobic, gel filtration, or affinity chromatography to give the estrogen receptor in a further purified state. In this process, the inventive estrogen receptor-containing fraction may be identified by a DNA binding assay or the like using a probe of an oligonucleotide with a length of about 15 bp to about 200 bp including an estrogen response element sequence, a nucleotide sequence to which the estrogen receptor is capable of binding.

The resulting inventive estrogen receptor may be used in a receptor binding assay or the like for evaluating the ability or the amount of any test substance to bind to or bound to the estrogen receptor.

The inventive gene may be used in a reporter assay for evaluating the ability of any test substance to regulate the estrogen receptor activity. The ability to regulate the estrogen receptor activity may include an agonistic activity and an antagonistic activity on the estrogen receptor.

In the evaluating method using the inventive gene, the "reporter gene linked downstream of a transcriptional control region including an estrogen response element sequence" may be specifically a chimera gene comprising a reporter gene linked downstream of a transcriptional control region or the like of the *Xenopus Vitellogenin* gene including the estrogen response element sequence or a chimera gene comprising a reporter gene linked downstream of the estrogen response element sequence and a nucleotide sequence necessary for transcription initiation. Such a chimera gene may be used for monitoring the ability of the estrogen receptor to control transcription in the host cell. The reporter gene used to prepare such a chimera gene may be a luciferase gene, a secretory alkaline phosphatase gene, a β-galactosidase gene, a chloramphenicol acetyltransferase gene, a growth hormone gene, or the like. A preferred reporter gene is a gene coding for a reporter protein with relatively higher stability in the host cell.

The inventive gene and the reporter gene linked downstream of the transcriptional control region including the estrogen response element sequence are introduced into, for example, an estrogen receptor-absent host cell, such as HeLa, CV-1, Hepa1, NIH3T3, HepG2, COS1, BF-2, and CHH-1 cells, to form a transformant. As described above, the inventive gene may be operably linked to the promoter operable in the host cell and incorporated in the basic vector before introduced into the host cell. The reporter gene linked downstream of the transcriptional control region including the estrogen response element sequence may also incorporated in the basic vector before use. For example, both of the reporter gene-containing vector in which the reporter gene is linked downstream of the transcriptional control region including the estrogen response element sequence and the inventive gene-containing vector in which the inventive gene is operably linked to the promoter operable in the host cell are introduced into the host cell together with the marker gene-containing vector. After the cell is cultured generally for several weeks, the desired transformant is selected based on the expression amount of the introduced marker gene. In the resulting transformant, the reporter gene linked downstream of the transcriptional control region including the estrogen response element sequence and the inventive gene operably linked to the operable promoter are incorporated in the host cell chromosome. The transformant can be stored in a frozen state and then allowed to activate as needed. Therefore, once the transformant is obtained, transformant preparation containing a step of introducing those genes into a host cell does not have to be made at every experiment, and the characteristics of the transformant can be maintained constant. The transformant will therefore be useful in a large scale screening with an automatic robot.

The resulting transformant is cultured in a test substance-containing medium for one day to several days to bring into contact with the test substance. A measurement is then made on the expression amount of the reporter gene of the transformant. If a substance with an estrogen-like activity in the test substance binds to the estrogen receptor produced by the transformant and activates it, the transcription of the reporter gene will be promoted so that the reporter protein encoded by the reporter gene can be stored in the transformant cell or secreted into the medium. The amount of the reporter protein is determined so that the expression amount of the reporter gene can be determined per transformant cell. For example, a luciferase reporter gene is used, and luciferin, the substrate of the luciferase, is added to a crude cell extract prepared from the transformant that has been in contact with the test substance, so that luminescence can be observed in an intensity proportional to the amount of the luciferase in the crude cell extract. Therefore, the intensity of the luminescence may be measured using a measuring apparatus such as a luminometer so that the amount of the luciferase and therefore the expression amount of the luciferase gene can be determined. In a similar manner, under the condition that the transformant is not in contact with the test substance, a measurement is made on the expression amount of the reporter gene The measured expression amount is compared with the amount measured under the test substance contact condition, so that the agonistic activity on the estrogen receptor, i.e., the ability to activate the estrogen receptor of a subsntance with an estrogen-like activity in the test substance can be evaluated. On the other hand, for example, under each of the condition that the transformant is in contact with the estrogen such as 17β-estradiol (hereinafter referred to as E2) and the condition that the transformant is in contact with the estrogen and the test substance at the same time, a measurement is made on the expression amount of the reporter gene in a similar manner to the above. The measurements under both conditions are compared with each other. If the expression amount under the latter condition is lower than that under the former condition, the test material can be evaluated as having the antagonistic activity on the estrogen receptor, i.e., the anti-activation ability on the estrogen receptor.

Based on the expression amount of the intracellular reporter gene, the inventive gene or a DNA including a partial nucleotide sequence of the inventive gene may be applied to an assay system for detecting the ability to form a complex of two types of fusion proteins (two-hybrid) and the ability of the complex to regulate the transcription (two hybrid system, Nishikawa et al., Toxicol. Appl. Pharmacol., 154, 76-83, 1999). Specifically, for example, in the two-hybrid system, where ligand-dependent formation of a complex comprising:

an estrogen receptor encoded by the inventive gene or the ligand binding domain of said estrogen receptor, and a transcription coupling factor capable of ligand-dependently binding to the estrogen receptor;

results in activation of transcription of a reporter gene, the ability of a test substance to regulate estrogen receptor activity can be evaluated by measuring any variation (increase and decrease) in the expression amount of reporter gene when the test substance is added. The ability to regulate estrogen receptor activity may include an agonist activity and an antagonist activity on the estrogen receptor.

The two-hybrid system includes, for example, the transformant, in which the genes described in (A) to (C) listed below is incorporated together into the same host cell.

(A) A chimera gene linked downstream of a promoter operable in the host cell, comprising a nucleotide sequence encoding a fusion protein of the DNA binding domain of the transcription control factor operable in the host cell and the estrogen receptor of the present invention or the ligand binding domain of said estrogen receptor (B) A chimera gene linked downstream of a promoter operable in the host cell, comprising a nucleotide sequence encoding a fusion protein of the transcription activating domain of the transcription control factor operable in the host cell and the transcription coupling factor capable of ligand-dependently binding to the estrogen receptor in the present invention or the receptor binding domain of said transcription coupling factor.

(C) The reporter gene linked downstream of:

a nucleotide sequence, to which the DNA binding domain described in (A) is capable of binding, and a promoter capable of being activated by the transcription activating domain described in (B).

Examples of the host cell include mammal cells, such as budding yeast cells and HeLa cells. To measure the ability of a test substance to regulate the activity of the estrogen receptor in the present invention at a higher accuracy, it is preferable to use the cells containing no intrinsic estrogen receptor.

The "DNA binding domain of the transcription control factor operable in the host cell" described in the above (A) includes, for example, the DNA binding domain of a yeast-derived transcription control factor GAL4 and bacterium-derived repressor LexA if the budding yeast cell is used as the host cell. By linking in frame the DNA encoding each of them, and the DNA of the inventive gene or the DNA comprising the partial nucleotide sequence of the inventive gene encoding the ligand binding domain of the estrogen receptor, the "chimera gene comprising a nucleotide sequence encoding a fusion protein of the DNA binding domain of the transcription control factor operable in the host cell and the estrogen receptor of the present invention or the ligand binding domain of said estrogen receptor" described in (A) can be obtained. The above-mentioned "DNA comprising the partial nucleotide sequence of the inventive gene encoding the ligand binding domain of the estrogen receptor" includes, for example, the DNAs comprising the inventive gene-derived nucleotide sequences, containing the nucleotide sequence encoding the ligand binding domain of the estrogen receptor and not containing the nucleotide sequence encoding the DNA binding domain. Specifically, it includes, for example, the nucleotide sequences containing at least the nucleotide sequence represented by nucleotide numbers 873 to 1689 and not containing nucleotide sequence represented by nucleotide numbers 1 to 762 of SEQ ID NO: 24, and more specifically, includes the DNAs comprising the nucleotide sequence represented by nucleotide numbers 763 to 1767 of SEQ ID NO: 24.

The "transcription activating domain of the transcription control factor operable in the host cell" described in (B) includes for example, transcription activating domain of GAL4 and $E\ coli$-derived B42 acidic transcription activating domain. The "transcription coupling factor capable of ligand-dependently binding to the estrogen receptor in the present invention" is the transcription coupling factor capable of recognizing the complex of the estrogen receptor of the present invention and the ligand and binding to it and specifically, includes, for example, SRC1/NCoA1 (Onate, S. A. et al., Science, 1995, 270. 1354) and TIF2/GRIP1 (Voegel, J. J. et al., EMBO, J., 1996, 15, 3667). By linking in frame the DNA encoding the above-mentioned transcription activating domain and the DNA encoding the above-mentioned transcription coupling factor or the receptor binding domain of said transcription coupling factor, the "chimera gene comprising a nucleotide sequence encoding a fusion protein of the transcription activating domain of the transcription control factor operable in the host cell and the transcription coupling factor capable of ligand-dependently binding to the estrogen receptor in the present invention or the receptor binding domain of said transcription coupling factor" described in the above (B) can be obtained. Note that, by replacing the components of the chimera gene described in (A) with that in (B), the "chimera gene comprising a nucleotide sequence encoding a fusion protein of the DNA binding domain of the transcription control factor operable in the host cell and the transcription coupling factor capable of ligand-dependently binding to the estrogen receptor in the present invention and the receptor binding domain of said transcription coupling factor" and the "chimera gene comprising a nucleotide sequence encoding a fusion protein of the transcription activating domain of the transcription control factor operable in the host cell and the estrogen receptor of the present invention or the ligand binding domain of said estrogen receptor" may be used. Each of these chimera genes are linked downstream the "promoter operable in the host cell", for which, for example, inducible promoters such as GAL1 promoter and constitutive expression promoters such as an ADH promoter may be used if the host cell is a budding yeast cell.

For the reporter gene described in (C), any of luciferase, secretory alkaline phosphatase. β-galactositase, chloramphenicol acetyltransferase, and growth hormone genes reporter protein with relatively higher stability in the host cell is used. Said reporter gene is linked downstream of a nucleotide sequence, to which the bove-mentioned DNA binding domain is capable of binding; and a promoter capable of being activated by the bove-mentioned transcription activating domain. For example, the nucleotide sequence to which the GAL4 DNA binding domain can bind includes the GAL4 binding domain of the GAL1 promoter and the nucleotide sequence to which LexA can bind includes the LexA binding domain. The promoter activated by the GAL4 transcription activating domain includes, for example, an yeast-derived minimal TATA box sequence.

The above-mentioned chimera genes and a reporter gene are, for example, inserted into the vectors and introduced into the same host cell to obtain the transformant. Note that the host cell, if having an intrinsic reporter gene which is available, may be used and in such a case, the step for introducing the reporter gene may be omitted. Alternatively, the transformant can be prepared using any of commercially available kits for preparing the two-hybrid system such as Matchmaker Two-hybrid System (Manufactured by Clontech Corp.) and CheckMate Mammalian Two-hybrid System (Promega Corp.). As an example of the structure of the two-hybrid system where ligand-dependent formation of a complex comprising:

an estrogen receptor encoded by the inventive gene or the ligand binding domain of said estrogen receptor, and a transcription coupling factor capable of ligand-dependently binding to the estrogen receptor;

results in activation of transcription of a reporter gene, for example, the tansformant may be given, in said transformant the genes described in the following (D) and (E) are introduced into the budding yeast Y190 strain (Manufactured by Clontech Corp.) containing a LacZ gene (reporter gene), said LacZ gene being linked downstream of the intrinsic GAL1 UAS(upstream activating sequence) and the yeast-derived minimal TATA box sequence.

(D) A chimera gene linked downstream of the ADH1 promoter, comprising a nucleotide sequence encoding a fusion protein of the DNA binding domain of GAL4 and the estrogen receptor of the present invention or the ligand binding domain of said estrogen receptor, (E) A chimera gene linked downstream of the ADH1 promoter, comprising a nucleotide sequence encoding a fusion protein of the transcription activating domain of GAL4 and the transcription coupling factor TIF1 capable of ligand-dependently binding to the estrogen receptor in the present invention or the receptor binding domain of the TIF1.

As mentioned above, while the prepared transformant being cultivated for, for example, several hours to several days, the test substance is added into the medium culture for making contact with the transformant to induce the formation of the complex of the estrogen receptor or the ligand binding domain of the estrogen receptor and the transcription coupling factor or the receptor binding domain of the transcription coupling factor, and the ability of transcription regulation of the complex is measured using the expression amount of the reporter gene as an indicator. For example, a luciferase reporter gene is used, and luciferin, the substrate of the luciferase, is added to a crude cell extract prepared from the transformant that has been in contact with the test substance, so that luminescence can be observed in an intensity proportional to the amount of the luciferase In the crude cell extract. Therefore, the intensity of the luminescence may be measured using a measuring apparatus such as a luminometer so that the amount of the luciferase and therefore the expression amount of the luciferase gene can be determined. In a similar manner, under the condition that the transformant is not in contact with the test substance, a measurement is made on the expression amount of the reporter gene The measured expression amount is compared with the amount measured under the test substance contact condition, so that the agonistic activity on the estrogen receptor, i.e., the ability to activate the estrogen receptor of a subsntance with an estrogen-like activity in the test substance can be evaluated. On the other hand, for example, under each of the condition that the transformant is in contact with the estrogen such as E2 and the condition that the transformant is in contact with the estrogen and the test substance at the same time, a measurement is made on the expression amount of the reporter gene in a similar manner to the above. The measurements under both conditions are compared with each other. If the expression amount under the latter condition is lower than that under the former condition, the test material can be evaluated as having the antagonistic activity on the estrogen receptor, i.e., the anti-activation ability on the estrogen receptor.

The receptor binding assay using the inventive gene enables the measurement of the ability of any chemical substance to bind to the inventive estrogen receptor, the quantification of the binding amount, and, the analysis of the binding specificity or the binding strength. For example, a labeled ligand is preliminarily allowed to bind to the inventive estrogen receptor, which is recovered from the inventive transformant as described above. The test substance is then allowed to coexist with the labeled ligand so that the test substance competes with the labeled ligand. Depending on the affinity of each for the inventive estrogen receptor, the labeled ligand is released from the receptor. The amount of the labeled ligand bound to the receptor decreases, and therefore, the amount of the label bound to the receptor decreases. Thus, the label amount of the free form or the bound form of the labeled ligand may be monitored to indirectly determine the ability of the test substance to bind to the inventive estrogen receptor.

For example, the labeled ligand may be tritium-labeled E2 or the like. The bound and free forms of the labeled ligand may be separated by hydroxyapatite method, glycerol density gradient ultracentrifugation or the like. The reaction system may broadly be classified into three groups. The first group includes a system in which only a solvent is added to the labeled ligand-bound inventive estrogen receptor and corresponds to the system in which the addition amount of the test substance is zero. In this system, the label amount of the bound form of the labeled ligand represents the total amount of the labeled ligand bound to the inventive estrogen receptor (the total binding amount). The second group includes a system in which for example, an unlabeled ligand is added to the labeled ligand-bound inventive estrogen receptor in such a concentration that the inventive estrogen receptor is saturated with the unlabeled ligand so as to have no capacity for binding to the labeled ligand (for example, 10 μM). In this system, the label amount of the bound form of the labeled ligand is determined as the amount of the labeled ligand nonspecifically bound to the inventive estrogen receptor (the nonspecific binding amount). Therefore, the amount of the labeled ligand specifically bound to the inventive estrogen receptor (the specific binding amount) is calculated by subtracting the nonspecific binding amount from the total binding amount. The third group includes a system in which the test substance is added to the labeled ligand-bound inventive estrogen receptor at a final concentration of 10 μM, for example (such a concentration may arbitrarily be altered depending on the purpose). If the test substance has the ability to bind to the estrogen receptor, the label amount of the bound form of the labeled ligand obtained in this system will be smaller than the specific binding amount obtained as described above under the condition that the addition amount of the test material is zero. Thus, such a receptor binding assay may be performed to determine the ability of the test substance to bind to the inventive estrogen receptor. If the test substance include different substances, the assay can also determine whether the test substance includes any substance that has an affinity for the inventive estrogen receptor. If the ability of the test substance to bind to the inventive estrogen receptor should be evaluated in a more detailed manner, for example, the test substance may be added at different concentrations in the third group in the process of the inventive receptor binding assay. For example, the label amount of the bound form of the labeled ligand may be determined to produce the amounts of the bound and free forms of the ligand, respectively, and then the results may be subjected to the Scatchard analysis so that the binding affinity, the binding specificity, the binding capacity, or the like can be evaluated between the test substance and the inventive estrogen receptor.

The reporter assay, the two-hybrid system, and the receptor binding assay of the present invention can be applied to safety evaluation of chemical substances, detection of environmental estrogen-like substances, and the like.

EXAMPLES

The present invention is more specifically described with reference to the examples below, but such examples are not intended to limit the scope of the present invention.

Note that a protein having the estrogen receptor a function and a gene coding the protein having the estrogen receptor α function are described with reference to the examples 1 to 8. A protein having the estrogen receptor β function and a gene coding the protein having the estrogen receptor β function is also described with reference to the examples 9 to 22.

Example 1

Obtaining the Inventive Gene (1) Preparation of a Probe for Obtaining the Inventive Gene From 100 mg of liver of bluegill, total RNA was extracted using Trizol reagent (manufactured by Life Technologies Co., Ltd.) in accordance with the supplied manual. Using approximately 1 μg of the total RNA and the ThermoScript RT-PCR system (manufactured by Life Technologies Co., Ltd.) a cDNA library was prepared.

An oligonucleotide comprising the nucleotide sequence of SEQ ID NO: 8 and an oligonucleotide comprising the nucleotide sequence of SEQ ID NO: 9 were synthesized. PCR (30 cycles conducted wherein one cycle involves incubation at 94° C. for one minute, 55° C. for one more minute, and then at 74° C. for 2.5 minutes) was performed using said oligonucleotides as primers and the cDNA prepared as described above as a template. Approximately 1 kbp of amplified DNA was subcloned into a TA cloning vector prepared using a EcoRV site of pBluescriptIISK(+) vector (manufactured by Stratagene Inc.) and the nucleotide sequence of the DNA inserted into the vector was analyzed. Based on the result of the analysis, the DNA comprising the nucleotide sequence of SEQ ID NO: 3 was obtained. Approximately 2 μg of the DNA of the vector having said DNA inserted was digested with restriction enzymes EcoRI and SalI, underwent 1% of agarose gel electrophoresis for separation, and approximately 1 kb of DNA was collected from the gel. By directly labeling the resultant DNA with a thermostable alkaline phosphatase using the AlkPhos Direct system (manufactured by Amersham Pharmacia Biotech Inc. Inc.), the probe was prepared.

(2) Preparation of cDNA Library

From liver tissue of bluegill, total RNA was prepared in accordance with the phenol-chloroform-isoamyl alcohol technique (Plant Cell Physiol. 36(1): pp85-93(1995)). The yield of the total RNA was approximately 2.8 mg. From approximately 500 μg of the total RNA, poly(A)$^+$RNA was prepared using Oligotex(dT)$_{30}$-Super(manufactured by Takara Shuzo Co., Ltd.). The yield of poly(A)$^+$RNA was approximately 10 μg. Then, a cDNA library was prepared in accordance with the Gubler and Hoffman method. In this step, first, single-stranded cDNAs were synthesized using 2.4 μg of poly(A)$^+$RNA, Oligo(dT)$_{18}$-linker primer ((GA)$_{10}$ ACGCGTCGACTCGAGCGGCCGCGGACCG(T)$_{18}$, contaning an XhoI recognition sequence), RAV-2 RTase (manufactured by Takara Shuzo Co., Ltd.) and SuperScriptII RTase (manufactured by Gibco-BRL) and by adding 5-methyl dCTP. Double-strand cDNA was synthesized from the resultant single-stranded cDNA and the both ends of the synthesized double-stranded cDNA were made blunt, at which an EcoRI-NotI-BamHI adaptor (code 4510 manufactured by Takara Shuzo Co., Ltd.) was ligated. Said DNA was digested with a restriction enzyme XhoI and dispensed in a spin column to separate low molecular weight DNA components, and ligated with λZAPII digested with EcoRI and XhoI. Using the resultant DNA and the in vitro packaging kit (manufactured by Stratagene Inc.), in vitro packaging was performed to obtain a cDNA library. Using *E. coli* XL1 Blue MRF' strain (manufactured by Stratagene Inc.) as a host cell, said cDNA library was titrated, estimating that the content of the insert was approximately 95% based on the appearnce rates of blue and white colonies, respectively.

(3) Obtaining the Inventive Gene bgerα

The cDNA library prepared in Example 1 (2) was introduced into *E. coli* XL1 Blue MRF' strain and an aliquot of approximately 50,000 clones was plated on each of LB plates (1% Bacto-Triptone, 0.5% Yeast extract, 0.5% NaCl, 1.5% agar) with 150 mm in diameter to form plaques. A total of six these plates were prepared for making screening on 300,000 clones as described below. From the individual plates, phage DNA was moved onto the Hybond N+ membranes (manufactured by Amasham Pharmacia Biotech), and said membranes were immersed in a denaturing solution (1.5 M NaCl, 0.5 N NaOH) for five minutes and then in a neutralizing solution (1.5 M NaCl, 0.5 M Tris-HCl(pH 7.2), 1 mM EDTA) for ten minutes, and dried. These membranes were incubated at 80° C. for two hours and then using the above-mentioned probe, screening was made by hybridization in accordance with the AlkPhos Direct system protocol. Namely, the above-mentioned membranes were immersed in the hybridization solution containing 0.5 M NaCl (manufactured by Amasham Pharmacia Biotech, 5 ng probe/ml) and incubated at 55° C. for 16 hours. Then, the membranes were incubated in a primary washing buffer (50 mM sodium phosphate buffer (pH 7.0) containing 2 M urea, 0.1% SDS, 150 mM NaCl, 1 mM MgCl$_2$, and 0.2% blocking reagent) at 60° C. for ten minutes and then incubated in the primary washing buffer at 65° C. for ten minutes again. Moreover, they were washed in a secondary washing buffer (50 mM sodium phosphate buffer containing 100 mM NaCl and 2 mM MgCl$_2$) at room temperature for five minutes twice. On the washed membranes, an attempt of detecting any signals was made using CDP-Star contained in the AlkPhos Direct system as a substrate and a chemiluminescent analyzer with an alkaline phosphatase enzyme. For films, Hyperfilm ECL (manufactured by Amarsham Pharmacia Biotech) was used. Ten positive clones were individually selected starting from one with the strongest signal, collected using sterilized chips, suspended in a SM buffer (50 mM Tris-HCl (pH 7.5), 100 mM NaCl, MgSO$_4$.H$_2$O, 0.01% gelatine), and kept at 4° C. Said positive clones were cultivated, and an aliquot of approximate 1,000 to 1,500 clones was plated on each of LB plates with approximate 90 mm in diameter (a total of ten plates) for forming plaques, and in the same manner as that mentioned above, screening was made by hybridization. As a result, among the above-mentioned ten positive clones, a positive signal was detected on three clones, which were collected as positive clones. Then, these three positive clones were cultivated, an aliquot of approximate 200 clones was plated on each of LB plate with approximate 90 mm in diameter for forming plaques, and in the same manner as that mentioned above, screening was made by hybridization. In this screening process, the clones with the positive signal detected were isolated as purified clones. From the vector contained in said positive clone, plasmid where the DNA inserted into said vector was cloned between the EcoRI and XhoI sites of pBluescript SK(–) was obtained using the in vivo excision system in accordance with the protocol supplied with the λZAPII vector kit (manufactured by Stratagene Inc.). On the DNA cloned into said plasmid, nucleotide sequence analysis was made using the Primer Walking technique. The result of the analysis showed that said DNA contained the nucleotide sequence of SEQ ID NO: 2 and thereby coded the amino acid sequence of SEQ ID NO: 1 (hereafter, the estrogen receptor comprising said amino acid sequence is referred to as BGERα and the gene coding said estrogen receptor as the inventive gene, bgerα, and said plasmid was termed pBSBGERα). *E. coli* DH5α strain containing the plasmid pBSBGERα (*Escherichia coli* DH5α/pBSB-GERα) was deposited under its deposit number FERM BP-6876 in International Patent Organism Depositary (IPOD), National Institute of Advanced Industrial Science and Technology, Chuo 6$^{th}$, Higashi 1-1, Tsukuba, Ibaraki (Japan), postal code 305-8566) in 20 Sep. 1999.

(4) Obtaining the Inventive Gene bgerα2

From approximately 100 mg of liver of bluegill, total RNA was extracted using Trizol reagent (manufactured by Life Technologies Co., Ltd.) in accordance with the supplied manual. Using approximately 1 μg of resultant total RNA and the ThermoScript RT-PCR system (manufactured by Life Technologies Co., Ltd.), a cDNA library was prepared. Moreover, the oligonucleotide comprising the nucleotide sequence of SEQ ID NO: 10 and the oligonucleotide comprising the nucleotide sequence of SEQ ID NO: 11 were synthesized. PCR (30 cycles conducted wherein one cycle involves incubation at 94° C. for one minute, 60° C. for one more minute, and then at 74° C. for 0.5 minute) was performed using LA-Taq (manufactured by Takara Shuzo Co., Ltd) and said oligonucleotides as primers for amplifying the DNA Electrophoresis was performed on the amplified DNA using 3% NuSieve3: 1 agarose gel (manufactured by FMC Bioproducts Corp.). As a result, two kinds of DNAs with different lengths were detected. These DNA were collected from the gel and on the DNAS, direct sequencing was performed. The longer DNA contained the partial nucleotide sequence of the nucleotide sequences of SEQ ID NO: 2 and the shorter DNA contained the nucleotide sequence with said partial nucleotide sequence where the nucleotide sequences of SEQ ID NO: 12 were lost. Then, PCR (30 cycles conducted wherein one cycle involves incubation at 94° C. for one min., 55° C. for one more min., and then at 74° C. for 2.5 min.) was performed with LA-Taq (manufactured by Takara Shuzo Co., Ltd.) using said bluegill liver-derived cDNA prepared as described above as a template and an oligonucleotide comprising the nucleotide sequence of SEQ ID NO: 13 and an oligonucleotide comprising of the nucleotide sequence of SEQ ID NO: 7 as primers. The approximately 2.0 kbp of amplified DNA was cloned using the TA cloning vector (pGEM-T manufactured by Promega Corp.) in accordance with the manual supplied with that product and nucleotide sequences of the vector DNAs contained in resultant several clones were analyzed. As a result, the DNA comprising the nucleotide sequence represented by nucleotide numbers 424 to 1941 of SEQ ID NO: 2 and the DNA comprising the nucleotide sequence represented by nucleotide numbers 74 to 1819 of SEQ ID NO: 5 were obtained. It was revealed that the nucleotide sequence represented by nucleotide numbers 74 to 1819 of SEQ ID NO: 5 coded for the amino acid sequence of SEQ ID NO: 4 (hereafter, the estrogen receptor comprising said amino acid sequence is referred to as BGERα2 and the gene coding said estrogen receptor as the inventive gene bgerα2).

Example 2

Construction of the Inventive Vector for Animal Cell Expression Containing the Inventive Gene bgerα

Two μg of expression plasmid pRc/RSV (manufactured by Invitrogen) containing RSV promoter was digested all night at 37° C. with a restriction enzyme Xba I(10U) and then 5 U of alkaline phosphatase (BAP) was reacted at 65° C. for one hour. Electrophoresis was performed on this plasmid using the agarose gel (Agarose S manufactured by Nippon Gene Co. Ltd.) and the DNA was collected from the band with a length of 5 to 6 kbp using Gene Clean (manufactured by Funakoshi Co., Ltd.) for preparing the vector DNA. On the other hand, PCR (30 cycles conducted wherein one cycle involves incubation at 94° C. for one minute, 55° C. for two minute, and then at 74° C. for 2.5 minutes) was performed LA-Taq (manufactured by Takara Shuzo Co., Ltd) using the DNA of the plasmid pBSBGERα obtained in the Example 1(3) as a template and an oligonucleotide comprising the nucleotide sequence of SEQ ID NO: 14 and an oligonucleotide comprising the nucleotide sequence of SEQ ID NO: 15 for amplifying the DNA. The amplified DNA was treated with chloroform/phenol, immersed in ethanol, centrifuged with 70% ethanol for washing and dried, TE added to it for dissolution, and digested at 37° C. for five hours with restriction enzyme XbaI. Then, said digested DNA was separated by electrophoresis using 1% of agarose gel for extracting the gel component containing approximately 1.5 kbp of DNA and the DNA contained in the gel was purified with Gene Clean (manufactured by Funakoshi Co., Ltd.). Approximately 100 ng of the purified DNA was mixed with 50 ng of vector DNA prepared as described above, 5 U of T4 ligase was added to it, and the mixture was incubated at 16° C. for three hours. This reaction cocktail was transduced Into the E. coli DH5α strain competent cell (manufactured by TOYOBO CO., LTD.) in accordance with the supplied instructions and the plasmid DNA was prepared from the colony indicating ampicillin-resistance by the alkali method. The nucleotide sequence of the resultant plasmid DNA was analyzed and the plasmid containing the inventive gene bgerα linked downstream of RSV promoter was termed pRc/RSV-BGERα.

Example 3

Construction of the Inventive Vector for Animal Cell Expression Containing the Inventive Gene bgerα2

Two μg of BGERα expression plasmid pRc/RSV-BGERα prepared in Example 2 was digested all night at 37° C. with restriction enzyme HindIII(10U), and then 5 U of alkaline phosphatase (BAP) was reacted at 65° C. for one hour. Electrophoresis was performed on this plasmid using the agarose gel (Agarose S manufactured by Nippon Gene Co., Ltd.) and the DNA was collected from the band with a length of 5 to 6 kbp using Gene Clean (manufactured by Funakoshi Co., Ltd.) for preparing the vector DNA. On the other hand, PCR (30 cycles conducted wherein one cycle involves incubation at 94° C. for one minute, 55° C. for two minutes, and then at 74° C. for 2.5 minutes) was performed with LA-Taq (manufactured by Takara Shuzo Co., Ltd) using the cDNA prepared in Example 1(4) as a template and an oligonucleotide comprising the nucleotide sequence of SEQ ID NO: 16 and an oligonucleotide comprising the nucleotide sequence of SEQ ID NO: 15 for amplifying the DNA. The amplified DNA was treated with chloroform/phenol, immersed in ethanol, centrifuged with 70% ethanol for washing and dried, TE was added to it for dissolution, and the DNA was digested all night at 37° C. with restriction enzyme HindIII. Then, electrophoresis was performed on the digested DNA for separation using 1% of agarose gel, the gel component containing the DNA with a length of approximately 1.0 kbp was extracted, and the DNA contained in the gel was prepared with Gene Clean (manufactured by Funakoshi Co., Ltd.). Among the DNA, approximately 100 ng of the DNA component was mixed with 50 ng of vector DNA prepared as described above, 5 U of T4 ligase was added to it, and incubated at 16° C. for three hours. This reaction cocktail was transduced into the E. coli DH5α strain competent cell (manufactured by TOYOBO CO., LTD.) in accordance with the supplied instructions and the plasmid DNA was prepared from the colony indicating ampicillin-resistance by the alkali method. The nucleotide sequence of the resultant plasmid DNA was analyzed and the plasmid containing the nucleotide sequence represented by nucleotide numbers 74 to 1819 of SEQ ID NO: 5 at the downstream of RSV promoter was selected and termed pRC/RSV-BGERα2.

Example 4

Reporter Assay Using the Inventive Gene (1) Preparation of a Reporter Plasmid for Reporter Assay Xenopus genome DNA was purified with Isogen reagent (Nippon Gene) in accordance with the supplied manual. With the purified genome DNA as a template, PCR was performed according to the report by Walker et al. (Nucleic acid Res, (1984) 12, 8611-8626) to amplify DNA which includes the sequence from the TATA box upstream of the Xenopus vitellogenin gene to the estrogen receptor response element sequence. The amplified DNA was recovered and then treated with Blunting kit (Takara) to have blunt ends (hereinafter the resulting DNA is referred to as ERE DNA).

Two oligonucleotides (an oligonucleotide comprising the nucleotide sequence of SEQ ID NO:17 and an oligonucleotide comprising the nucleotide sequence of SEQ ID NO:18) each having a nucleotide sequence derived from a nucleotide sequence near the TATA box and a leader sequence of mouse metallothionein I gene (Genbank Accession No. J00605) were allowed to anneal to each other to form a double stranded DNA, both ends of which was then phosphorylated with T4 polynucleotide kinase (hereinafter the resulting DNA is referred to as TATA DNA). Firefly luciferase gene-containing plasmid pGL3 (Promega) was digested with restriction enzymes Bgl II and Hind III and then mixed with Bacterial alkaline phosphatase (BAP) and incubated at 65° C. for 1 hour. The incubated solution was then subjected to electrophoresis using a low melting point agarose (AgaroseL, Nippon Gene), and a Bgl II-Hind III fragment DNA containing the pGL3-derived luciferase gene was recovered. About 100 ng of the recovered DNA and 1 μg of TATA DNA were mixed and ligated with T4 ligase to form plasmid pGL3-TATA. The pGL3-TATA was digested with restriction enzyme Sma I and then mixed with BAP and incubated at 65° C. for 1 hour. The incubated solution was then subjected to low melting point agarose gel electrophoresis, and a DNA was recovered from gel component containing DNA band. About 100 ng of the recovered DNA and about 1 µg of ERE DNA were mixed and allowed to react with T4 ligase. From the reaction solution, the DNA was then introduced into *E. coli* DH5α strain competent cells (TOYOBO). From each of several ampicillin-resistant *E. coli* colonies, a plasmid DNA was prepared. Each prepared DNA was digested with restriction enzymes Kpn I and Xho I, and the resulting digest was analyzed by agarose gel electrophoresis. A plasmid with a structure in which one copy of ERE DNA was introduced in the Sma I site of pGL3-TATA was termed plasmid pGL3-TATA-ERE, and another plasmid with a structure in which five copies of ERE DNA were introduced in the Sma I site was termed plasmid pGL3-TATA-ERE×5.

(2) Reporter Assay Using a Transient Expression Line

Approximately $2\times10^6$ HeLa cells were inoculated on 10 cm plates and incubated in an E-MEM medium containing 10 v/v % of charcoal dextran-treated FBS (hereafter, referred to as FBS) under 5% of $CO_2$ at 37° C. for one day. Then, 3.75 µg of pRc/RSV-BGERα or pRc/RSV-BGERα2 and 3.75 µg of pGL3-TATA-ERE×5 were transduced together into the cells using Lipofectamine (manufactured by Life Technologies Co., Ltd.) in accordance with the protocol supplied with It. It was incubated at 37° C. for 16 hours, the medium was replaced with a new one, and the incubation was continued for further three hours. Then, the cells were collected, suspended in the E-MEM medium containing 10 v/v % of FBS to disperse, and inoculated on 96-well plates with various concentrations of E2 (manufactured by Wako Pure Chemical Industries, Ltd.), diethylstilbestrol (DES)(manufactured by Nacalai Tesque, Inc.), bisphenol A (manufactured by Wako Pure Chemical Industries, Ltd.), genistein (manufactured by Wako Pure Chemical Industries, Ltd.) or o,p'-DDT (Lancaster), all of which were already dissolved with DMSO (final DMSO concentration of 0.1%). In addition, to measure the anti-estrogen activity, the above-mentioned cells were inoculated on the 96-well plates with various concentrations of 4-hydroxytamoxifen and 10 nM E2 added together (final DMSO concentration of 0.1%). The 96-well plates with the cells inoculated on was incubated at 37° C. for approximately 40 hours and an aliquot (50 µl/well) of a cell resolvent PGC50 (manufactured by Nippon Gene Co., Ltd.) diluted to ⅕ concentration was added onto them, and left at room temperature for 30 minutes while carefully shaking them at times to lyse the cells. An aliquot (10 µl) of cell lysate prepared as described above was collected on the white 96-well sample plates (manufactured by BERTHOLD) and luminescence levels were immediately measured for five seconds using a luminometer LB96p with a auto matrix injector (manufactured by BERTHOD) while an aliquot (50 µl/well) of enzyme matrix solution PGL100 (manufactured by Nippon Gene Co., Ltd.) was being added. The result of the use of the cells with pRc/RSV-BGERα2 transduced is shown in FIGS. 1 to 6 and the result of the cells with pRc/RSV-BGERα2 transduced is shown in FIGS. 7 to 11. As described above, the activation ability and anti-activation ability of test substances on estrogen receptor could be measured by the luciferase reporter assay using the inventive gene. In addition, by measuring other test substances in the same manner as that of this substance, substances having the activation ability on estrogen receptor or substances having the anti-activation ability on estrogen receptor can be detected.

(3) Preparation of the Transformant with the Inventive Gene Transduced into its Chromosome for Reporter Assay The plasmid pUCSV-BSD (purchased from Funakoshi) is digested with BamHI to form a DNA coding for a blasticidin S deaminase gene expression cassette. Further, the plasmid pGL3-TATA-ERE obtained in Example 4(1) is digested with BamHI and treated with BAP. DNA coding for a blasticidin S deaminase gene expression cassette was then mixed with the restriction digested pGL3-TATA-ERE×5. The resulting DNA mixture is allowed to react with T4 ligase. The DNA is then introduced from the reaction solution into *E. coli* DH5α competent cells (TOYOBO). An ampicillin-resistant colony is isolated, and a plasmid DNA is prepared from the colony by alkali method. The prepared DNA is digested with restriction enzyme BamHI, and the resulting digest is analyzed by agarose gel electrophoresis. A plasmid with a structure in which the blasticidin S deaminase gene expression cassette is inserted in the BamHI restriction site of plasmid pGL3-TATA-ERE is selected and named plasmid pGL3-TATA-ERE-BSD.

The DNA of produced plasmid pGL3-TATA-ERR-BSD and DNA of an expression vector in which the inventive gene is inserted into pRc/RSV are each linearized and then introduced into human-derived HeLa cells as described in Example 4(2) to obtain a transformant in which these DNAs are introduced into the host cell chromosome.

DNA of plasmid pGL3-TATA-ERE-BSD and DNA of an expression vector in which the inventive gene is inserted into pRc/RSV are each digested with Sal I. HeLa cells are cultured on plates about 10 cm in diameter (Falcon) with a 10 FBS-containing DMEM medium (Nissui Pharmaceutical) at 37° C. under 5% $CO_2$. About $5\times10^5$ cells are cultured for 1 day. The resulting cells are transfected simultaneously with the above linearized DNAs by lipofection method using lipofectin (GIBCO). The lipofection method Is performed according to the manual description attached to the lipofectin under the following conditions: a treating time of 5 hours, the total amount of the linearized DNAs of 7 µg (each 3.5 µg) per plate, and a lipofectin amount of 20 µl/plate. After the lipofection, the cells are cultured in situ in the lot FBS-containing DMEM medium for 3 days. The cells are peeled off from the plate by trypsin treatment and then divided into 10 aliquots, inoculated on 10 plates, respectively, and cultured overnight. G418 (Sigma) is then added to the culture at a final concentration of 400 µg/ml. Blasticidin S is also added to the culture at a final concentration of 8 µg/ml, and the cultivation is further carried out. After one week, the medium is replaced with a fresh one containing G418 and blasticidin S each at the same concentration, and the cultivation is further carried out. After a week, the same process is carried out again. After another week, the plates are observed with an inverted microscope, and 30 colonies with a diameter of several mm are each transferred to each well of a 96-well view plate (Berthold) to which a medium has been added to each well in advance, and the cultivation is further carried out. Before grown in a confluent state, the cells are peeled off by trypsin treatment, collected, divided into 3 aliquots, and inoculated on new 3 96-well view plates, respectively. The cells on one plate are subcultured. E2 is added to one of the remaining two plates at a final concentration of 50 nM, and nothing is added to the other plate. The cells on each plate are cultured for 2 days. After the 2 days, each culture supernatant is removed from each plate, and the cells are washed with 200 µl/well of PBS(−) twice. In order to lyse the cells, cytolytic agent PGC50 (Nippon Gene) 5-fold diluted was then added to each view plate in an amount of 20 μl/well and allowed to stand at room temperature for 30 minutes. The plates are each placed in Luminometer LB96p equipped with an automatic enzyme substrate injector (Berthold). While 50 μl of enzyme substrate solution PGL1000 (Nippon Gene) is automatically added to each well, the luciferase activity is measured. When the luciferase activity of the E2-containing experimental section is at least twice as high as that of the E2-free experimental section, the transformant cells are selected and collected.

(4) Reporter Assay Using the Transformant with the Inventive Gene Transduced into its Chromosome The transformant prepared in Example 4(3) is inoculated on a 24-well plate at a density of about $4 \times 10^4$ cells/well and cultured under 5% $CO_2$ at 37° C. for 1 day in an E-MEM medium containing 10% of charcoal dextran-treated FBS, 400 μg/ml of G418, and 8 μg/ml of blasticidin S (hereinafter referred to as the FBS and antibiotic-containing E-MEM medium). A test substance DMSO (Wako Pure Chemical) solution is added to the FBS and antibiotic-containing E-MEM medium in different amounts so as to provide final test substance concentrations of 1 nM to 50 μM. Alternatively, DMSO is added to the FBS and antibiotic-containing E-MEM medium in the same amount as that of above each test substance solution. Alternatively, a DMSO solution of E2 is added to the FBS and antibiotic-containing E-MEM medium so as to provide an E2 final concentration of 1 μM. The above cell culture supernatant is replaced with each of the above resulting mediums. The cell culture is held in a $CO_2$ incubator for 24 hours, and then the culture supernatant is removed from the plate. While attention is paid not to peel off the adhering cells from the plate, the cells are washed with 1 ml/well of PBS(−) twice. For the purpose of lysing the cells, cytolytic agent PGC50 (Nippon Gene) 5-fold diluted is added to the plate in an amount of 50 μl/well and allowed to stand at room temperature for 30 minutes while sometimes gently shaken. The resulting lysis solution is placed on a 96-well white sample plate (Berthold) in an amount of 10 μl/well. In Luminometer LB96p equipped with an automatic substrate injector (Berthold), enzyme substrate solution PGL100 (Nippon Gene) is added to the plate in an amount of 50 μl/well, and immediately, the luminescence intensity from each well is measured for 5 seconds.

By the luciferase reporter assay using the transformant with the inventive gene transduced into its chromosome as descried above, the test substances containing the substances having the estrogen receptor activating ability can be detected.

Example 5

Two-hybrid System Using the Inventive Gene (1) Preparation of the Vector Containing the Chimera Gene Coding the Fusion Protein of the Ligand Binding Domain of the Inventive BGERα and the DNA Binding Domain of the Transcription Control Factor PCR (30 cycles conducted wherein one cycle involves incubation at 94° C. for one minute, 55° C. for one more minute, and then at 74° C. for 1.5 minutes) was performed with LA-Taq (Takara Shuzo Co., Ltd) using the plasmid pBSBGERα as a template, a primer comprising the nucleotide sequences of SEQ ID NO: 19 and a primer comrising the nucleotide sequences of SEQ ID NO: 20 for amplifying the DNA coding the ligand binding domain of the inventive BEGRα in accordance with the supplied manual.

The amplified DNA was treated with chloroform/phenol and then precipitated with ethanol. The precipitate was centrifugally washed with 70% ethanol and then dried. The DNA was dissolved with TE added and then digested with restriction enzymes EcoRI and SalI at 37° C. for about 5 hours. The digest was subjected to 1% agarose gel electrophoresis and separated. About 1 kbp DNA-containing part of the gel was cut out, and the DNA was recovered from the part using GENECLEAN (Funakoshi). Vector pGBT9 (Clontech) (about 50 ng), for the production of the fusion protein with the DNA binding domain of GAL4 protein, was digested with EcoRI and SalI and then subjected to 1% agarose gel electrophoresis. The EcoRI and SalI-digested vector DNA was then recovered using GENECLEAN (Funakoshi). The recovered vector DNA and about 10 ng of the above recovered DNA were mixed with each other. A ligation solution (Ligation Kit, Takara) was added to the mixture in the same volume and incubated at 16° C. for about 5 hours. The resulting mixture was then introduced into competent DH5α cells (TOYOBO) according to the process description attached to the kit. An ampicillin-resistant colony was isolated, and a plasmid DNA was prepared from the colony by alkali method. The nucleotide sequence of the prepared plasmid DNA was confirmed and then named pGBT9-BGERαLID. This plasmid can be applied to the two-hybrid assay using the budding yeast as the host cell.

(2) Preparing the Vector Containing the Chimera Gene Coding the Fusion Protein of the Receptor Binding Domain of the Transcription Coupling Factor and Transcrioption Activating Domain of the Transcription Coupling Factor A cDNA was produced using a human brain-derived mRNA (Clontech) and RT-PCR kit (Takara) in accordance with the protocol attached to the products. PCR was performed using the produced cDNA as a template, using an oligonucleotide comprising the nucleotide sequence of SEQ ID NO:21 and an oligonucleotide comprising the nucleotide sequence of SEQ ID NO:22 as primers and using LA-Taq (Takara) (the PCR reaction conditions: 30 cycles of 94° C. for 1 minute, 55° C. for 1 minute, and 72° C. for 2.5 minutes). The PCR amplified a DNA coding for the amino acid sequence between amino acids 624 and 1287 from the amino terminal end of transcription coupling factor TIF2. The amplified DNA was treated with chloroform/phenol and then precipitated with ethanol. The precipitate was centrifugally washed with 70% ethanol and then dried. The DNA was dissolved with TE added and then digested with restriction enzymes EcoRI and BglII at 37° C. for 5 hours The digest was subjected to 1% agarose gel electrophoresis and separated. About 2.0 kbp DNA-containing part of the gel was cut out, and the DNA was recovered from the part using GENECLEAN (Funakoshi). Vector pGAD424 (Clontech) (about 50 ng), for the production of the fusion protein with the transcription activating domain of GAL4 protein, was digested with EcoRI and BamHI and then subjected to 1% agarose gel electrophoresis. The EcoRI and BamHI-digested vector DNA was then recovered using GENECLEAN (Funakoshi). The recovered vector DNA and about 10 ng of the above-recovered DNA were mixed with each other. A ligation solution (Ligation Kit, Takara) was added to the mixture in the same volume and incubated at 16° C. for about 1 hour. The resulting mixture was then introduced into *E. coli* DH5α competent cells (TOYOBO) according to the process description attached to the kit. An ampicillin-resistant colony was isolated, and a plasmid DNA was prepared from the colony by alkali method. The nucleotide sequence of the prepared plasmid DNA was confirmed and then named pGAD424-TIF2RID. This plasmid can be applied to the two-hybrid assay using the budding yeast as the host cell.

(3) Preparing the Two-hybrid System Using Budding Yeast Cells as Host Cells

Yeast Y190 (Clontech) was shake-cultured in YPD medium at 30° C. overnight according to the manual of Matchmaker Two-hybrid System (Clontech). The cultured yeast cells were collected and then transfected with pGBT9-BGERαLID obtained in Example 5(1) and pGAD424-TIF2RID obtained in Example 5(2) using Yeastmaker yeast transformation system (Clontech). The two plasmid-introduced yeast cells were inoculated on a tryptophan or leucine-free SD nutrient agar and cultured at 30° C. for about 2 days. After the culture was completed, 3 grown colony were selected, applied again on the tryptophan or leucine-free SD nutrient agar, and cultured at 30° C. for about 2 days. The cultured yeast is used for the two-hybrid system.

Figure 12:
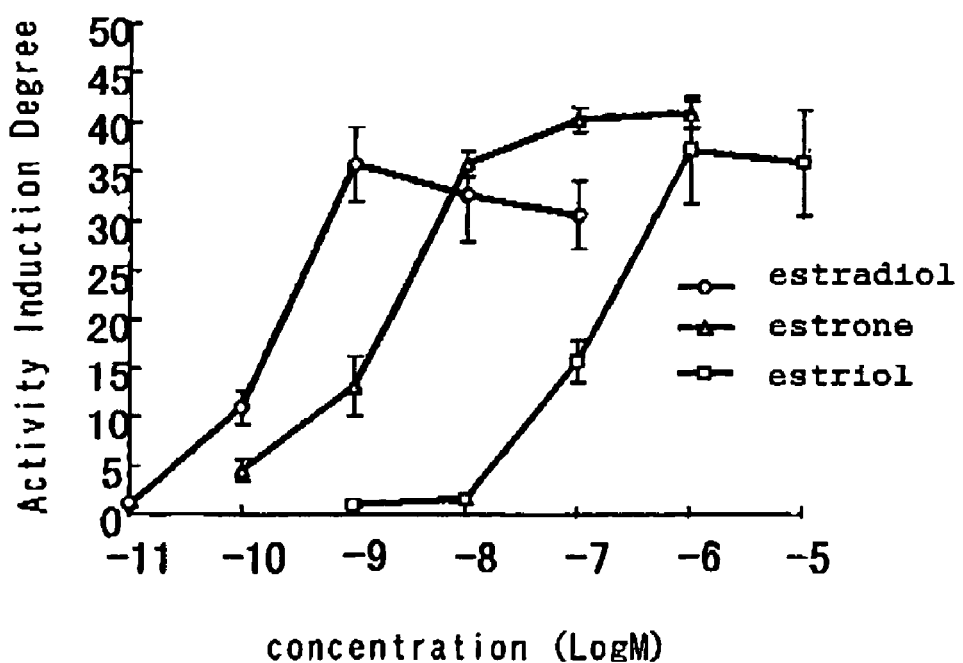
FIG. 12 is a diagram showing a result of measuring the ability of E2, estrone and estriol to activate the estrogen receptor activity by the two-hybrid system using the inventive gene, bger α (N=4). Along the abscissa axis, the concentration of test compounds are annotated. Along the ordinate axis, the β-galactosidase activity value is shown, where the β-galactosidase activity value of the test compound-free section is normalized as 1.
Figure 1:
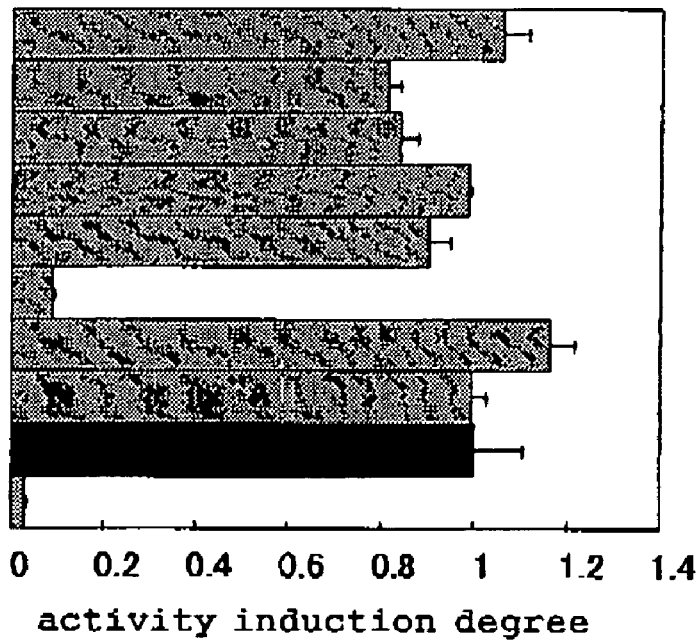
Figure 1:
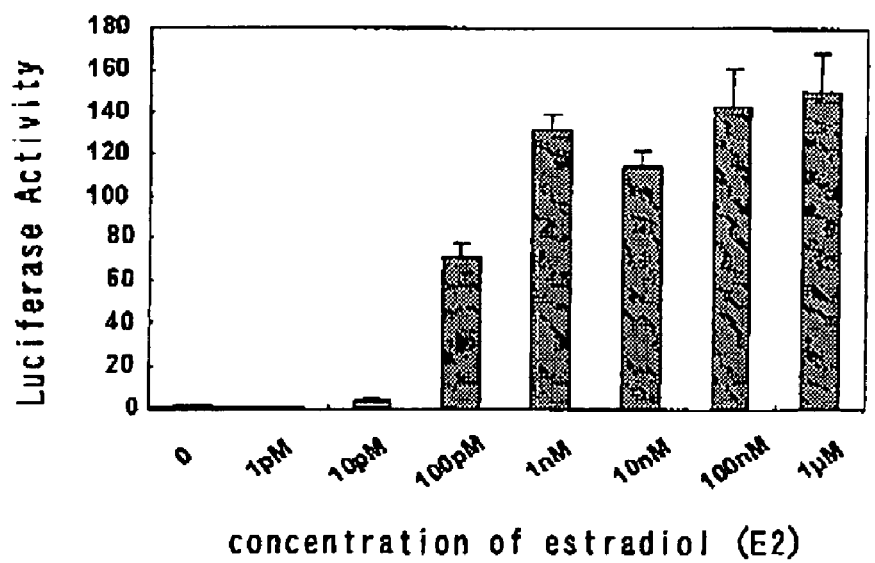
Figure 15:
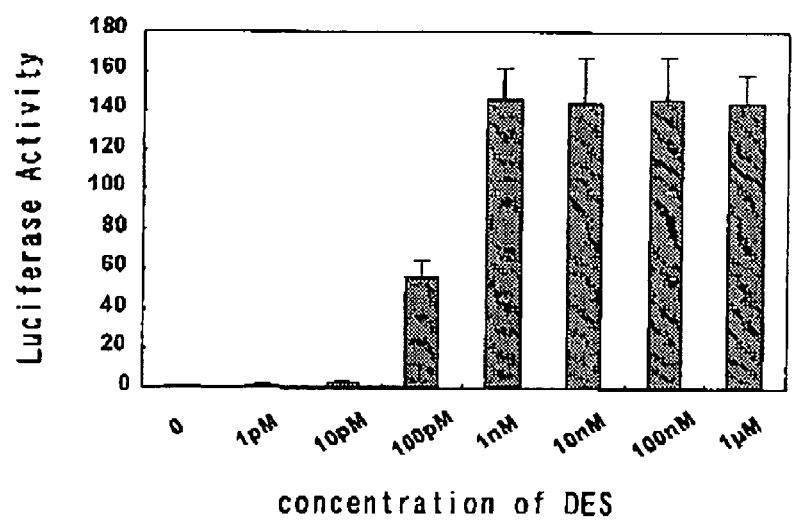
FIG. 15 is a diagram showing a result of measuring the ability of diethylstilbestrol (DES) to activate the estrogen receptor activity by the reporter assay using the inventive gene, bger β. Along the abscissa axis, the concentration of DES are annotated for each experimental section. The left end column indicated by O corresponds to an experimental section in which DMSO was added at a final concentration of 0.1% in place of the DMSO solution of DES (DES-free section). Along the ordinate axis, the luciferase activity value is shown, where the luciferase activity value of the DES-free section is normalized as 1.
Figure 16:
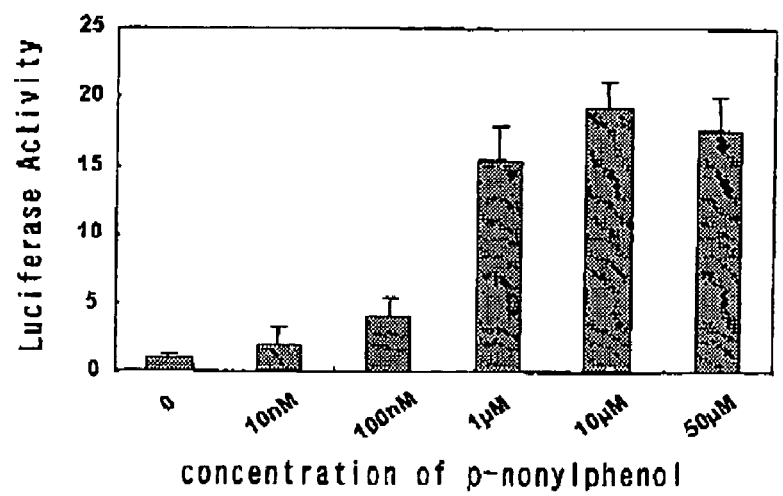
FIG. 16 is a diagram showing a result of measuring the ability of p-nonylphenol to activate the estrogen receptor activity by the reporter assay using the inventive gene, bger β. Along the abscissa axis, the concentration of p-nonylphenol are annotated for each experimental section. The left end column indicated by O corresponds to an experimental section in which DMSO was added at a final concentration of 0.1% in place of the DMSO solution of p-nonylphenol (p-nonylphenol-free section). Along the ordinate axis, the luciferase activity value is shown, where the luciferase activity value of the p-nonylphenol-free section is normalized as 1.
Figure 17:
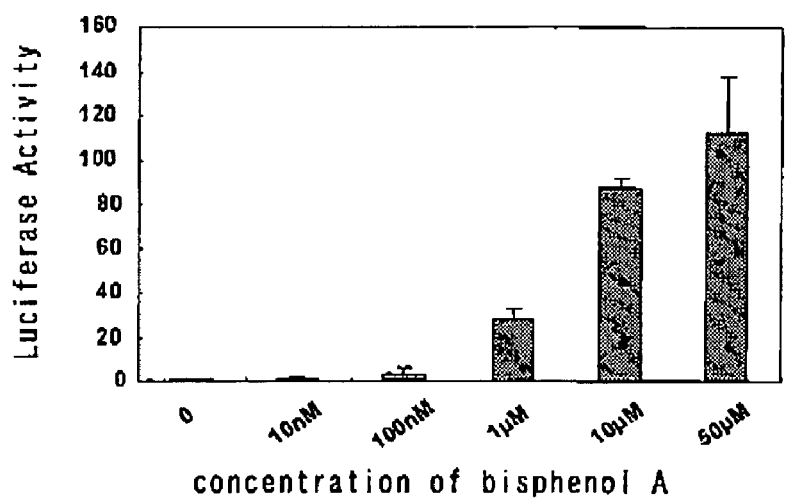
FIG. 17 is a diagram showing a result of measuring the ability of bisphenol A to activate the estrogen receptor activity by the reporter assay using the inventive gene, bger β. Along the abscissa axis, the concentration of bisphenol A are annotated for each experimental section. The left end column indicated by O corresponds to an experimental section in which DMSO was added at a final concentration of 0.1% in place of the DMSO solution of bisphenol A (bisphenol A-free section). Along the ordinate axis, the luciferase activity value is shown, where the luciferase activity value of the bisphenol A-free section is normalized as 1.
Figure 18:
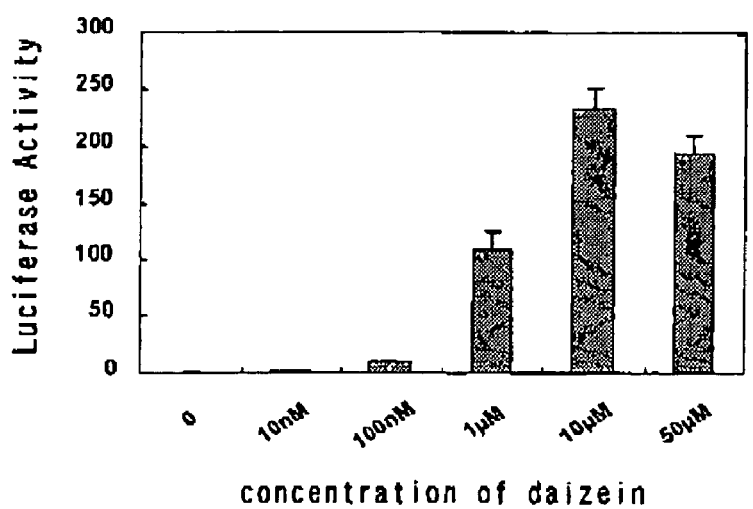
FIG. 18 is a diagram showing a result of measuring the ability of daidzein to activate the estrogen receptor activity by the reporter assay using the inventive gene, bger β. Along the abscissa axis, the concentration of daidzein are annotated for each experimental section. The left end column indicated by O corresponds to an experimental section in which DMSO was added at a final concentration of 0.1% in place of the DMSO solution of daidzein (daidzein-free section). Along the ordinate axis, the luciferase activity value is shown, where the luciferase activity value of the daidzein-free section is normalized as 1.
Figure 19:
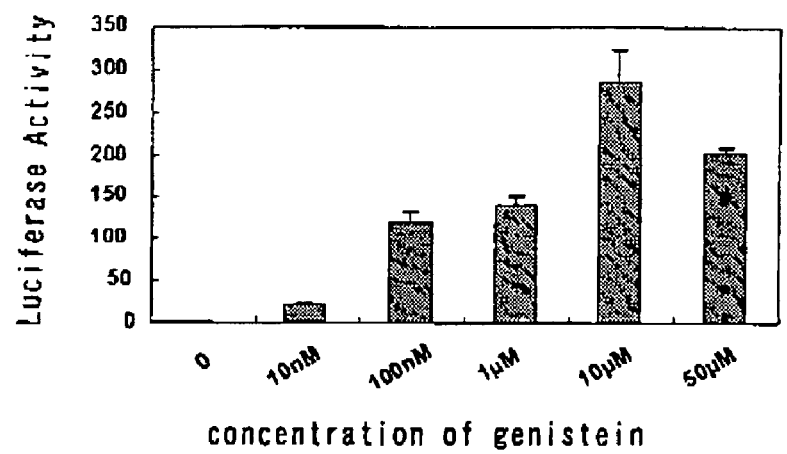
FIG. 19 is a diagram showing a result of measuring the ability of genistein to activate the estrogen receptor activity by the reporter assay using the inventive gene, bger β. Along the abscissa axis, the concentration of genistein are annotated for each experimental section. The left end column indicated by O corresponds to an experimental section in which DMSO was added at a final concentration of 0.1% in place of the DMSO solution of genistein (genistein-free section). Along the ordinate axis, the luciferase activity value is shown, where the luciferase activity value of the genistein-free section is normalized as 1.
Figure 20:
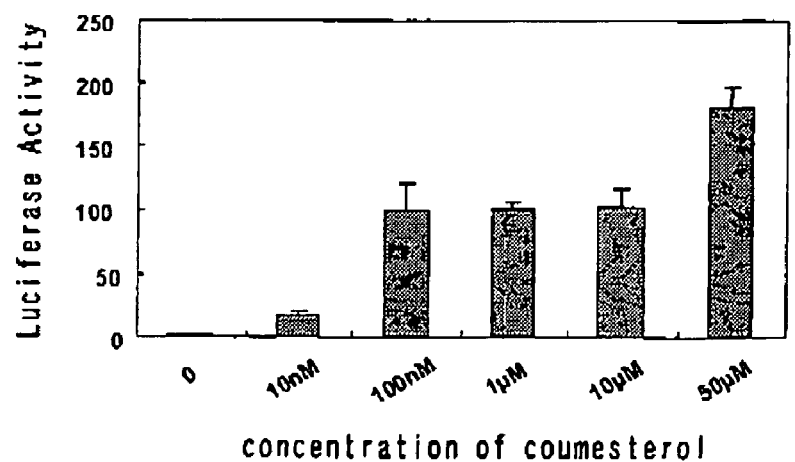
FIG. 20 is a diagram showing a result of measuring the ability of coumesterol to activate the estrogen receptor activity by the reporter assay using the inventive gene, bger β. Along the abscissa axis, the concentration of coumesterol are annotated for each experimental section. The left end column indicated by O corresponds to an experimental section in which DMSO was added at a final concentration of 0.1% in place of the DMSO solution of coumesterol (coumesterol-free section). Along the ordinate axis, the luciferase activity value is shown, where the luciferase activity value of the coumesterol-free section is normalized as 1.
Figure 21:
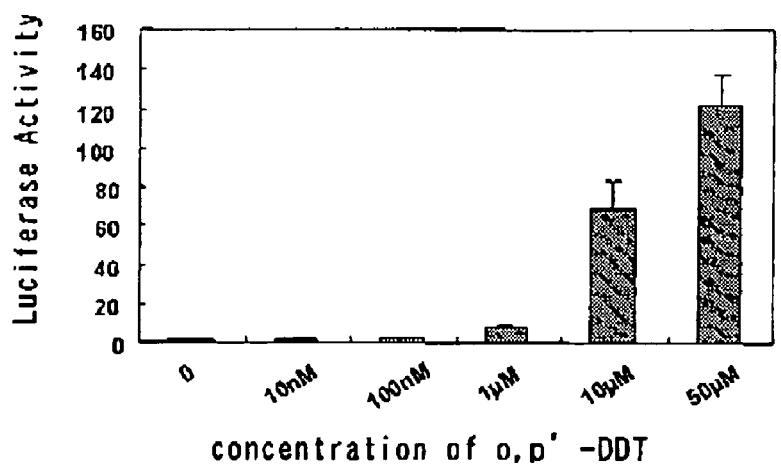
FIG. 21 is a diagram showing a result of measuring the ability of o,p'-DDT to activate the estrogen receptor activity by the reporter assay using the inventive gene, bger β. Along the abscissa axis, the concentration of o,p'-DDT are annotated for each experimental section. The left end column indicated by O corresponds to an experimental section in which DMSO was added at a final concentration of 0.1% in place of the DMSO solution of o.p'-DDT (o,p'-DDT-free section). Along the ordinate axis, the luciferase activity value is shown, where the luciferase activity value of the o,p'-DDT-free section is normalized as 1.
Figure 22:
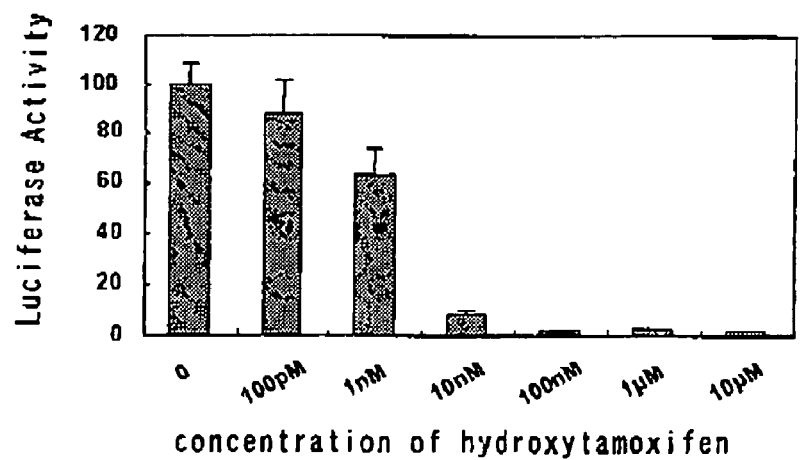
FIG. 22 is a diagram showing a result of measuring the ability of 4-hydroxytamoxifen (4-OH-HTM) to activate the estrogen receptor activity by the reporter assay using the inventive gene, bger β. Along the abscissa axis, the concentration of 4-OH-HTM allowed to coexist with 10 nM of estradiol are annotated for each experimental section. The left end column indicated by O corresponds to an experimental section in which DMSO was added at a final concentration of 0.1% in place of the DMSO solution of 4-OH-HTM (4-OH-HTM-free section). Along the ordinate axis, the luciferase activity value is shown, where the luciferase activity value of the 4-OH-HTM-free section is normalized as 1.

(4) Measuring the Ability of a Test Substance to Regulate Estrogen Receptor Activity using the Yeast Two-hybrid System Part of yeast prepared in the example 5 (3) was inoculated in 1 ml of tryptophan and leucine-free SD medium, incubated at 30° C. all night while shaking, and the resultant culture solution was diluted to approximate 1/80 concentration with the tryptophan and leucine-free SD medium. On the 96-deep well plate, 2.5 µl of various concentrations of E2 (manufactured by Wako Pure Chemical Industries, Ltd.), estriol (manufactured by Wako Pure Chemical Industries, Ltd.), estron (manufactured by Wako Pure Chemical Industries, Ltd.), 1 µm of diethylstilbestrol (DES)(manufactured by Nacalai Tesque, Inc.), 1 mM of bisphenol A (manufactured by Wako Pure Chemical Industries, Ltd.), 100 µm of P-nonylphenol (manufactured by Kanto Kagaku), 100 µm of genistein (manufactured by Wako Pure Chemical Industries, Ltd.), 100 µm of coumesterol (manufactured by INDOFINE Chemical Co., Ltd.), 1 µm of daizein (manufactured by Sigma Corp.), 1 µm of methoxychlor (manufactured by Wako Pure Chemical Industries, Ltd.), or 1 mM of o,p'-DDT (manufactured by Lancaster), all of which were already dissolved with DMSO, was added (final concentration of DMSO of 1%), 150 µl of yeast cultured as described above was further added on them, and they were incubated at 30° C. for four hours while shaking. After incubation, 100 µl of yeast solution from each of the wells was collected, 100 µl of luminoreactive solution for β-galactositase activity measurement (Gal-Screen, manufactured by Tropix Corp.) was added on them, incubated at room temperature for approximate 1.5 hours, and the luminoreactive levels were measured using a luminometer LB96p (manufactured by BERTHOLD). FIG. 12 shows the result of concentration-dependent activity induction of E2 (manufactured by Wako Pure Chemical Industries, Ltd.), estriol (manufactured by Wako Pure Chemical Industries, Ltd.), and estron (manufactured by Wako Pure Chemical Industries, Ltd.). FIG. 13 shows the result of 10 nM (the final concentration) of diethylstilbestrol (DES), 10 µM of bisphenyl A. 1 µM of p-nonylphenol, 1 µM of genistein, 1 µM of coumesterol, 10 µM of daizein, 10 µM of methoxychlor, and 10 µM of o,p'-DDT.

Example 6

Preparing the Recombinant Virus Vector and Recombinant Virus Particles Containing the Inventive Gene Two µg of DNA of the inventive vector pRc/RSV-BGERα was digested with 10 U of the restriction enzyme XbaI and 2 µg of DNA of pRc/RSV-BGERα2 with 10 U of restriction enzyme HindIII, respectively at 37° C. for one hour, electrophoresis was performed on them using the low melting-point agarose gel, and approximately 1.5 to 1.7 kbp of DNA fragments were collected. Among pRc/RSV-BGERα2-derived DNA, approximately 1 µg of DNA component was treated using the DNA blunting kit (manufactured by Takara Shuzo Co., Ltd) to have blunt ends, and reacted with T4 polinucleotidekinese to have phosphorylated ends. Said DNA was treated with phenol, purified by ethanol sedimentation, and all the quantity of sedimented DNA was used as a insert DNA for preparing the following expression plasmid. On the other hand, 2 µg of pVL1392 vector DNA was digested with 10 U of restriction enzyme XbaI or SmaI, treated with 10 U of alkaline phosphatase at 65° C. for one hour, electrophoresis was performed on it using the low melting-point agarose gel, and the DNAs were collected for using as pVL1392-XbaI and pVL1392-SmaI, respectively. Approximately 100 ng of 1.5 kbp DNA prepared from pRc/RSV-BGERα as mentioned above was added to 100 ng of pVL1392-XbaI vector DNA prepared here, and incubated with 5 U of T4 ligase at 16° C. for three hours. This was transduced into the *E. coli* DH5α strain competent cells (manufactured by TOYOBO CO., LTD.) in accordance with the supplied instructions, and the plasmid DNAs were prepared from the resultant colony by the alkaline method. Approximately 1 µl of plasmid DNA samples were digested with 10 U of restriction enzyme XbaI at 37° C. for one hour, electrophoresis was performed on it using Agarose S (manufactured by Nippon Gene Co., Ltd.) for analysis, and clones were screened so that approximately 1.5 kbp of BAND would be detected. In addition. 100 ng of approximately 1.7 kbp of DNA prepared from pRc/RSV-BGERα2 as mentioned above was added to 100 ng of pVL1392-SmaI vector DNA, and incubated under the mediation of 5 U of T4 ligase at 16° C. for three hours. This was transduced into the *E. coli* DH5α strain competent cells (manufactured by TOYOBO CO., LTD.) in accordance with the supplied instructions and plasmid DNAs were prepared from the resultant colony by the alkaline process. Approximately 1 µg of plasmid DNA samples were digested with 10 U of restriction enzymes XbaI and HindIII, respectively at 37° C. for one hour, electrophoresis was performed on them using Agarose S (manufactured by Nippon Gene Co., Ltd.) for analysis, the plasmids were screened so that approximately 1.7 kbp of band would be selected. Said plasmid DNAs were prepared by the alkaline method for using as transfer vectors pVL1392-EGERα and pVL1392-BGERα2 for preparing recombinant Baculo virus.

To a 75 cm² T-flask (Falcon) are added 1×10⁶ of Sf21 cells (available from ATCC), and cultured at 27° C. overnight using a Grace's medium containing 10% FBS and 2% Yeastlate (hereinafter referred to as the FBS-containing Grace medium). To 100 µl of the Grace's medium are added 10 µg of the produced transfer vector pVL1392-BGERα DNA or pVL1392-BGERα2 DNA and 20 ng of linearized viral genome DNA Baculo gold (Pharmingen). After 10 µl of lipofectin (GIBCO) 2-fold diluted with water is further added to the medium, the medium (the lipofectin-DNA mixture solution) is allowed to stand at room temperature for 30 minutes. After the overnight culture, the supernatant is removed from the Sf21 cell culture. The cells are washed with a small amount of a serum-free Grace's medium. To the cells is then added 5 ml of the same medium. The whole amount of the lipofectin-DNA mixture solution is then added to the cells, which is incubated 27° C. for 3 hours. The cells are then washed with the FBS-containing Grace medium. To the cells is also added 20 ml of the FBS-containing Grace medium, and the cells are cultured at 27° C. for 5 days. Day five of the culture, the supernatant is collected in a 50 ml centrifuge tube and centrifuged at 5000×g for 15 minutes to have cell debris precipitated, and then the centrifuged supernatant is collected. The whole amount of the collected supernatant is centrifuged at 100,000×g for 24 hours to give precipitated viral particles that contain the inventive gene. The precipitate is suspended in 100 µl of TE. An equivalent amount of TE-saturated phenol is added thereto and gently mixed at room temperature for 24 hours. After the mixture is centrifuged at 10,000×g for 10 minutes, a water layer is collected. An equivalent amount of chloroform is added to the collected water layer and gently mixed for 10 minutes. The mixture is again centrifuged at 10,000×g for 10 minutes, and then the water layer is collected. To the collected water layer are added NaCl at a final concentration of 0.2 M and a 2.5-fold amount of ethanol, and a viral vector DNA that contains the inventive gene is precipitated and collected.

Example 7

Preparing the Transformant in which the Recombinant Virus Vector of the Present Invention was Transduced into Sf21 Cell and Manufacturing the Estrogen Receptor of the Present Invention To each of ten 75 cm$^2$ T-flasks (Falcon) is added 1×10$^6$ of Sf21 cells (available from ATCC), and cultured in the FBS-containing Grace medium at 27° C. In each flask, 10 µl/flask of the culture supernatant, which is prepared in Example 6 and contains the inventive gene-containing recombinant viral particles, is added to the cells, which are cultured in situ for 4 days. The culture supernatant is harvested from each flask and then added to Sf21 cells, which are similarly cultured in each of ten 75 cm$^2$ T-flasks (Falcon), in an amount of 1 ml per flask. The cells are cultured for 60 hours in each flask and then suspended by pipetting and harvested from each flask. The resulting call suspension is centrifuged at 5,000×g for 15 minutes to have the cells precipitated. The precipitate is suspended in a buffer comprising 20 mM HEPES pH 7, 1 mM EDTA, 1 mM DTT, and 0.5 mM PMSF, and then the suspension is homogenized with 30 up-and-down strokes in a Dounce homogenizer to form a cell homogenate. The homogenate is centrifuged at 30,000×g for 1 hour, and the supernatant fraction is collected to give a fraction that contains the inventive estrogen receptor.

Example 8

Receptor Binding Assay

A binding reaction buffer is prepared to have a final composition of 20 mM HEPES-KOH pH 7.9, 10 mM sodium molybdate, 1 mM DTT, 0.5 mM EDTA, and 0-5 mM PMSF. The reaction solution has a total volume of 100 µl, To the binding reaction buffer are added a 10 µg protein equivalent of the inventive estrogen receptor-containing cell extract and tritium-labeled E2 (which may hereinafter be referred to as the labeled E2) at a content of 1 pM to 100 nM. In the group for determining nonspecific binding, unlabeled E2 is further added at a final concentration of 10 µM to form a reaction solution.

The binding reaction is carried out as follows. After the reaction solution is held on ice for 15 hours, 100 µl of a charcoal dextran liquid (composition: 10 mM Tris-HCl, 0.2% acid-washed active carbon (NoritA, Nacalai Tesque), and 0.005% Pharmacia Dextran T70) is added, and the reaction mixture is allowed to stand on ice for 10 minutes. The reaction mixture is centrifuged at 1,000×g for 10 minutes in a low-speed centrifuge to have the active carbon precipitated, and then 100 µl of the supernatant is sampled The radioactivity of the sampled supernatant is measured using a liquid scintillation counter. Based on the measured value, the amount of the labeled E2 in the supernatant is determined, which corresponds to the amount of the labeled E2 bound to the estrogen receptor (the amount of the bound form of the labeled ligand). In the experimental section to which only the labeled E2 is added, the amount of the bound form of the labeled ligand corresponds to the total amount of the labeled E2 bound to the estrogen receptor (the total binding amount). In the experimental section to which the labeled E2 and unlabeled E2 are added, the amount of the bound form of the labeled ligand corresponds to the amount of the labeled E2 nonspecifically bound to the receptor (the nonspecific binding amount). As for each of the experimental sections to which the labeled E2 is added at different concentrations, respectively, the nonspecific binding amount is subtracted from the total binding amount to produce the amount of the labeled ligand specifically bound to the estrogen receptor (the specific binding amount) in each group. Thereafter, the value of (the concentration of the labeled ligand specifically bound)/(the concentration of the free form of the labeled ligand) is plotted against the Y-axis, and the concentration of the labeled ligand specifically bound is plotted against the X-axis. The Scatchard analysis is performed to produce a Kd value of the inventive estrogen receptor with respect to E2.

In order to determine the affinity of a test substance for the inventive estrogen receptor, the test substance is added at a final concentration of about 1% to the binding assay reaction solution, which contains about 1 nM of the labeled E2 similarly to the above. In the test substance-free experimental section, the same amount of solvent is added to the reaction solution in place of the test substance. When the addition of the test substance reduces the amount of the labeled E2 bound to the estrogen receptor, the test substance is determined as an estrogen receptor binding substance.

Example 9

Obtaining the Inventive Gene

From liver tissue of bluegill, total RNA was prepared in accordance with the phenol-chloroform-isoamyl alcohol technique (Plant Cell Physiol. 36(1): pp85-93(1995)). The yield of the total RNA was approximately 2.8 mg. From approximately 500 µg of the total RNA, poly(A)$^+$RNA was prepared using Oligotex(dT)$_{30}$-Super(manufactured by Takara Shuzo Co., Ltd.). The yield of poly(A)$^+$RNA was approximately 10 µg. Then, a cDNA library was prepared in accordance with the Gubler and Hoffman method. In this step, first, single-stranded cDNAs were synthesized using 2.4 µg of poly(A)$^+$RNA, Oligo(dT)$_{18}$-linker primer ((GA)$_{10}$ACGCGTCGACTCGAGCGGCCGCGGACCG(T)$_{18}$, contaning an XhoI recognition sequence), RAV-2 RTase (manufactured by Takara Shuzo Co., Ltd.) and SuperScriptII RTase (manufactured by Gibco-BRL) and by adding 5-methyl dCTP. Double-strand cDNA was synthesized from the resultant single-stranded cDNA and the both ends of the synthesized double-stranded cDNA were made blunt, at which an EcoRI-NotI-BamHI adaptor (code 4510 manufactured by Takara Shuzo Co., Ltd.) was ligated. Said DNA was digested with a restriction enzyme XhoI and dispensed in a spin column to separate low molecular weight DNA components, and ligated with λZAPII digested with EcoRI and XhoI. Using the resultant DNA and the in vitro packaging kit (manufactured by Stratagene Inc.), in vitro packaging was performed to obtain a cDNA library. Using *E. coli* XL1 Blue MRF' strain (manufactured by Stratagene Inc.) as a host cell, said cDNA library was titrated, estimating that the content of the insert was approximately 95% based on the appearnce rates of blue and white colonies, respectively.

An oligonucleotide comprising the nucleotide sequence of SEQ ID NO: 28 and an oligonucleotide comprising the nucleotide sequence of SEQ ID NO: 29 were synthesized. PCR (30 cycles conducted wherein one cycle involves incubation at 94° C. for one minute. 55° C. for one more minute, and then at 74° C. for 2.5 minutes) was performed using said oligonucleotides as primers and the cDNA prepared as described above as a template. Approximately 1 kbp of amplified DNA was subcloned into a TA cloning vector prepared using a EcoRV site of pBluescriptIISK(+) vector (manufactured by Stratagene Inc.) and the nucleotide sequence of the DNA inserted into the vector was analyzed. Based on the result of the analysis, the DNA comprising the nucleotide sequence of SEQ ID NO: 3 was obtained. Approximately 2 μg of the DNA of the vector having said DNA inserted was digested with restriction enzymes EcoRI and SalI, underwent 1% of agarose gel electrophoresis for separation, and approximately 1 kb of DNA was collected from the gel. By directly labeling the resultant DNA with a thermostable alkaline phosphatase using the AlkPhos Direct system (manufactured by Amersham Pharmacia Biotech Inc. Inc.), the probe was prepared.

The cDNA library prepared as described above was introduced into *E. coli* XL1 Blue MRF' strain and an aliquot of approximately 50,000 clones was plated on each of LB plates (1% Bacto-Triptone, 0.5 Yeast extract, 0.5% NaCl, 1.5% agar) with 150 mm in diameter to form plaques. A total of six these plates were prepared for making screening on 300,000 clones as described below. From the individual plates, phage DNA was moved onto the Hybond N+ membranes (manufactured by Amasham Pharmacia Biotech), and said membranes were immersed in a denaturing solution (1.5 M NaCl, 0.5 N NaOH) for five minutes and then in a neutralizing solution (1.5 M NaCl, 0.5 M Tris-HCl(pH 7.2), 1 mM EDTA) for ten minutes, and dried. These membranes were incubated at 80° C. for two hours and then using the above-mentioned probe, screening was made by hybridization in accordance with the AlkPhos Direct system protocol. Namely, the above-mentioned membranes were immersed in the hybridization solution containing 0.5 M NaCl (manufactured by Amasham Pharmacia Biotech, 5 ng probe/ml) and incubated at 55° C. for 16 hours. Then, the membranes were washed in a primary washing buffer (50 mM sodium phosphate buffer (pH 7.0) containing 2 M urea, 0.1% SDS, 150 mM NaCl, 1 mM $MgCl_2$, and 0.2% blocking reagent) at 60° C. for ten minutes and then incubated in the primary washing buffer at 65° C. for ten minutes again. Moreover, they were washed in a secondary washing buffer (50 mM sodium phosphate buffer containing 100 mM NaCl and 2 mM $MgCl_2$) at room temperature for five minutes twice. On the washed membranes, an attempt of detecting any signals was made using CDP-Star contained in the AlkPhos Direct system as a substrate and a chemiluminescent analyzer with an alkaline phosphatase enzyme. For films, Hyperfilm ECL (manufactured by Amarsham Pharmacia Biotech) was used. Ten positive clones with strong signal were individually selected, collected using sterilized chips, suspended in a SM buffer (50 mM Tris-HCl (pH 7.5), 100 mM NaCl, $MgSO_4.H_2O$, 0.01% gelatine), and kept at 4° C. Said positive clones were cultivated, and an aliquot of approximately 1,000 to 1,500 clones was plated on each of LB plates with approximately 90 mm in diameter (a total of ten plates) for forming plaques, and in the same manner as that mentioned above, screening was made by hybridization. As a result, a positive signal was detected on one clone, which was collected as a positive clone. From the vector contained in said positive clone, plasmid where the DNA inserted into said vector was cloned between the EcoRI and XhoI sites of pbluescript SK(−) was obtained using the in vivo excision system in accordance with the protocol supplied with the λZAPII vector kit (manufactured by Stratagene Inc.). On the DNA cloned into said plasmid, nucleotide sequence analysis was made using the Primer Walking technique. The result of the analysis showed that said DNA contained the nucleotide sequence represented by nucleotide numbers 484 to 2186 of SEQ ID NO: 24.

Example 10

Obtaining Full Length of cDNA by the 5'-RACE Method

Since the full length of cDNA needed to be obtained based on the sequencing information on plasmids cloned into the the EcoRI and XhoI sites of pBluescript SK(−) obtained in the Example 9, 5'-RACEkit (5'-RACE System for Rapid Amplification of cDNA Ends Version 2.0, manufactured by Life Technologies Co., Ltd.) was used for determining the 5' terminal sequence. First, total RNA were extracted from liver of bluegill using the Trizol reagent (manufactured by Life Technologies Co., Ltd.) in accordance with the manual supplied with the product. A single-stranded cDNA was prepared using approximately 5 μg of whole DNA and the oligonucleotide comprising the nucleotide sequence of SEQ ID NO: 38 in accordance with the manual supplied with the product. The cDNA was purified using the GlassMAX column and oligdC-tail was added to the 5' terminal of said DNA using terminal deoxynucleotidyl transferase and dCTP in accordance with the manuals supplied with the products. Then, PCR (30 cycles conducted wherein one cycle involves incubation at 94° C. for one minute, 55° C. for one more minute, and then at 74° C. for 2.0 minutes) was performed using the cDNAs with the oligdC-tail added, 5'RACE Abridged Anchor Primer supplied with the product, and the oligonucleotide comprising the nucleotide sequence of SEQ ID NO: 39 in accordance with the conditions described in the manuals supplied with the products. Subsequently, PCR (30 cycles conducted wherein one cycle involves incubation at 94° C. for one minute, 55° C. for one more minute, and then at 74° C. for 2.0 minute) was performed using 1 μl of said PCR product, Universal Amplification Primer supplied with the product, and the oligonucleotide comprising the nucleotide sequence of SEQ ID NO: 40 in accordance with the conditions described in the manuals supplied with the products. Electrophoresis was performed on the amplified PCR product using 1% of agarose gel (Agarose L, manufactured by Nippon Gene Co., Ltd.), the band was extracted and purified with phenol, cloned using the T vector (pGEM-T, manufactured by Promega Corp.) in accordance with the manual supplied with the manual, and sequencing was made. As a result, the PCR fragments containing the nucleotide sequence of SEQ ID NO: 41 were confirmed. Furthermore, PCR (30 cycles conducted wherein one cycle involves incubation at 94° C. for one minute, 55° C. for one more minute, and then at 74° C. for 2.0 minutes) was performed using the cDNA with oligdc-tall added based on the nucleotide sequences of SEQ ID NO: 41, 5' RACE-Abridged Anchor Primer supplied with the product, and the oligonucleotide comprising the nucleotide sequence of SEQ ID NO: 42 in accordance with the conditions described in the manuals supplied with the products. Besides, PCR (30 cycles conducted wherein one cycle involves incubation at 94° C. for one minute, 55° C. for one more minute, and then at 74° C. for 2.0 minutes) was performed using 1 μl of said PCR product, Universal Amplification Primer supplied with the product, and the oligonucleotide comprising the nucleotide sequence of SEQ ID NO: 43 in accordance with the conditions described in the manuals supplied with the products. Electrophoresis was performed on the amplified PCR product using 1% of agarose gel (Agarose L, manufactured by Nippon Gene Co., Ltd.), the band was extracted and purified with phenol, subcloned using the T vector (pGEM-T, manufactured by Promega Corp.) in accordance with the manuals supplied with the products and the sequence of the obtained clones was confirmed. As a result, the sequences of said PCR product was the nucleotide sequence of SEQ ID NO: 44. PCR (30 cycles conducted wherein one cycle involves incubation at 94° C. for one minute, 55° C. for one more minute, and then at 74° C. for 2.0 minutes) was performed using the oligonucleotide using the 5' terminal sequence (SEQ ID NO: 45) of the PCR product and the oligonucleotide composed of the nucleotide sequence of SEQ ID NO: 46 in accordance with the manual supplied with LA-Taq (manufactured by Takara Shuzo Co., Ltd.), electrophoresis was performed using 1% of agarose gel (Agarose L, manufactured by Nippon Gene Co., Ltd.), approximate 1.7 kbp of PCR product band was extracted and purified with phenol, and the 5' terminal sequence was confirmed by the direct sequencing method. As a result, it was clarified that the DNA of the present invention bgerβ had the nucleotide sequence of SEQ ID NO: 24. In addition, 1.7 kbp of PCR fragments mentioned above were subcloned into the E. coli DH5α using the T vector (pGEM-T, manufactured by Promega Corp.) in accordance with the manual supplied with the product and the plasmid clone whose sequence was confirmed was termed pGEM-BGERβ (hereafter, the estrogen receptor contaning the amino acid sequences of SEQ) ID NO: 23 is simply referred to as BGERβ and the gene coding said estrogen receptor to as the inventive gene bgerβ). This plasmid pGEM-BGERβ was deposited under the deposit number of FERM BP-7199 in International Patent Organism Depositary (IPOD), National Institute of Advanced Industrial Science and Technology, Chuo 6$^{th}$, Higashi 1-1, Tsukuba, Ibaraki (Japan), postal code 305-8566) in 28 Jun. , 1999 in accordance with Budapest Treaty.

Experimet 11

Constructing the Inventive bgerβ Vector for Animal Cell Expression

2 μg of expression plasmid pRc/RSV (Invitrogen Corp.) having the RSV promoter was digested all night at 37° C. with the restriction enzyme Hind III (10U) and Xba I (10U). Electrophoresis was performed on it using the agarose (Agarose S, manufactured by Nippon Gene Co. Ltd.), the DNAS were collected from band component of 5 to 6 kbp Ltd.) for using as the vector DNAs. On the other hand, total RNA was prepared from liver of bluegill using the Trizol reagent (manufactured by Life Technologies Co., Ltd.) in accordance with the manual supplied with the reagent product, and the cDNA was produced using THERMOSCRIPT RT-PCRkit (manufactured by Life Technologies Co., Ltd.) and the random primer supplied with the kit in accordance with the manual supplied with the kit. PCR (30 cycles conducted wherein one cycle involves incubation at 94° C. for one minute, 55° C. for one more minute, and then at 74° C. for 2.5 minutes) was performed with LA-Taq (manufactured by Takara Shuzo Co., Ltd.) using said cDNA as a genetic template and the oligonucleotide comrising the nucleotide sequence of SEQ ID NO: 47 and the oligonucleotide sequence of SEQ ID NO: 48 for amplifying the DNA of the inventive bgerβ. This was treated with chloroform/phenol, sedimented in ethanol, centrifuged with 70% ethanol for washing and dried, TE was added for dissolution, subcloned using the T vector (pGEM-T, manufactured by Promega Corp.) in accordance with the manual supplied with the product, and the sequences of the obtained clones were confirmed. The plasmid clones were digested with restriction enzymes Hind III and XbaI at 37° C. for five hours. Then, the digested clones were separated by electrophoresis using 1% of agarose gel, the gel component containing approximately 1.7 kbp of DNA was extracted, and the DNA contained in the gel component was purified using Gene Clean (manufactured by Funakoshi Co., Ltd.). Approximately 100 ng of DNA was mixed with approximate 50 ng of vector DNA prepared as mentioned above, and ligated all night at 16° C. using Ligation kit ver.2 (manufactured by Takara Shuzo Co., Ltd.). The DNA in the reaction solution was transduced into the E. coli DH5α strain competent cells (manufactured by TOYOBO CO., LTD.) in accordance with the instructions supplied with the product, and the plasmid DNA was prepared from the colony indicating ampicillin-tolerant by the alkaline method. The nucleotide sequences of the resultant plasmid DNA were analyzed and said plasmid which expressed the inventive gene bgerβ was termed pRc/RSV-BGERβ.

Example 12

Preparation of Reporter Plasmid for Reporter Assay

Xenopus genome DNA was purified with Isogen reagent (Nippon Gene) in accordance with the supplied manual. With the purified genome DNA as a template, PCR was performed according to the report by Walker et al. (Nucleic acid Res. (1984) 12, 8611-8626) to amplify DNA which includes the sequence from the TATA box upstream of the Xenopus vitellogenin gene to the estrogen receptor response element sequence. The amplified DNA was recovered and then treated with Blunting kit (Takara) to have blunt ends (hereinafter the resulting DNA is referred to as ERE DNA).

Two oligonucleotides (an oligonucleotide comprising the nucleotide sequence of SEQ ID NO:32 and an ollgonucleotide comprising the nucleotide sequence of SEQ ID NO:33) each having a nucleotide sequence derived from a nucleotide sequence near the TATA box and a leader sequence of mouse metallothionein I gene (Genbank Accession No. J00605) were allowed to anneal to each other to form a double stranded DNA, both ends of which was then phosphorylated with T4 polynucleotide kinase (hereinafter the resulting DNA is referred to as TATA DNA). Firefly luciferase gene-containing plasmid pGL3 (Promega) was digested with restriction enzymes Bgl II and Hind III and then mixed with Bacterial alkaline phosphatase (BAP) and incubated at 65° C. for 1 hour. The incubated solution was then subjected to electrophoresis using a low melting point agarose (AgaroseL, Nippon Gene), and a Bgl II-Hind III fragment DNA containing the pGL3-derived luciferase gene was recovered. About 100 ng of the recovered DNA and 1 μg of TATA DNA were mixed and ligated with T4 ligase to form plasmid pGL3-TATA. The pGL3-TATA was digested with restriction enzyme Sma I and then mixed with SAP and incubated at 65° C. for 1 hour. The incubated solution was then subjected to low melting point agarose gel electrophoresis, and a DNA was recovered from gel component containing DNA band. About 100 ng of the recovered DNA and about 1 μg of ERE DNA were mixed and allowed to react with T4 ligase. From the reaction solution, the DNA was then introduced into E. coli DH5α strain competent cells (TOYOBO). From each of several ampicillin-resistant E. coli colonies, a plasmid DNA was prepared. Each prepared DNA was digested with restriction enzymes Kpn I and Xho I, and the resulting digest was analyzed by agarose gel electrophoresis. A plasmid with a structure in which one copy of ERE DNA was introduced in the Sma I site of pGL3-TATA was termed plasmid pGL3-TATA-ERE, and another plasmid with a structure in which five copies of ERE DNA were introduced in the Sma I site was termed plasmid pGL3-TATA-ERE×5.

Example 13

Reporter Assay Using a Transient Expression Line

Approximately $2\times10^6$ HeLa cells were inoculated on 10 cm plates and incubated in an E-MEM medium containing 10 v/v % of charcoal dextran-treated FBS (hereafter, referred to as FBS) under 5% of $CO_2$ at 37° C. for one day. Then, 3.75 µg of pRc/RSV-BGERβ and 3.75 µg of pGL3-TATA-ERE×5 were transduced together into the cells using Lipofectamine (manufactured by Life Technologies Co., Ltd.) in accordance with the protocol supplied with it. It was incubated at 37° C. for 16 hours, the medium was replaced with a new one, and the incubation was continued for further three hours. Then, the cells were collected, suspended in the E-MEM medium containing 10 v/v % of FBS to disperse, and inoculated on 96-well plates with various concentrations of estradiol (manufactured by Wako Pure Chemical Industries, Ltd.), diethylstilbestrol (DES)(manufactured by Nacalai Tesque, Inc.), p-nonylphenol (manufactured by Kanto Kagaku), bisphenol A (manufactured by Wako Pure Chemical Industries, Ltd.), daidzein (manufactured by Sigma), genistein (manufactured by Wako Pure Chemical Industries, Ltd.), coumesterol (manufactured by INDOFINE Chemical) or o,p'-DDT (Lancaster), all of which were already dissolved with DMSO (final DMSO concentration of 0.1%). In addition, to measure the anti-estrogen activity, the above-mentioned cells were inoculated on the 96-well plates with various concentrations of 4-hydroxytamoxifen and 10 nM E2 added together (final DMSO concentration of 0.1%). The 96-well plates with the cells inoculated on was incubated at 37° C. for approximately 40 hours and an aliquot (50 µl/well) of a cell resolvent PGC50 (manufactured by Nippon Gene Co., Ltd.) diluted to ⅕ concentration was added onto them, and left at room temperature for 30 minutes while carefully shaking them at times to lyse the cells. An aliquot (10 µl) of cell lysate prepared as described above was collected on the white 96-well sample plates (manufactured by BERTHOLD) and luminescence levels were immediately measured for five seconds using a luminometer LB96p with a auto matrix injector (manufactured by BERTHOD) while an aliquot (50 µl/well) of enzyme matrix solution PGL100 (manufactured by Nippon Gene Co., Ltd.) was being added. The result is shown in FIGS. 14 to 22. As described above, the activation ability and anti-activation ability of test substances on estrogen receptor could be measured by the luciferase reporter assay using the inventive gene bgerβ. In addition, by measuring other test substances in the same manner as that of this substance, substances having the activation ability on estrogen receptor or substances having the anti-activation ability on estrogen receptor can be detected.

Example 14

Preparation of the Transformant with the Inventive Gene Transduced into its Chromosome for Reporter Assay The plasmid pUCSV-BSD (purchased from Funakoshi) is digested with BamHI to form a DNA coding for a blasticidin S deaminase gene expression cassette. Further, the plasmid pGL3-TATA-ERE obtained in Example 12 is digested with BamHI and treated with BAP. DNA coding for a blasticidin S deaminase gene expression cassette was then mixed with the restriction digested pGL3-TATA-ERE×5. The resulting DNA mixture is allowed to react with T4 ligase. The DNA is then introduced from the reaction solution into *E. coli* DH5α competent cells (TOYOBO). An ampicillin-resistant colony is isolated, and a plasmid DNA is prepared from the colony by alkali method. The prepared DNA is digested with restriction enzyme BamHI, and the resulting digest is analyzed by agarose gel electrophoresis. A plasmid with a structure in which the blasticidin S deaminase gene expression cassette is inserted in the BamHI restriction site of plasmid pGL3-TATA-ERE is selected and named plasmid pGL3-TATA-ERE-BSD.

The DNA of produced plasmid pGL3-TATA-ERE-BSD and DNA of an expression vector in which the inventive gene is inserted into pRc/RSV are each linearized and then introduced into human-derived HeLa calls as described in Example 11 to obtain a transformant in which these DNAs are introduced into the host cell chromosome.

DNA of plasmid pGL3-TATA-ERE-BSD and DNA of an expression vector in which the inventive gene is inserted into pRc/RSV are each digested with Sal I. HeLa cells are cultured on plates about 10 cm in diameter (Falcon) with a 10% FBS-containing DMEM medium (Nissui Pharmaceutical) at 37° C. under 5% $CO_2$. About $5\times10^5$ cells are cultured for 1 day. The resulting calls are transfected simultaneously with the above linearized DNAs by lipofection method using lipofectin (GIBCO). The lipofection method is performed according to the manual description attached to the lipofectin under the following conditions: a treating time of 5 hours, the total amount of the linearized DNAs of 7 µg (each 3.5 µg) per plate, and a lipofectin amount of 20 µl/plate. After the lipofection, the cells are cultured in situ in the 10% FBS-containing DMEM medium for 3 days. The cells are peeled off from the plate by trypsin treatment and then divided into 10 aliquots, inoculated on 10 plates, respectively, and cultured overnight. G418 (Sigma) is then added to the culture at a final concentration of 400 µg/ml. Blasticidin S is also added to the culture at a final concentration of 8 µg/ml, and the cultivation is further carried out. After one week, the medium is replaced with a fresh one containing G418 and blasticidin S each at the same concentration, and the cultivation is further carried out. After a week, the same process is carried out again. After another week, the plates are observed with an inverted microscope, and 30 colonies with a diameter of several mm are each transferred to each well of a 96-well view plate (Berthold) to which a medium has been added to each well in advance, and the cultivation is further carried out. Before grown in a confluent state, the cells are peeled off by trypsin treatment, collected, divided into 3 aliquots, and inoculated on new 3 96-well view plates, respectively. The cells on one plate are subcultured. E2 is added to one of the remaining two plates at a final concentration of 50 nM, and nothing is added to the other plate. The cells on each plate are cultured for 2 days. After the 2 days, each culture supernatant is removed from each plate, and the cells are washed with 200 µl/well of PBS(-) twice. In order to lyse the cells, cytolytic agent PGC50 (Nippon Gene) 5-fold diluted was then added to each view plate in an amount of 20 µl/well and allowed to stand at room temperature for 30 minutes. The plates are each placed in Luminometer LB96p equipped with an automatic enzyme substrate injector (Berthold). While 50 µl of enzyme substrate solution PGL1000 (Nippon Gene) is automatically added to each well, the luciferase activity is measured. When the luciferase activity of the E2-containing experimental section is at least twice as high as that of the E2-free experimental section, the transformant cells are selected and collected.

Example 15

Reporter Assay Using the Transformant with the Inventive Gene Transduced into its Chromosome The transformat prepared in Example 14 is inoculated on a 24-well plate at a density of about $4\times10^4$ cells/well and cultured under 5% $CO_2$ at 37° C. for 1 day in an E-MEM medium containing 10% of charcoal dextran-treated FBS, 400 µg/ml of G418, and 8 µg/ml of blasticidin S (hereinafter referred to as the FBS and antibiotic-containing E-MEM medium). A test substance DMSO (Wako Pure Chemical) solution is added to the FBS and antibiotic-containing E-MEM medium in different amounts so as to provide final test substance concentrations of 1 nM to 50 µM. Alternatively, DMSO is added to the FBS and antibiotic-containing E-MEM medium in the same amount as that of above each test substance solution. Alternatively, a DMSO solution of E2 is added to the FBS and antibiotic-containing E-MEM medium so as to provide an E2 final concentration of 1 µM. The above cell culture supernatant is replaced with each of the above resulting mediums. The cell culture is held In a $CO_2$ incubator for 24 hours, and then the culture supernatant is removed from the plate. While attention is paid not to peel off the adhering cells from the plate, the cells are washed with 1 ml/well of PBS(−) twice. For the purpose of lysing the cells, cytolytic agent PGC50 (Nippon Gene) 5-fold diluted is added to the plate in an amount of 50 µl/well and allowed to stand at room temperature for 30 minutes while sometimes gently shaken. The resulting lysis solution is placed on a 96-well white sample plate (Berthold) in an amount of 10 µl/well In Luminometer LB96p equipped with an automatic substrate injector (Berthold), enzyme substrate solution PGL100 (Nippon Gene) is added to the plate in an amount of 50 µl/well, and immediately, the luminescence intensity from each well is measured for 5 seconds.

By the luciferase reporter assay using the transformant with the inventive gene transduced into its chromosome as descried above, the test substances containing the substances having the estrogen receptor activating ability can be detected.

Example 16

Preparation of the Vector Containing the Chimera Gene Coding the Fusion Protein of the Ligand Binding Domain of the Inventive BGERβ and the DNA Binding Domain of the Transcription Control Facto PCR (30 cycles conducted wherein one cycle involves Incubation at 94° C. for one minute, 55° C. for one more minute, and then at 74° C. for 1.5 minutes) was performed using the plasmid pGEM-BGERβ, comprising partial nucleotide sequence of the inventive gene bgerβ, as a template, a primer comprising the nucleotide sequences of SEQ ID NO: 34 and a primer comrising the nucleotide sequences of SEQ ID NO: 35 for amplifying the DNA coding the ligand binding domain of the inventive BEGRβ and comprising the nucleotide seuqence represented by nucleotide numbers 763 to 1767 of SEQ ID NO: 24. The amplified DNA was treated with chloroform/phenol and then precipitated with ethanol. The precipitate was centrifugally washed with 70% ethanol and then dried. The DNA was dissolved with TE added and then digested with restriction enzymes EcoRI and SalI at 37° C. for about 5 hours. The digest was subjected to 1% agarose gel electrophoresis and separated. About 1000 bp DNA-containing part of the gel was cut out, and the DNA was recovered from the part using GENECLEAN (Funakoshi). Vector pGBT9 (Clontech) (about 50 ng), for the production of the fusion protein with the DNA binding domain of GAL4 protein, was digested with EcoRI and SalI and then subjected to 1% agarose gel electrophoresis. The EcoRI and SalI-digested vector DNA was then recovered using GENECLEAN (Funakoshi). The recovered vector DNA and about 10 ng of the above recovered DNA were mixed with each other A ligation solution (Ligation Kit, Takara) was added to the mixture in the same volume and incubated at 16° C. for about 5 hours. The resulting mixture was then introduced into competent DH5α cells (TOYOBO) according to the process description attached to the kit. An ampicillin-resistant colony was isolated, and a plasmid DNA was prepared from the colony by alkali method. The nucleotide sequence of the prepared plasmid DNA was confirmed and then named pGBT9-BGER-βLID. This plasmid can be applied to the two-hybrid assay using the budding yeast as the host cell.

Example 17

Preparing the Vector Containing the Chimera Gene Coding the Fusion Protein of the Receptor Binding Domain of the Transcription Coupling Factor and Transcrioption Activating Domain of the Transcription Coupling Factor A cDNA was produced using a human brain-derived mRNA (Clontech) and RT-PCR kit (Takara) in accordance with the protocol attached to the products. PCR was performed using the produced cDNA as a template, using an oligonucleotide comprising the nucleotide sequence of SEQ ID NO:21 and an oligonucleotide comprising the nucleotide sequence of SEQ ID NO:22 as primers and using LA-Taq (Takara) (the PCR reaction conditions: 30 cycles of 94° C. for 1 minute, 55° C. for 1 minute, and 72° C. for 2.5 minutes). The PCR amplified a DNA coding for the amino acid sequence between amino acids 624 and 1287 from the amino terminal end of transcription coupling factor TIF2. The amplified DNA was treated with chloroform/phenol and then precipitated with ethanol. The precipitate was centrifugally washed with 70% ethanol and then dried. The DNA was dissolved with TE added and then digested with restriction enzymes EcoRI and BglII at 37° C. for 5 hours. The digest was subjected to 1% agarose gel electrophoresis and separated. About 2.0 kbp DNA-containing part of the gel was cut out, and the DNA was recovered from the part using GENECLEAN (Funakoshi). Vector pGAD424 (Clontech) (about 50 ng), for the production of the fusion protein with the transcription activating domain of GAL4 protein, was digested with EcoRI and BamHI and then subjected to 1% agarose gel electrophoresis. The EcoRI and BamHI-digested vector DNA was then recovered using GENECLEAN (Funakoshi). The recovered vector DNA and about 10 ng of the above-recovered DNA were mixed with each other. A ligation solution (Ligation Kit, Takara) was added to the mixture in the same volume and incubated at 16° C. for about 1 hour. The resulting mixture was then introduced into E. coli DH5α competent cells (TOYOBO) according to the process description attached to the kit. An ampicillin-resistant colony was isolated, and a plasmid DNA was prepared from the colony by alkali method. The nucleotide sequence of the prepared plasmid DNA was confirmed and then named pGAD424-TIF2RID. This plasmid can be applied to the two-hybrid assay using the budding yeast as the host cell.

Example 18

Preparing the Two-hybrid System Using Budding Yeast Cells as Host Cells

Yeast Y190 (Clontech) was shake-cultured in YPD medium at 30° C. overnight according to the manual of Matchmaker Two-hybrid System (Clontech). The cultured yeast cells were collected and then transfected with pGBT9-BGERβLID obtained in Example 16 and pGAD424-TIF2RID obtained in Example 17 using Yeastmaker yeast transformation system (Clontech). The two plasmid-introduced yeast cells were inoculated on a tryptophan or leucine-free SD nutrient agar and cultured at 30° C. for about 2 days. After the culture was completed, 3 grown colony were selected, applied again on the tryptophan or leucine-free SD nutrient agar, and cultured at 30° C. for about 2 days. The cultured yeast is used for the two-hybrid system.

Example 19

Figure 23:
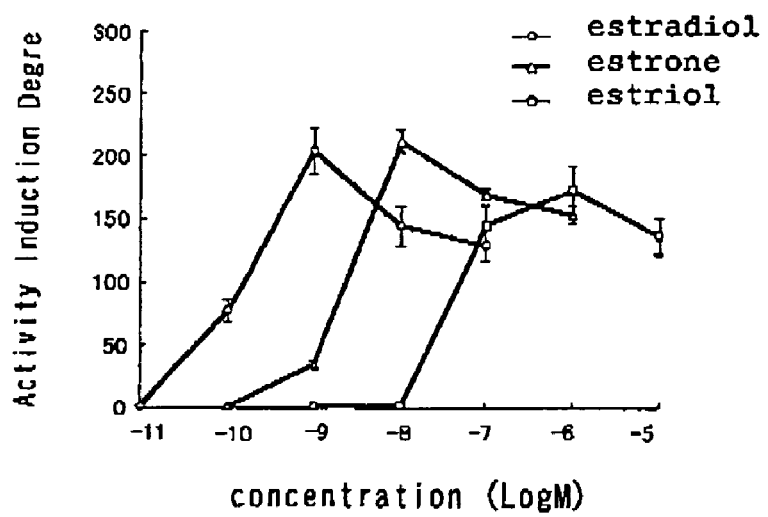
FIG. 23 is a diagram showing a result of measuring the ability of estradiol, estrone and estriol to activate the estrogen receptor activity by the two-hybrid system using the inventive gene, bger β. Along the abscissa axis, the concentration of test compounds are annotated. Along the ordinate axis, the β-galactosidase activity value is shown, where the β-galactosidase activity value of the test compound-free section is normalized as 1.
Figure 24:
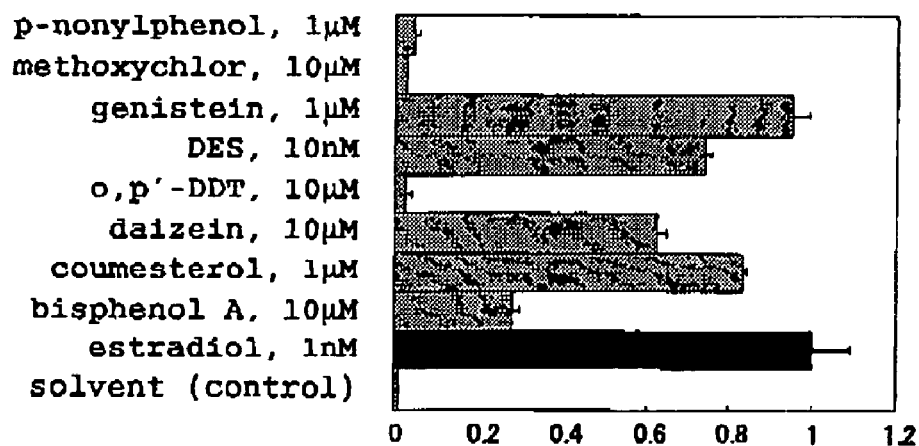
FIG. 24 is a diagram showing a result of measuring the ability of several test compounds to activate the estrogen receptor activity by the two-hybrid system using the inventive gene, bger β. Along the abscissa axis, the β-galactosidase activity value is shown, where the β-galactosidase activity value of a section in which 1 nM of estradiol was added is normalized as 1.

Measuring the Ability of a Test Substance to Regulate Estrogen Receptor Activity Using the Yeast Two-hybrid System Part of yeast prepared in the example 18 was inoculated in 1 ml of tryptophan and leucine-free SD medium, incubated at 30° C. all night while shaking, and the resultant culture solution was diluted to approximate 1/80 concentration with the tryptophan and leucine-free SD medium. On the 96-deep well plate, 2.5 µl of various concentrations of estradiol (manufactured by Wako Pure Chemical Industries, Ltd.), estriol (manufactured by Wako Pure Chemical Industries, Ltd.), estron (manufactured by Wako Pure Chemical Industries, Ltd.), 1 µm of diethylstilbestrol (DES)(manufactured by Nacalai Tesque, Inc.). 1 mM of bisphenol A (manufactured by Wako Pure Chemical Industries, Ltd.), 100 µm of P-nonylphenol (manufactured by Kanto Kagaku), 100 µm of genistein (manufactured by Wako Pure Chemical Industries, Ltd.), 100 µm of coumesterol (manufactured by INDOFINE Chemical Co., Ltd.), 1 µm of daizein (manufactured by Sigma Corp.), 1 µm of methoxychlor (manufactured by Wako Pure Chemical Industries, Ltd.), or 1 mM of o,p'-DDT (manufactured by Lancaster), all of which were already dissolved with DMSO, was added (final concentration of DMSO of 1%). 150 µl of yeast cultured as described above was further added on them, and they were incubated at 30° C. for four hours while shaking. After incubation, 100 µl of yeast solution from each of the wells was collected, 100 µl of luminoreactive solution for β-galactositase activity measurement (Gal-Screen, manufactured by Tropix Corp.) was added on them, incubated at room temperature for approximate 1.5 hours, and the luminoreactive levels were measured using a luminometer LB96p (manufactured by BERTHOLD). FIG. 23 shows the result of concentration-dependent activity induction of E2 (manufactured by Wako Pure Chemical Industries, Ltd.), Ltd.), and estron (manufactured by Wako Pure Chemical Industries, Ltd.). FIG. 24 shows the result of 10 nM (the final concentration) of diethylstilbestrol (DES), 10 µM of bisphenyl A, 1 µM of p-nonylphenol, 1 µM of genistein, 1 µM of coumesterol, 10 µM of daizein, 10 µM of methoxychlor, and 10 µM of o,p'-DDT.

Example 20

Preparing the Recombinant Virus Vector and Recombinant Virus Particles Containing the Inventive Gene Two µg of DNA of the inventive vector pRc/RSV-BGERβ prepared as described in Example 11 was digested with 10 U of the restriction enzyme SpeI and XbaI at 37° C. for one hour, electrophoresis was performed on them using the low melting-point agarose gel, and approximately 1.7 kbp of DNA fragment was collected. The resultant DNA was treated using the DNA blunting kit (manufactured by Takara Shuzo Co., Ltd) to have blunt ends in accordance with the supplied instructions. On the other hand, 2 µg of pVL1392 vector DNA was digested with 10 U of restriction enzyme SmaI, treated with 10 U of alkaline phosphatase at 65° C. for one hour, electrophoresis was performed on it using the low melting-point agarose gel, and the DNAs were collected. Approximately 100 ng of 1.8 kbp DNA prepared from pRc/RSV-BGERβ as mentioned above was added to 100 ng of pVL1392 vector DNA prepared here, and incubated with 5 U of T4 ligase at 16° C. for three hours. This was transduced into the *E. coli* DH5α strain competent cells (manufactured by TOYOBO Co., LTD.) in accordance with the supplied instructions, and the plasmid DNAs were prepared from the resultant colony by the alkaline method. Approximately 1 µg of plasmid DNA samples were digested with 10 U of restriction enzyme XbaI at 37° C. for one hour, electrophoresis was performed on it using Agarose S (manufactured by Nippon Gene Co., Ltd.) for analysis, and clones were screened so that approximately 1.7 kbp of BAND would be detected. Said plasmid DNA was prepared by the alkaline method for using as transfer vectors pVL1392-BGERβ for preparing recombinant Baculo virus.

To a 75 cm² T-flask (Falcon) are added 1×10⁶ of Sf21 cells (available from ATCC), and cultured at 27° C. overnight using a Grace's medium containing 10% FBS and 2% Yeastlate (hereinafter referred to as the FBS-containing Grace medium). To 100 µl of the Grace's medium are added 10 µg of the produced transfer vector pVL1392-BGERβ DNA and 20 ng of linearized viral genome DNA Baculo gold (Pharmingen). After 10 µl of lipofectin (GIBCO) 2-fold diluted with water is further added to the medium, the medium (the lipofectin-DNA mixture solution) is allowed to stand at room temperature for 30 minutes. After the overnight culture, the supernatant is removed from the Sf21 cell culture. The cells are washed with a small amount of a serum-free Grace's medium. To the cells is then added 5 ml of the same medium. The whole amount of the lipofectin-DNA mixture solution is then added to the cells, which is incubated 27° C. for 3 hours. The cells are then washed with the FBS-containing Grace medium. To the cells is also added 20 ml of the FBS-containing Grace medium, and the cells are cultured at 27° C. for 5 days. Day five of the culture, the supernatant is collected in a 50 ml centrifuge tube and centrifuged at 5000×g for 15 minutes to have cell debris precipitated, and then the centrifuged supernatant is collected. The whole amount of the collected supernatant is centrifuged at 100,000×g for 24 hours to give precipitated viral particles that contain the inventive gene. The precipitate is suspended in 100 µl of TE. An equivalent amount of TE-saturated phenol is added thereto and gently mixed at room temperature for 24 hours. After the mixture is centrifuged at 10,000×g for 10 minutes, a water layer is collected. An equivalent amount of chloroform is added to the collected water layer and gently mixed for 10 minutes. The mixture is again centrifuged at 10,000×g for 10 minutes, and then the water layer is collected. To the collected water layer are added NaCl at a final concentration of 0.2 M and a 2.5-fold amount of ethanol, and a viral vector DNA that contains the inventive gene is precipitated and collected.

Example 21

Preparing the Transformant in which the Recombinant Virus Vector of the Present Invention was Transduced into Sf21 Cell and Manufacturing the Estrogen Receptor of the Present Invention To each of ten 75 $cm^2$ T-flasks (Falcon) is added $1 \times 10^6$ of Sf21 cells (available from ATCC), and cultured in the FBS-containing Grace medium at 27° C. In each flask, 10 µl/flask of the culture supernatant, which is prepared in Example 19 and contains the inventive gene-containing recombinant viral particles, is added to the cells, which are cultured in situ for 4 days. The culture supernatant is harvested from each flask and then added to Sf21 cells, which are similarly cultured In each of ten 75 $cm^2$ T-flasks (Falcon), in an amount of 1 ml per flask. The cells are cultured for 60 hours in each flask and then suspended by pipetting and harvested from each flask. The resulting cell suspension is centrifuged at 5,000×g for 15 minutes to have the cells precipitated. The precipitate is suspended in a buffer comprising 20 mM HEPES pH 7, 1 mM EDTA, 1 mM DTT, and 0.5 mM PMSF, and then the suspension is homogenized with 30 up-and-down strokes in a Dounce homogenizer to form a cell homogenate. The homogenate is centrifuged at 30,000×g for 1 hour, and the supernatant fraction is collected to give a fraction that contains the inventive estrogen receptor.

Example 22

Receptor Binding Assay

A binding reaction buffer is prepared to have a final composition of 20 mM HEPES-KOH pH 7.9, 10 mM sodium molybdate, 1 mM DTT, 0.5 mM EDTA, and 0.5 mM PMSF. The reaction solution has a total volume of 100 µl. To the binding reaction buffer are added a 10 µg protein equivalent of the inventive estrogen receptor-containing cell extract and tritium-labeled E2 (which may hereinafter be referred to as the labeled E2) at a content of 1 pM to 100 nM. In the group for determining nonspecific binding, unlabeled E2 is further added at a final concentration of 10 µM to form a reaction solution.

The binding reaction is carried out as follows. After the reaction solution is held on ice for 15 hours, 100 µl of a charcoal dextran liquid (composition: 10 mM Tris-HCl, 0.2% acid-washed active carbon (NoritA, Nacalai Tesque), and 0.005% Pharmacia Dextran T70) is added, and the reaction mixture is allowed to stand on ice for 10 minutes. The reaction mixture is centrifuged at 1,000×g for 10 minutes in a low-speed centrifuge to have the active carbon precipitated, and then 100 µl of the supernatant is sampled. The radioactivity of the sampled supernatant is measured using a liquid scintillation counter. Based on the measured value, the amount of the labeled E2 in the supernatant is determined, which corresponds to the amount of the labeled E2 bound to the estrogen receptor (the amount of the bound form of the labeled ligand). In the experimental section to which only the labeled E2 is added, the amount of the bound form of the labeled ligand corresponds to the total amount of the labeled E2 bound to the estrogen receptor (the total binding amount). In the experimental section to which the labeled E2 and unlabeled E2 are added, the amount of the bound form of the labeled ligand corresponds to the amount of the labeled E2 nonspecifically bound to the receptor (the nonspecific binding amount). As for each of the experimental sections to which the labeled E2 is added at different concentrations, respectively, the nonspecific binding amount is subtracted from the total binding amount to produce the amount of the labeled ligand specifically bound to the estrogen receptor (the specific binding amount) in each group. Thereafter, the value of (the concentration of the labeled ligand specifically bound)/(the concentration of the free form of the labeled ligand) is plotted against the Y-axis, and the concentration of the labeled ligand specifically bound is plotted against the X-axis. The Scatchard analysis is performed to produce a Kd value of the inventive estrogen receptor with respect to E2.

In order to determine the affinity of a test substance for the inventive estrogen receptor, the test substance is added at a final concentration of about 1% to the binding assay reaction solution, which contains about 1 nM of the labeled E2 similarly to the above. In the test substance-free experimental section, the same amount of solvent is added to the reaction solution in place of the test substance. When the addition of the test substance reduces the amount of the labeled E2 bound to the estrogen receptor, the test substance is determined as an estrogen receptor binding substance.

INDUSTRIAL APPLICABILITY

According to the present invention, the novel estrogen receptor gene and the like can be applied to assay systems for evaluating the ability of chemical substances to regulate the estrogen receptor activity.

The invention claimed is:

1. An isolated estrogen receptor coding sequence comprising a nucleotide sequence coding for any of the following amino acid sequences (a) to (e):
   (a) the amino acid sequence of SEQ ID NO: 1,
   (b) the amino acid sequence of SEQ ID NO: 4,
   (c) an amino acid sequence exhibiting 95% or more amino acid identity to the amino acid sequence of SEQ ID NO: 1, and has estrogen binding activity; and
   (d) an amino acid sequence exhibiting 95% or more amino acid identity to the amino acid sequence of SEQ ID NO: 4, and has estrogen binding activity, and
   (e) a fragment of any of amino acid sequences (a) through (d) comprising the ligand binding domain of the estrogen receptor and has estrogen binding activity.

2. An isolated estrogen receptor coding sequences comprising any of the following nucleotide sequences (a) or (b):
   (a) the nucleotide sequence represented by nucleotide numbers 424 to 1941 of SEQ ID NO: 2, or
   (b) the nucleotide sequence represented by nucleotide numbers 74 to 1819 of SEQ ID NO: 5.

3. A vector comprising the estrogen receptor coding sequences according to claim 1.

4. The vector according to claim 3, wherein a promoter is operably linked to the estrogen receptor coding sequences.

5. The vector according to claim 3, wherein the vector is a viral vector.

6. A viral particle containing the vector according to claim 5.

7. A method for producing a vector, comprising incorporating the estrogen receptor coding sequence according to claim 1 into a vector replicable in a host cell.

8. A transformant produced by introducing the estrogen receptor coding sequences according to claim 1 into a host cell, wherein the host cell is isolated or cultured in vitro.

9. A transformant produced by introducing the vector according to claim 3 into a host cell, wherein the host cell is isolated or cultured in vitro.

10. The transformant according to claim 8, comprising the estrogen receptor coding sequences in a chromosome of the host cell.

11. The transformant according to claim 8, wherein the host cell is an animal cell.

12. The transformant according to claim 8, wherein the host cell is a mammalian cell.

13. The transformant according to claim 8, wherein the host cell is an insect cell.

14. The transformant according to claim 8, wherein the host cell is a yeast cell.

15. A method for producing a transformant, comprising introducing the estrogen receptor coding sequences according to claim 1 into a host cell.

16. A method for manufacturing an estrogen receptor, comprising culturing the transformant according to claim 8, thereby producing the estrogen receptor.

17. An isolated estrogen receptor, comprising any of the following amino acid sequences (a) to (d):
   (a) the amino acid sequence of SEQ ID NO: 1,
   (b) the amino acid sequence of SEQ ID NO: 4,
   (c) an amino acid sequence exhibiting 95% or more amino acid identity to the amino acid sequence of SEQ ID NO: 1 and has estrogen binding activity,
   (d) an amino acid sequence exhibiting 95% or more amino acid identity to the amino acid sequence of SEQ ID NO: 4, and has estrogen binding activity.

18. A method for evaluating the ability of a test substance to regulate estrogen receptor activity, comprising:
   bringing the test substance into contact with a transformant, wherein the transformant comprises a reporter gene linked downstream of a transcriptional control region and the estrogen receptor coding sequences according to claim 1, and wherein the transcriptional control region includes an estrogen response element sequence, and
   measuring the amount of expression of the reporter gene from the transformant.

19. A receptor binding assay, comprising:
   (a) bringing a test substance into contact with the estrogen receptor according to claim 17,
   (b) incubating the test substance together with the estrogen receptor and
   (c) detecting the binding of the test substances with the estrogen receptor.

20. A method for measuring the ability of a test substance to regulate estrogen receptor activity comprising:

(A) measuring any variation in expression amount of a reporter gene in a two-hybrid system when the test substance is added to the two-hybrid system, wherein in the two-hybrid system ligand-dependent formation of a complex results in activation of transcription of the reporter gene, wherein the complex comprises (i) an estrogen binding protein encoded by the estrogen receptor coding sequences according to claim 1 and (ii) a transcription coupling factor capable of ligand-dependently binding to the estrogen receptor or a receptor binding domain of the transcription coupling factor; and (B) evaluating the ability of the test substance to regulate estrogen receptor activity.

* * * * *